(12) United States Patent
Kerfeld et al.

(10) Patent No.: US 10,501,508 B2
(45) Date of Patent: Dec. 10, 2019

(54) MINIMIZED CYANOBACTERIAL MICROCOMPARTMENT FOR CARBON DIOXIDE FIXATION

(71) Applicant: Board of Trustees of Michigan State University, East Lansing, MI (US)

(72) Inventors: Cheryl A. Kerfeld, Okemos, MI (US); Cesar R. Gonzalez, White Rock, NM (US)

(73) Assignee: Board of Trustees of Michigan State University, East Lansing, MI (US)

(*) Notice: Subject to any disclaimer, the term of this patent is extended or adjusted under 35 U.S.C. 154(b) by 37 days.

(21) Appl. No.: 15/685,742

(22) Filed: Aug. 24, 2017

(65) Prior Publication Data

US 2018/0057546 A1 Mar. 1, 2018

Related U.S. Application Data

(60) Provisional application No. 62/378,979, filed on Aug. 24, 2016.

(51) Int. Cl.
| | | |
|---|---|---|
| *C12N 9/14* | (2006.01) | |
| *C07K 14/405* | (2006.01) | |
| *C10L 1/02* | (2006.01) | |
| *C12N 1/32* | (2006.01) | |
| *C12P 5/00* | (2006.01) | |
| *C12P 39/00* | (2006.01) | |

(52) U.S. Cl.
CPC .............. *C07K 14/405* (2013.01); *C10L 1/02* (2013.01); *C12N 1/32* (2013.01); *C12N 9/14* (2013.01); *C12P 5/007* (2013.01); *C07K 2319/00* (2013.01); *C12P 39/00* (2013.01)

(58) Field of Classification Search
None
See application file for complete search history.

(56) References Cited

FOREIGN PATENT DOCUMENTS

| WO | WO-2011094765 A2 * | 8/2011 | ............ C07K 14/195 |
| WO | WO-2014182968 A2 * | 11/2014 | ......... C12N 15/8214 |
| WO | WO-2016077589 A1 * | 5/2016 | ................ C12N 9/88 |

OTHER PUBLICATIONS

Ngo et al. In the Protein Folding Problem and Tertiary Structure Prediction, 1994, Merz et al. (ed.), Birkhauser, Boston, MA, pp. 433 and 492-495.*
Aussignargues, Clement, et al., "Bacterial microcompartment assembly: The key role of encapsulation peptides", Communicative & Integrative Biology 8:3, e1039755, (May/Jun. 2015), 10 pages.
Axen, Seth D., et al., "A Taxonomy of Bacterial Microcompartment Loci Constructed by a Novel Scoring Method", PLOS Comput. Biol. 10(10), e1003898., (Oct. 2014), 1-20.
Baker, Neil R., et al., "Chlorophyll Fluorescence: A Probe of Photosynthesis in Vivo", Annu. Rev. Plant Biol., 59, (2008), 89-113.
Biasini, Marco, et al., "Swiss-Model: modelling protein tertiary and quaternary structure using evolutionary information", Nucleic Acids Research, vol. 42, (2014), W252-W258.
Cai, Fei, et al., "Advances in Understanding Carboxysome Assembly in *Prochlorococcus* and *Synechococcus* Implicate CsoS2 as a Critical Componet", Life, 5, (2015), 1141-1171.
Cai, Fei, "Production and Characterization of Synthetic Carboxysome Shells with Incorporated Luminal Proteins[1][OPEN]", Plant Physiology, vol. 170, (Mar. 2016), 1868-1877.
Cai, Fei, et al., "The Pentameric Vertex Proteins Are Necessary for the Icosahedral Carboxysome Shell to Function as a $CO_2$ Leakage Barrier", PLoS One 4(10), e7521, (Oct. 2009), 1-9.
Cameron, Jeffrey C., "Biogenesis of a Bacterial Organelle: The Carboxysome Assembly Pathway", Cell, 155, (2013), 1131-1140.
Chen, Anna H., et al., "The Bacterial Carbon-Fixing Organelle Is Formed by Shell Envelopment of Preassembled Cargo", PLoS One, 8(9), e76127, (Sep. 2013), 1-13.
Cheng, Shouqiang, et al., "Bacterial microcompartments: their properties and paradoxes", BioEssays, 30(11-12), (2008), 1084-1095.
Dragosits, Martin, et al., "Adaptive laboratory evolution— principles and applications for biotechnology", Microbial. Cell Factories, 12: 64, (2013), 17 pgs.
Drews, G., et al., "Beiträge zur Cytologie der Blaualgen [Cytology of Cyanophycea. II. Centroplasm and granular inclusions of Phormidium uncinatum].", Archiv fur Mikrobiologie, 24, II. Mitteilung Zentroplasma und granulare Einschlusse von Phormidium uncinatum, (1956), 147-162.
Frank, Stefanie, et al., "Bacterial microcompartments moving into a synthetic biological world", J. Biotechnol., 163(2), (2013), 273-279.
Gantt, E., et al., "Ultrastructure of Blue-Green Algae", J. Bacteriol., 97(3), (1969), 1486-1493.
Hunter, S., et al., "InterPro in 2011: new developments in the family and domain prediction database", Nucleic Acids Res., 40(Database Issue), (2012), D306-D312.
Kerfeld, Cheryl A., et al., "Bacterial microcompartments and the modular construction of microbial metabolism", Trends Microbiol., 23, (2015), 22-34.
Kinney, James N., et al., "Elucidating Essential Role of Conserved Carboxysomal Protein CcmN Reveals Common Feature of Bacterial Microcompartment Assembly", J. Biol. Chem. 287(21), (2012), 17729-17736.
Kufryk, G. I., "Transformation of the cyanobacterium *Synechocystis* sp. PCC 6803 as a tool for genetic mapping: optimization of efficiency", FEMS Microbiol. Lett., 206, (2002), 215-219.

(Continued)

*Primary Examiner* — Richard G Hutson
(74) *Attorney, Agent, or Firm* — Schwegman Lundberg & Woessner, P.A.

(57) ABSTRACT

A fusion chimeric protein is described herein that can assemble a functional carboxysome core, which is able to fix carbon by taking atmospheric carbon dioxide and converting it into useful carbon-containing compounds such as 3-phosphoglycerate (3-PGA).

3 Claims, 9 Drawing Sheets
(4 of 9 Drawing Sheet(s) Filed in Color)
Specification includes a Sequence Listing.

(56) References Cited

OTHER PUBLICATIONS

Lagarde, Delphine, et al., "Increased Production of Zeaxanthin and Other Pigments by Application of Genetic Engineering Techniques to *Synechocystis* sp. Strain PCC 6803", Appl. Environ. Microbiol., 66(1), (2000), 64-72.

Landgraf, Dirk, et al., "Segregation of molecules at cell division reveals native protein localization", Nat. Methods, 9(5), (2012), 480-482.

Lawrence, Andrew D., et al., "Solution Structure of a Bacterial Microcompartment Targeting Peptide and Its Application in the Construction of an Ethanol Bioreactor", ACS Synthetic Biology, 3(7), (2014), 454-465.

Lichtenthaler, Hartmut K., "[34] Chlorophylls and Carotenoids: Pigments of Photosynthetic Biomembranes", Methods in Enzymology, 148, (1987), 350-382.

Lin, Myat T., et al., "A faster Rubisco with potential to increase photosynthesis in crops", Nature, 513(7519), (2014), 547-550.

Lin, Myat T., et al., "ß-Carboxysomal proteins assemble into highly organized structures in *Nicotiana* chloroplasts", Plant J., 79(1), (2014), 1-12.

Lluch-Senar, Maria, et al., "Defining a minimal cell: essentiality of small ORFs and ncRNAs in a genome-reduced bacterium", Mol. Syst. Biol., 11: 780, (2015), 1-7.

Long, Benedict M., et al., "Analysis of Carboxysomes from *Synechococcus* PCC7942 Reveals Multiple Rubisco Complexes with Carboxysomal Proteins CcmM and CcaA", J. Biol. Chem., 282(40), (2007), 29323-29335.

Long, Benedict M., et al., "Functional Cyanobacterial ß-Carboxysomes Have an Absolute Requirement for Both Long and Short Forms of the CcmM Protein $^{1[W][OA]}$", Plant Physiology, 153, (May 2010), 285-293.

Marsh, Joseph A., "Protein Complexes Are under Evolutionary Selection to Assemble via Ordered Pathways", Cell, 153, (2013), 461-470.

Pena, Kerry L., et al., "Structural basis of the oxidative activation of the carboxysomal γ-carbonic anhydrase, CcmM", Proc. Natl. Acad. Sci. USA, 107(6), (2010), 2455-2460.

Pettersen, Eric F., et al., "UCSF Chimera—a visualization system for exploratory research and analysis", J Comput Chem., 25(13), (2010), 1605-1612.

Price, G. Dean, et al., "Advances in understanding the cyanobacterial $CO_2$-concentrating-mechanism (CCM): functional components, Ci transporters, diversity, genetic regulation and prospects for engineering into plants", Journal of Experimental Biology, 59(7), (2008), 1441-1461.

Price, G. D., et al., "Isolation and Characterization of High $CO_2$-Requiing-Mutants of the Cyanobacterium *Synechococcus* PCC7942", Plant Physiology, 91, (1989), 514-525.

Price, G. Dean, et al., "The cyanobacterial CCM as a source of genes for improving photosynthetic $CO_2$ fixation in crop species", Journal of Experimental Biology. 64(3), (2013), 753-768.

Reynolds, E. S., et al., "The use of lead citrate at high pH as an electron-opaque stain in electron microscopy", J. Cell Biol. 17, (1963), 208-212.

Rippka, Rosmarie, et al., "Generic Assignments, Strain Histories and Properties of Pure Cultures of Cyanobacteria", J. Gen. Microbiol., 111, (1979), 1-61.

Rokney, Assaf, "*E. coli* transports aggregated proteins to the poles by a specific and energy-dependent process", J. Mol. Biol., 392(3), (2009), 589-601.

Savage, Didi F., et al., "Spatially ordered dynamics of the bacterial carbon fixation machinery", Science, 327(5970), (2010), 1258-1261.

Schneider, C. A., et al., "NIH Image to ImageJ: 25 years of image analysis", Nat. Methods 9(7), (2012), 671-675.

So, Anthony K.-C., et al., "Characterization of a mutant lacking carboxysomal carbonic anhydrase from the cyanobacterium *Synechocystis* PCC6803", Planta 214(3), (2002), 456-467.

So, Anthony K.-C., et al., "Characterization of the C-terminal extension of carboxysomal carbonic anhydrase from *Synechocystis* sp. PCC6803", Funct. Plant Biol., 29(3), (2002), 183-194.

Takahashi, Shunichi, et al., "Interruption of the Calvin cycle inhibits the repair of Photosystem II from photodamage", Biochim. Biophys. Acta (BBA)—Bioenergetics, 1708(3), (2005), 352-361.

Zarzycki, Jan, et al., "Cyanobacterial-based approaches to improving photosynthesis in plants", Journal of Experimental Botany, 64(3), (2013), 787-798.

\* cited by examiner

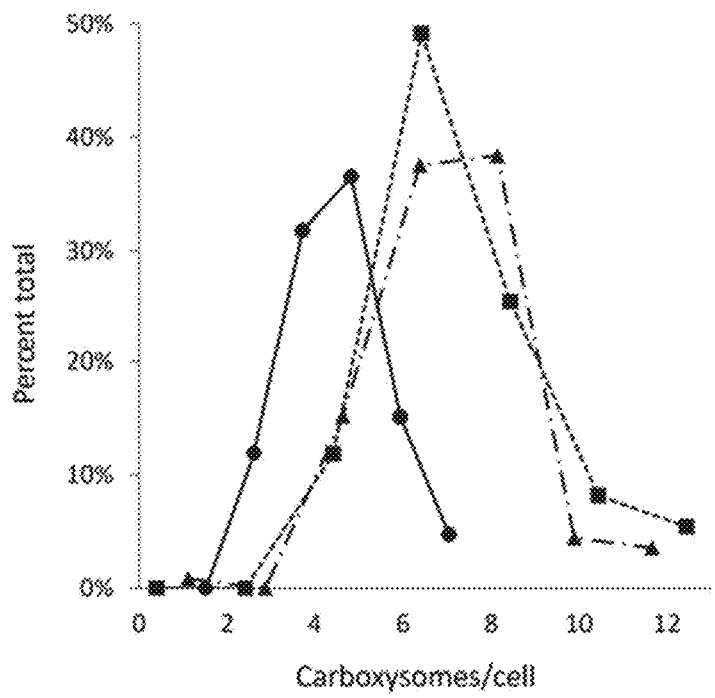
FIG. 4A
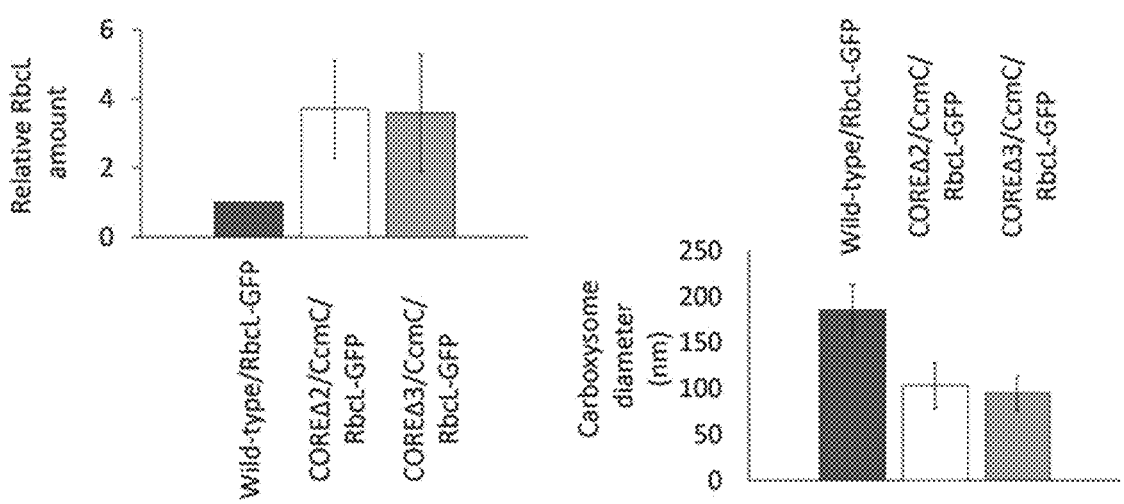
FIG. 4B
FIG. 4C

MINIMIZED CYANOBACTERIAL MICROCOMPARTMENT FOR CARBON DIOXIDE FIXATION

This application claims benefit of priority to the filing date of U.S. Provisional Application Ser. No. 62/378,979, filed Aug. 24, 2016, the contents of which are specifically incorporated herein by reference in their entity.

FEDERAL FUNDING

This invention was made with government support under DE-FG02-91ER20021 awarded by the U.S. Department of Energy. The government has certain rights in the invention.

BACKGROUND OF THE INVENTION

Like plants and algae, cyanobacteria obtain energy from photosynthesis, utilizing energy from sunlight and electrons from water to reduce carbon dioxide ($CO_2$) and thereby 'fix' carbon into cell biomass. This photosynthetically-fixed carbon can then be used to make metabolites, such as carbohydrates, proteins, and fatty acids that are ultimately distributed to heterotrophic organisms. Besides their role as primary carbon fixation organisms, cyanobacteria can also be altered to produce useful products. For example, *Synechococcus elongatus* PCC 7942 has been engineered to produce isobutyraldehyde and butanol; *Synechocystis* sp. PCC 6803 has been modified produce ethanol and isoprene.

Cyanobacteria excel at carbon fixation, thanks to their complex carbon concentrating mechanism (ccm), which is comprised of bicarbonate pumps, carbon dioxide-uptake systems and the carboxysome. The carboxysome is an approximate 300 MDa compartment essential for carbon concentration, as it enhances carbon fixation by sequestering ribulose-1,5-bisphosphate carboxylase/oxygenase (Rubisco) and carbonic anhydrase (CA) within a protein shell. In the carboxysome lumen, bicarbonate is converted into carbon dioxide by carbonic anhydrase. Such conversion increases the proportion of carbon dioxide to oxygen in the vicinity of Rubisco, which favors Rubisco's carboxylase activity, while the shell limits the loss of carbon dioxide into the bulk cytosol (Cai et. al, 2009).

Researchers have explored ways to express the β-carboxysome shell and cyanobacterial form 1B Rubisco in chloroplasts (Lin et al., 2014b; Lin et al., 2014a). However, constructs have not been generated that can assemble the functional multi-protein metabolic carboxysome core.

SUMMARY

In cyanobacteria, the key enzyme for photosynthetic $CO_2$ fixation, ribulose-1,5-bisphosphate carboxylase/oxygenase (Rubisco), is bound within proteinaceous polyhedral microcompartments called carboxysomes. A streamlined carboxysome is described herein that was generated by fusing key domains from four proteins into a single protein. This chimeric protein assembles into a functional carboxysome core that can readily be transferred and utilized in other organisms. This is the first instance of the redesign and construction of a carboxysome core, the first instance of a re-design of a bacterial microcompartment core, and lays the base for the generation of novel compartments with industrially relevant functions based on the carboxysome and related bacterial microcompartment architectures.

Described herein are fusion proteins that include a polypeptide comprising at least two small subunit-like domains (SSLDs) from a carbon dioxide concentrating mechanism (CcmM) protein, at least one carbonic anhydrase domain, and at least one encapsulation peptide. The at least two small subunit-like domains (SSLDs) from a carbon dioxide concentrating mechanism (CcmM) protein can bind or nucleate with ribulose-1,5-bisphosphate carboxylase/oxygenase (Rubisco). The Rubisco can, for example, synthesize 3-phosphoglycerate (3-PGA). In some cases, the at least two small subunit-like domains (SSLDs) from a carbon dioxide concentrating mechanism (CcmM) protein can have a protein sequence with at least 95% sequence identity to any of SEQ ID NO:1-11, 37, 75, 76, or 77.

The at least one carbonic anhydrase domain is an enzyme that can convert bicarbonate to carbon dioxide. For example, the at least one carbonic anhydrase domain comprises at least 95% sequence identity to any of SEQ ID NO:17-21 or 71.

The at least one encapsulation peptide can interact with, nucleate, and/or bind one or more carboxysome shell protein. In some cases, the at least one encapsulation peptide comprises at least 95% sequence identity to any of SEQ ID NO:12-15 or 16.

Also described herein are expression cassettes that can include a promoter operably linked to a nucleic acid segment encoding such a fusion protein. Cells, plants, bacteria, algae, and/or microalgae can be modified to include such expression cassettes.

Methods are also described herein that can provide carbon fixation. Such methods can include culturing the cells that have nucleic acids or expression vectors that encode any of the fusion proteins described herein. The methods can involve cultivating one or more plants that have nucleic acids or expression vectors that encode any of the fusion proteins described herein. Such cells, plants, bacteria, algae, and/or microalgae can manufacture products such as 3-phosphoglycerate (3-PGA). Such cells, plants, bacteria, algae, and/or microalgae can be cultivated or cultured and then harvested. Products can be harvested from the cells, plants, bacteria, algae, and/or microalgae. Such products can include oils, carbohydrates, grains, vegetables, fruits and other components, as well as 3-phosphoglycerate (3-PGA).

DESCRIPTION OF THE FIGURES

The patent or application file contains at least one drawing executed in color. Copies of this patent or patent application publication with color drawing(s) will be provided by the Office upon request and payment of the necessary fee.

FIG. 1A is a schematic diagram of the architecture of domains in the CcmM, CcmN, CcaA and CcmC proteins that recruit Rubisco and assemble the carboxysome core. FIG. 1B schematically illustrates the architecture and structure of the domains of the constructed chimeric protein, CcmC. SSLD: Small subunit-like domain. EP: Encapsulation peptide. CA: Carbonic anhydrase. FIG. 1C is a schematic diagram of the native β-carboxysome core protein. The shell of the native β-carboxysome core protein includes the CcmL (pentagon), CcmO (hexagon), and CcmK (hexagon) polypeptides encoded by the ccm operon. The core of the native β-carboxysome core protein includes the other proteins encoded by the ccm operon. FIG. 1D is a schematic diagram of the CcaA-M35 construct, which is a fusion of CcaA and 3×SSLDs, and which was determined to not be a successful design. FIG. 1E is a schematic diagram of the M35-EP construct, which is a fusion of the Encapsulation peptide of CcmN and three SSLDs, and which was also determined to not be a successful design. FIG. 1F is a schematic diagram of the CcmC fusion of the Encapsulation peptide of CcmN, a shortened version of CcaA (central flattened circle linked to a pentagon), and three SSLDs (three rectangles at the bottom that bind or nucleate with the CcaA). The shell of the chimeric cyanobacterial carboxysome protein includes the CcmL (pentagon), CcmO (hexagon), and CcmK (hexagon) polypeptides encoded by the ccm operon. Gray shading between polypeptide domains denotes known non-covalent domain interactions. SSLD: small subunit-like domain. EP: Encapsulation peptide. FIG. 1G illustrates assembly of a native β-carboxysome core. FIG. 1H illustrates assembly of the designed carboxysome core by the chimeric protein CcmC (yellow). For FIGS. 1G and 1H, the small subunit-like domains (SSLDs) are numbered from the N-terminal (SSLD1) to C-terminal (SSLD3). The specific details of their interactions with the large subunit of Rubisco are unknown, but they may displace some of the RbcS subunits, which are not shown. Domains are colored as in FIGS. 1A and 1B. Shell proteins are shown in blue, while four RbcL subunits of the L8S8 complex of Rubisco are shown in green. Gray shading denotes known noncovalent domain interactions with a numbers in parenthesis for the corresponding reference: (1) and (2) from Kinney et al. (2012), (3) from Long et al. (2007) and (4) from Long et al. (2010).

FIG. 3 panels A-D show fluorescence of cyanobacteria strains expressing RbcL-GFP for carboxysome visualization by microscopy. FIG. 3 panel A illustrates fluorescence of wild-type/RbcL-GFP cyanobacteria. FIG. 3 panel B illustrates fluorescence of COREΔ2/RbcL-GFP cyanobacteria. FIG. 3 panel C illustrates fluorescence of COREΔ2/CcmC/RbcL-GFP cyanobacteria. FIG. 3 panel D illustrates fluorescence of COREΔ3/CcmC/RbcL-GFP cyanobacteria. Scale bar: 5 μm. FIG. 3 panels E-H show electron micrographs of the same strains after incubation for at least 12 hours in air. FIG. 3 panel E shows images of wild-type/RbcL-GFP cyanobacteria. FIG. 3 panel F shows images of COREΔ2/RbcL-GFP cyanobacteria. FIG. 3 panel G shows images of COREΔ2/CcmC/RbcL-GFP cyanobacteria. FIG. 3 panel H shows images of COREΔ3/CcmC/RbcL-GFP cyanobacteria. Arrowheads: carboxysomes. Scale bar: 500 nm.

FIG. 4A-4C illustrates the structural features of native and minimized carboxysomes. FIG. 4A graphically illustrates the distribution of the number of carboxysomes per cell (n≤100), where the solid line (solid circle symbols) shows results for wild-type/RbcL-GFP, the dash-dotted line (triangle symbols) shows results for COREΔ2/CcmC/RbcL-GFP, and the dashed line (square symbols) shows results for COREΔ3/CcmC/RbcL-GFP. FIG. 4B graphically illustrates the relative RbcL content in protein samples normalized to Chlorophyll a (n=3), where the dark gray bar shows results for wild-type/RbcL-GFP, the open (white) bar shows results for COREΔ2/CcmC/RbcL-GFP, and the light gray bar shows results for COREΔ3/CcmC/RbcL-GFP. FIG. 4C graphically illustrates the carboxysome diameters measured from electron micrographs (n=50), where the dark gray bar shows results for wild-type/RbcL-GFP, the open (white) bar shows results for COREΔ2/CcmC/RbcL-GFP, and the light gray bar shows results for COREΔ3/CcmC/RbcL-GFP. Error bars=std. dev.

FIG. 5A shows the changes in optical density (730 nm) over time of independent cultures grown in air (n=3). Wild type/RbcL-GFP (circles), COREΔ2/CcmC/RbcL-GFP (triangles), and COREΔ3/CcmC/RbcL-GFP (squares) show similar growth rates. Note that the COREΔ2/RbcL-GFP (without the CcmC construct; diamond symbols) failed to grow in air. The inset chart shows doubling times calculated by exponential regression curve fitting (see website at doubling-time.com/compute.php). FIG. 5B shows the changes in optical density (730 nm) over time of independent cultures grown in 5% $CO_2$ (n=3). Wild type/RbcL-GFP (circles), COREΔ2/CcmC/RbcL-GFP (triangles), and COREΔ3/CcmC/RbcL-GFP (squares) show similar growth rates when detected by optical density (730 nm). Error bars=std. dev. The inset chart shows doubling times calculated by exponential regression curve fitting (see website at doubling-time.com/compute.php).

FIG. 6A graphically illustrates the average absorbance spectra of whole cell suspensions normalized to Chlα (663 nm), where the solid line shows data for wild-type/RbcL-GFP cells, and the dashed line shows data for COREΔ3/CcmC/RbcL-GFP cells (n=3). FIG. 6B graphically illustrates changes over time of $F_v/F_m$ in cultures grown at 3% $CO_2$ and transferred to air at time=0 h, where the solid line shows data for wild-type/RbcL-GFP cells (circle symbols), the dashed line shows data for COREΔ3/CcmC/RbcL-GFP cells (square symbols), and the dashed, dotted line shows data for COREΔ2/RbcL-GFP cells (triangle symbols) (n=3). FIG. 6C graphically illustrates oxygen evolution rates (normalized to Chl α) at high light intensity of strains grown in air and supplemented with 10 mM bicarbonate (left) with a comparison of Chl α per ml of $OD_{730}$ culture (right), where the dark grey bars are data for wild-type/RbcL-GFP cells and the light grey bars are data for COREΔ3/CcmC/RbcL-GFP cells. (n≤5). Error bars=std. dev.

DETAILED DESCRIPTION

A chimeric protein is described herein that can assemble into a functional carboxysome core and that is able to fix carbon by taking atmospheric carbon dioxide and converting it into useful carbon-containing molecules such as 3-phosphoglycerate (3-PGA or also referred to as glycerate 3-phosphate). 3PGA is a precursor for other useful molecules such as serine, which, in turn, can create cysteine and glycine through the homocysteine cycle.

Figure 1A:
FIG. 1A-1H illustrate construction of a chimeric cyanobacterial carboxysome core.
Figure 1B:
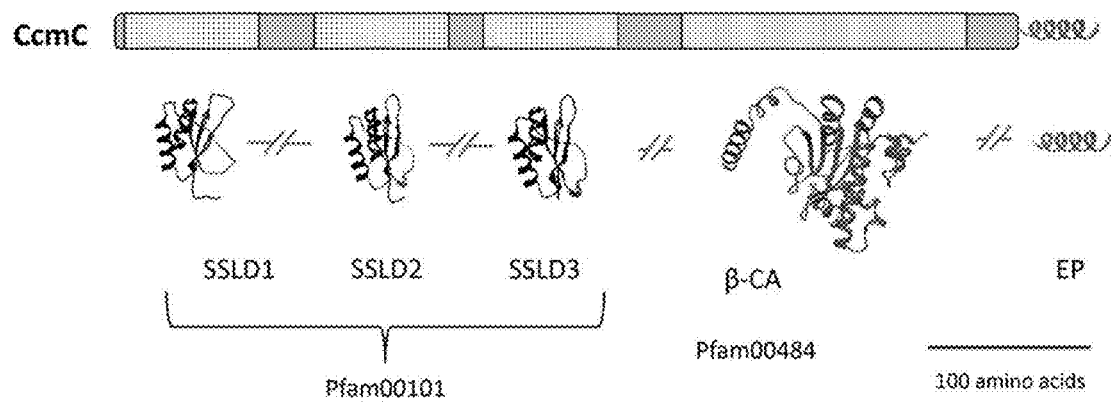
Figure 1C:
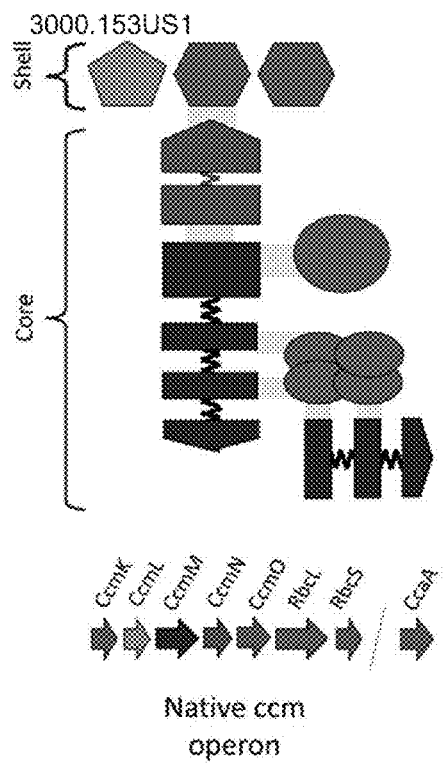
Figure 1D:
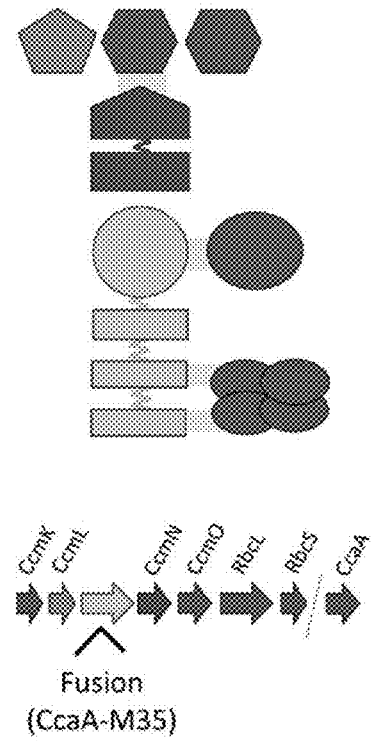
Figure 1E:
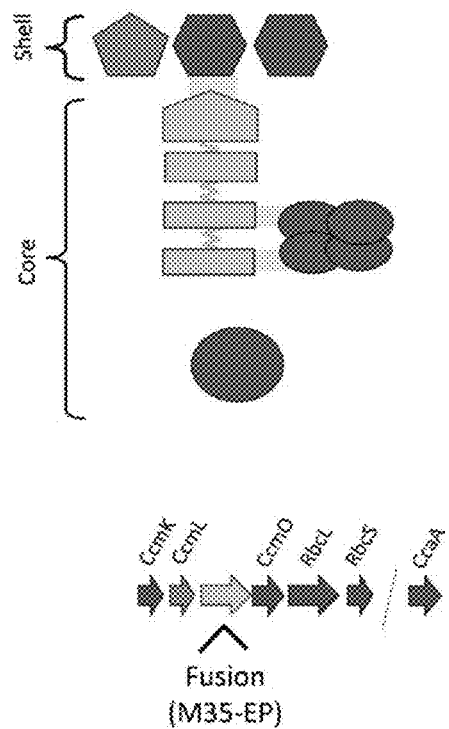
Figure 1F:
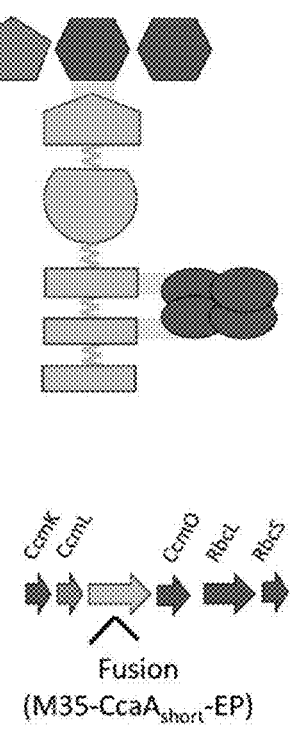
Figure 1H:
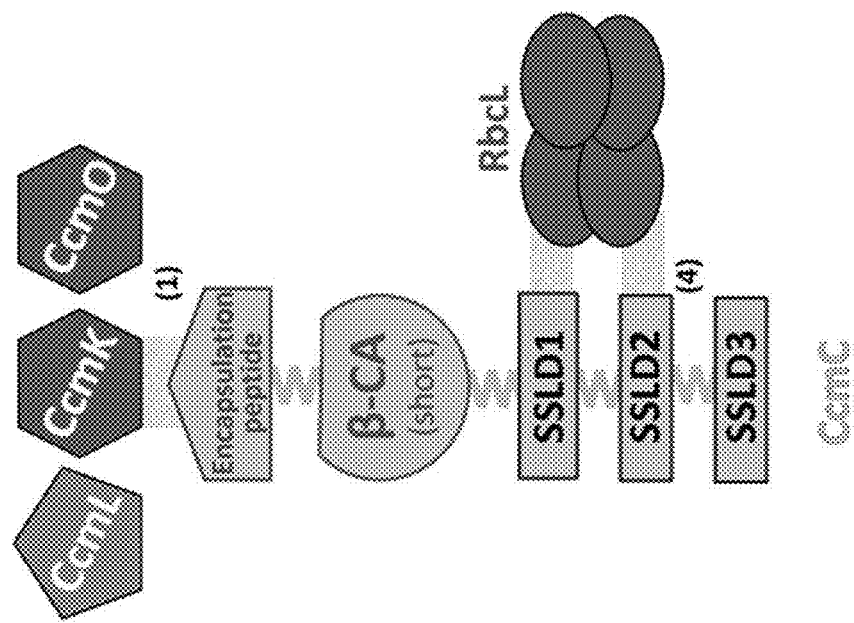

The chimeric protein is referred to as CcmC (where the final "C" is for chimeric). The CmcC protein structure is schematically illustrated in FIGS. 1B and 1H. The chimeric CcmC protein can be expressed in a variety of organisms. For example, although the CcmC protein has been generated from cyanobacterial components, it can be expressed in a variety of organisms such as bacteria, plants, microalgae and other organisms to assemble organelles that remove carbon dioxide from the atmosphere and provide organic carbon to facilitate growth and synthesis of useful products. The chimeric protein does not exist in nature, it was designed and synthesized recombinantly.

The chimeric protein structurally and functionally replaces four gene products required for carboxysome formation (see schematic illustrations in FIGS. 1B and 1H). The CcmC protein contains scaffolding domains (the Small RbcS subunit-like domains that are involved in nucleating Ribulose-1,5-bisphosphate carboxylase/oxygenase (commonly known by the abbreviation Rubisco), an enzymatic domain (carbonic anhydrase), and an encapsulating domain (the encapsulation peptide).

Functional carboxysomes are needed for the survival of a cyanobacterial host. As illustrated herein, the chimeric CcmC protein can replace the function of native carboxysomes in cyanobacteria.

In CcmC, the small subunit-like domains (SSLDs) and the Encapsulation peptide (EP) are fused to opposite ends of the beta-carbonic anhydrase (β-CA) domain. The SSLDs are available to interact with the large subunit of Rubisco and the Encapsulation peptide can interact with the shell (see FIGS. 1H and 1B). The resulting 67 kDa chimeric protein replaces the 58 kDa CcmM, the 35 kDa M35, the 16 kDa CcmN, and the 30 kDa CcaA proteins that are part of the native (wild type) cyanobacterial carboxysome core protein.

The CcmC construct reduces the genomic load required to assemble a carboxysome by about 1100 bp, which is about 18% of total message required for wild type carboxysomes. In addition, it reduces the number of proteins and, concomitantly, the need to balance the expression levels of four different genes.

Figure 5B:
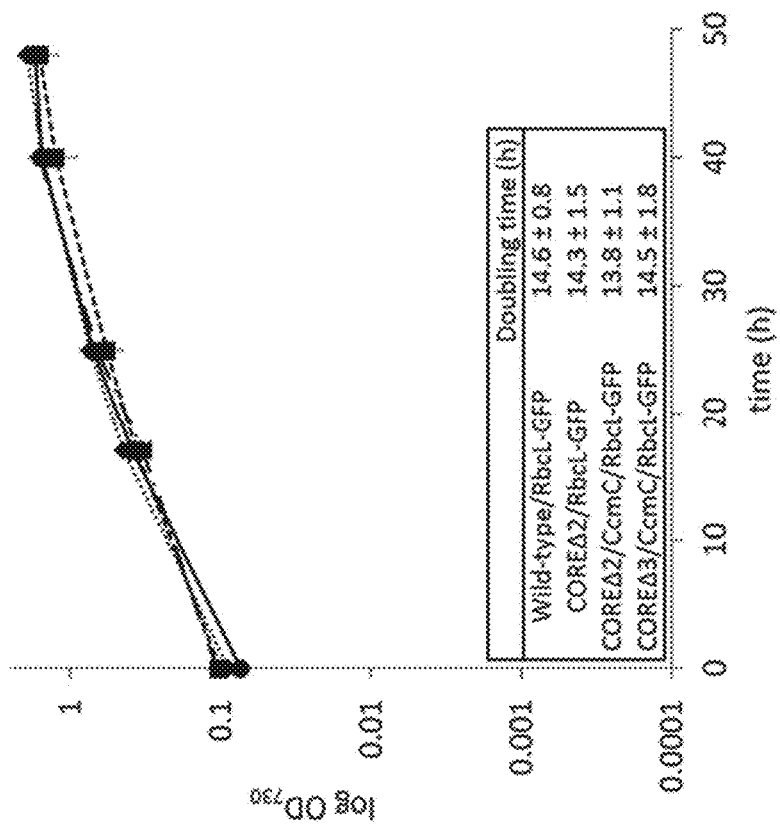
FIG. 5A-5B illustrate growth of CcmC strains compared to wild type showing that functional complementation has occurred of the carboxysome core deletion by the chimeric protein, CcmC.
Figure 5A:
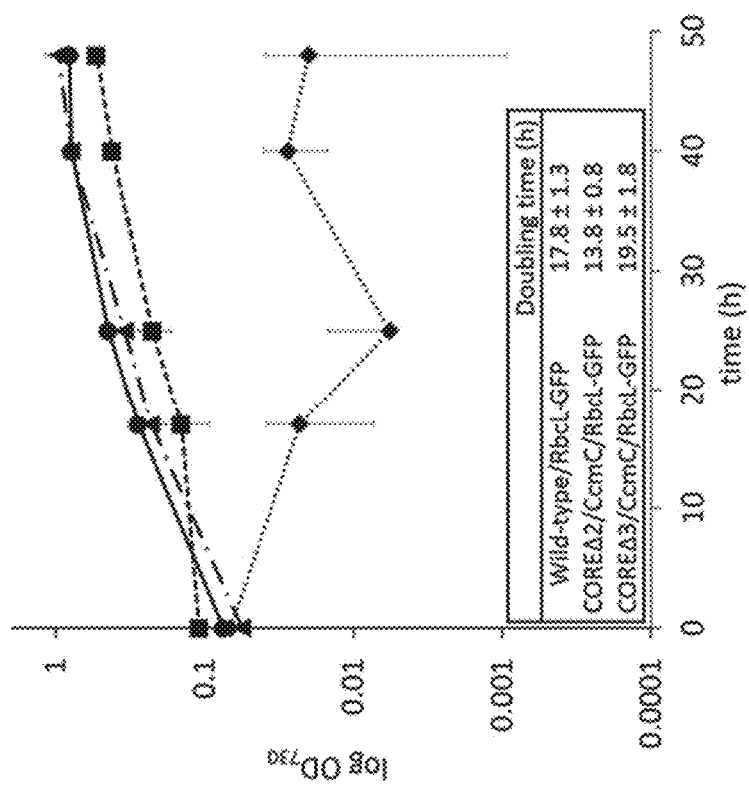

The chimeric CcmC carboxysomes, although smaller, morphologically resemble wild-type carboxysomes (FIG. 3) and they are able to support photosynthesis (FIG. 5A-5B). The results provided herein demonstrate that at least four protein domains can be combined into one, and that a non-native fusion protein can be enclosed in carboxysome shells by including a single encapsulating domain (the EP) as part of the chimeric CcmC protein.

Carboxysomes

Bacterial microcompartments (BMCs) are a family of architecturally similar but functionally diverse self-assembling organelles composed entirely of protein (Axen et al., 2014; Kerfeld and Erbilgin, 2015). The first BMC identified was the carboxysome (Drews and Niklowitz, 1956). Carboxysomes are about 300 MDa in size. Carboxysomes form compartments (Cheng et al., 2008) that are part of the cyanobacterial carbon concentrating mechanism (ccm) that enhance carbon fixation by sequestering ribulose-1,5-bisphosphate carboxylase/oxygenase (Rubisco) and carbonic anhydrase (CA) within a protein shell. In the carboxysome lumen, bicarbonate is converted into carbon dioxide by a carbonic anhydrase (CA), which increases the proportion of carbon dioxide to oxygen in the vicinity of Rubisco while the carboxysome shell limits the loss of carbon dioxide into the bulk cytosol (Cai et. al, 2009). Such increased concentration of carbon dioxide favors Rubisco's carboxylase activity. The product of carbon fixation, 3-phosphoglycerate (3-PGA), exits the carboxysome and can be used in the Calvin cycle or other biosynthetic pathways. Rubisco is the most abundant protein in the biosphere and is responsible for the majority of Earth's primary production of biomass.

Two types of carboxysomes are found in cyanobacteria: α-carboxysomes containing form 1A Rubisco, and β-carboxysomes containing form 1B Rubisco. The constituent core proteins also differ between the two types of carboxysomes, as well as the mode of assembly. Recently it was proposed that a large, conserved multi-domain protein (CsoS2) organizes the Rubisco in the α-carboxysome core (Cai et al., 2015). In contrast, assembly of the β-carboxysome involves a sequence of protein domain interactions among multiple core proteins (Cameron et al., 2013).

Figure 1G:
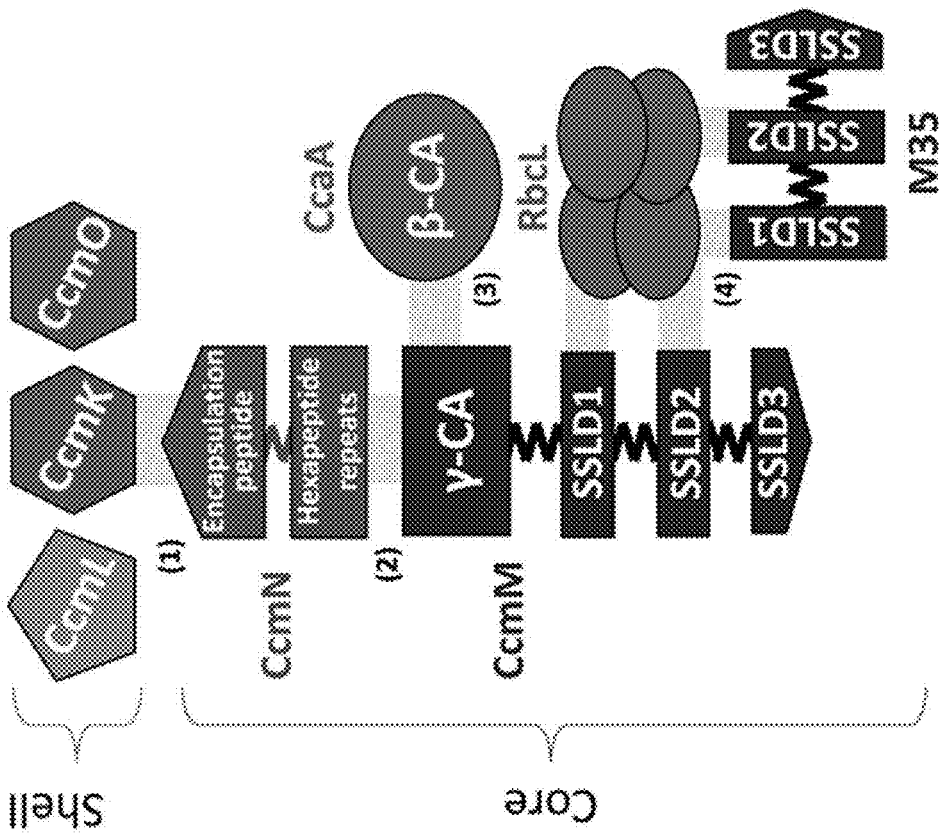

In *Synechococcus elongatus* PCC 7942, the β-carboxysome shell is formed by the structural proteins CcmK, CcmL and CcmO. The core of native carboxysomes is composed of CcmM, M35 and CcmN as well as the enzymes Rubisco (form 1B) and the β-carbonic anhydrase, CcaA (FIG. 1G).

CcmM Protein

The carbon dioxide concentrating mechanism protein, CcmM, can exist as 58-kDa and 35-kDa protein products in *Synechococcus elongatus* PCC 7942. The relative composition of the 58-kDa and 35-kDa CcmM proteins is not affected by protease inhibitors. FIG. 1A shows a schematic diagram of the CcmM protein.

An amino acid sequence for a *Synechococcus elongatus* PCC 7942 carbonate dehydratase (CcmM: Synpcc7942_1423; 57833 daltons) is available as accession number ABB57453 (see website at uniprot.org/uniprot/Q03513)(SEQ ID NO:1).

```
  1 MPSPTTVPVA TAGRLAEPYI DPAAQVHAIA SIIGDVRIAA

41 GVRVAAGVSI RADEGAPFQV GKESILQEGA VIHGLEYGRV

81 LGDDQADYSV WIGQRVAITH KALIHGPAYL GDDCFVGFRS

121 TVFNARVGAG SVIMMHALVQ DVEIPPGRYV PSGAIITTQQ

161 QADRLPEVRP EDREFARHII GSPPVIVRST PAATADFHST

201 PTPSPLRPSS SEATTVSAYN GQGRLSSEVI TQVRSLLNQG

241 YRIGTEHADK RRFRTSSWQP CAPIQSTNER QVLSELENCL

281 SEHEGEYVRL LGIDTNTRSR VFEALIQRPD GSVPESLGSQ

321 PVAVASGGGR QSSYASVSGN LSAEVVNKVR NLLAQGYRIG

361 TEHADKRRFR TSSWQSCAPI QSSNERQVLA ELENCLSEHE

401 GEYVRLLGID TASRSRVFEA LIQDPQGPVG SAKAAAAPVS

441 SATPSSHSYT SNGSSSSDVA GQVRGLLAQG YRISAEVADK

481 RRFQTSSWQS LPALSGQSEA TVLPALESIL QEHKGKYVRL

521 IGIDPAARRR VAELLIQKP
```

A related CcmM protein from *Synechococcus elongatus* has a sequence has at least 99% sequence identity to SEQ ID NO:1, as illustrated below (SEQ ID NO:2).

```
99.8% identity in 539 residues overlap; Score: 2722.0;
Gap frequency: 0.0%
Seq1    1 MPSPTTVPVATAGRLAEPYIDPAAQVHAIASIIGDVRIAAGVRVAAGVSIRADEGAPFQV
Seq2    1 MPSPTTVPVATAGRLAEPYIDPAAQVHAIASIIGDVRIAAGVRVAAGVSIRADEGAPFQV
          ************************************************************

Seq1   61 GKESILQEGAVIHGLEYGRVLGDDQADYSVWIGQRVAITHKALIHGPAYLGDDCFVGFRS
Seq2   61 GKESILQEGAVIHGLEYGRVLGDDQADYSVWIGQRVAITHKALIHGPAYLGDDCFVGFRS
          ************************************************************
```

```
Seq1 121 TVFNARVGAGSVIMMHALVQDVEIPPGRYVPSGAIITTQQQADRLPEVRPEDREFARHII
Seq2 121 TVFNARVGAGSVIMMHALVQDVEIPPGRYVPSGAIITTQQQADRLPEVRPEDREFARHII
         ************************************************************

Seq1 181 GSPPVIVRSTPAATADFHSTPTPSPLRPSSSEATTVSAYNGQGRLSSEVITQVRSLLNQG
Seq2 181 GSPPVIVRSTPAATADFHSTPTPSPLRPSSSEATTVSAYNGQGRLSSEVITQVRSLLNQG
         ************************************************************

Seq1 241 YRIGTEHADKRRFRTSSWQPCAPIQSTNERQVLSELENCLSEHEGEYVRLLGIDTNTRSR
Seq2 241 YRIGTEHADKRRFRTSSWQPCAPIQSTNERQVLSELENCLSEHEGEYVRLLGIDTNTRSR
         ************************************************************

Seq1 301 VFEALIQRPDGSVPESLGSQPVAVASGGGRQSSYASVSGNLSAEVVNKVRNLLAQGYRIG
Seq2 301 VFEALIQRPDGSVPESLGSQPVAVASGGGRQSSYASVSGNLSAEVVNKVRNLLAQGYRIG
         ************************************************************

Seq1 361 TEHADKRRFRTSSWQSCAPIQSSNERQVLAELENCLSEHEGEYVRLLGIDTASRSRVFEA
Seq2 361 TEHADKRRFRTSSWQSCAPIQSSNERQVLAELENCLSEHEGEYVRLLGIDTASRSRVFEA
         ************************************************************

Seq1 421 LIQDPQGPVGSAKAAAAPVSSATPSSHSYTSNGSSSSDVAGQVRGLLAQGYRISAEVADK
Seq2 421 LIQDPQGPVGSAKAAAAPVSSATPSSHSYTSNGSSSSDVAGQVRGLLAQGYRISAEVADK
         ************************************************************

Seq1 481 RRFQTSSWQSLPALSGQSEATVLPALESILQEHKGKYVRLIGIDPAARRRVAELLIQKP
Seq2 481 RRFQTSSWQSLPALSGRSEATVLPALESILQEHKGKYVRLIGIDPAARRRVAELLIQKP
         *************** *******************************************
```

This related protein has a sequence that is available from the National Center for Biotechnology Information database (see website at ncbi.nlm.nih.gov) with accession number WP_011242447.1 (GI:499561664), and with the sequence shown below (SEQ ID NO:2)

```
  1 MPSPTTVPVA TAGRLAEPYI DPAAQVHAIA SIIGDVRIAA

41 GVRVAAGVSI RADEGAPFQV GKESILQEGA VIHGLEYGRV

81 LGDDQADYSV WIGQRVAITH KALIHGPAYL GDDCFVGFRS

121 TVFNARVGAG SVIMMHALVQ DVEIPPGRYV PSGAIITTQQ

161 QADRLPEVRP EDREFARHII GSPPVIVRST PAATADFHST

201 PTPSPLRPSS SEATTVSAYN GQGRLSSEVI TQVRSLLNQG

241 YRIGTEHADK RRFRTSSWQP CAPIQSTNER QVLSELENCL

281 SEHEGEYVRL LGIDTNTRSR VFEALIQRPD GSVPESLGSQ

321 PVAVASGGGR QSSYASVSGN LSAEVVNKVR NLLAQGYRIG

361 TEHADKRRFR TSSWQSCAPI QSSNERQVLA ELENCLSEHE

401 GEYVRLLGID TASRSRVFEA LIQDPQGPVG SAKAAAAPVS

441 SATPSSHSYT SNGSSSSDVA GQVRGLLAQG YRISAEVADK

481 RRFQTSSWQS LPALSGRSEA TVLPALESIL QEHKGKYVRL

521 IGIDPAARRR VAELLIQKP
```

A related CcmM protein from *Prochlorothrix hollandica* has a sequence has at least 53% sequence identity to SEQ ID NO:1, as illustrated below (SEQ ID NO:3).

```
51.5% identity in 563 residues overlap; Score: 1331.0;
Gap frequency: 4.8%
Seq1   3 SPTTVPVATAGRLAEPYIDPAAQVHAIASIIGDVRIAAGVRVAAGVSIRADEGAPFQVGK
Seq3   5 SSAAPPTPWSRGLAEPQIDGSAYVHAFSNVIGDVWIGENVLIAPGTSIRADEGAPFHIGS
           *    *    **** **  * ***    **** *   *  * ********** *

Seq1  63 ESILQEGAVIHGLEYGRVLGDDQADYSVWIGQRVAITHKALIHGPAYLGDDCFVGFRSTV
Seq3  65 STNIQDGVVIHGLEQGRVLGDDQKEYSVWVGRDSSLTHKALIHGPAYVGDECFIGFRSTV
         *  * ****** ******** *** ** *           ***********  ** ** ** ******

Seq1 123 FNARVGAGSVIMMHALVQDVEIPPGRYVPSGAIITTQQQADRLPEVRPEDREFARHIIGS
Seq3 125 FNARVGHGCIVMMHALIQDVEIPPGKYVPSGAIITSQQQADRLPDVRQEDKDFAHHVVGI
         ****** *  ******* ******** ******** *******  ** ** ** **  *

Seq1 183 PPVIVRSTPAATADFHSTPTPSPLRPSSSEAT------------TVSAYNGQGRLSSEVI
Seq3 185 NEALLAGYHCARSSACINPIRAGLSQTFQGSTPGTHGLEESINGTTNTMNNGYGLSPALI
             *       *       *       *       *          *      *   **  *

Seq1 231 TQVRSLLNQGYRIGTEHADKRRFRTSSWQPCAPIQSTNERQVLSELENCLSEHEGEYVRL
Seq3 245 SQVRSLLAQGYRIGTEHATPRRFKTSSWESCAPIESKNEGQVLSALSGCLQEHQGEYVRL
         ****** ********** *** ****  ****     ****** ****   * ** ** ******

Seq1 291 LGIDTNTRSRVFEALIQRPDGSVPE--SLGSQPVAVASGGGRQSSYASVSGNLSAEVVNK
Seq3 305 LGIDVQARRRVLEVLIQRPDGKPTSLSTRGTVSVAAPSASNGHRSSTAGTSNGGGSLADQ
         ****    * ** * *******       **  *        *   **
```

-continued
```
Seq1  349 VRNLLAQGYRIGTEHADKRRFRTSSWQSCAPIQSSNERQVLAELENCLSEHEGEYVRLLG
Seq3  365 VRGLLQQGCRITTEHADKRRFKTSSWQVGAVIESSNFNQVMAALDSAMQQYSGEYVRLIA
          ** ** ** ** ********* *****  * * ***  ** *        ******

Seq1  409 IDTASRSRVFEALIQDPQGPVGSAKAAAAPVSSATPSSHSYTSNGSSSS----------
Seq3  425 VDPLAKRRVAEVLIHRPDGKPVATTAASKGSTYSSNGASNGASNGASSNGYGGGSVSGLS
           *     ** * **   *  *      **             *** **

Seq1  458 -DVAGQVRGLLAQGYRISAEVADKRRFQTSSWQSLPALSGQSEATVLPALESILQEHKGK
Seq3  485 GETANQVRGWLGQGYRISAEYADKRRFKTGSWQTHGTLEGRGDQ-VLGSISTVLSTHSGN
           * **** * ******** ****** *  ***     *   *  **    *  *  *

Seq1  517 YVRLIGIDPAARRRVAELLIQKP
Seq3  544 YVRLVGVDPQAKRRVGQVIIQRP
          **** * ** * ***    ** *
```

This related CcmM protein from *Prochlorothrix hollandica* has a sequence that is available from the National Center for Biotechnology Information database (see website at ncbi.nlm.nih.gov) with accession number WP_017713783.1 (GI: 516317089), and with the sequence shown below (SEQ ID NO:3).

```
  1 MAGYSSAAPP TPWSRGLAEP QIDGSAYVHA FSNVIGDVWI
 41 GENVLIAPGT SIRADEGAPF HIGSSTNIQD GVVIHGLEQG
 81 RVLGDDQKEY SVWVGRDSSL THKALIHGPA YVGDECFIGF
121 RSTVFNARVG HGCIVMMHAL IQDVEIPPGK YVPSGAIITS
161 QQQADRLPDV RQEDKDFAHH VVGINEALLA GYHCARSSAC
201 INPIRAGLSQ TFQGSTPGTH GLEESINGTT NTMNNGYGLS
241 PALISQVRSL LAQGYRIGTE HATPRRFKTS SWESCAPIES
281 KNEGQVLSAL SGCLQEHQGE YVRLLGIDVQ ARRRVLEVLI
321 QRPDGKPTSL STRGTVSVAA PSASNGHRSS TAGTSNGGGS
361 LADQVRGLLQ QGCRITTEHA DKRRFKTSSW QVGAVIESSN
401 FNQVMAALDS AMQQYSGEYV RLIAVDPLAK RRVAEVLIHR
441 PDGKPVATTA ASKGSTYSSN GASNGASNGA SSNGYGGGSV
481 SGLSGETANQ VRGWLGQGYR ISAEYADKRR FKTGSWQTHG
521 TLEGRGDQVL GSISTVLSTH SGNYVRLVGV DPQAKRRVGQ
561 VIIQRP
```

A related CcmM protein from *Hassallia byssoidea* has a sequence has at least 53% sequence identity to SEQ ID NO:1, as illustrated below. Asterisks below the compared sequences indicate amino acid identity at that position (SEQ ID NO:4).

```
52.5% identity in 541 residues overlap; Score: 1402.0;
Gap frequency: 1.1%
Seq1    3 SPTTVPVATAGRLAEPYIDPAAQVHAIASIIGDVRIAAGVRVAAGVSIRADEGAPFQVGK
Seq4    5 STAAPPTPWSRNLAEPNIDATAYIHPFSNVIGDVRIGANVIVAPGTSIRADEGTPFNISE
           *    *     ****  ** * *       ****** *  * ** * ********  **

Seq1   63 ESILQEGAVIHGLEYGRVLGDDQADYSVWIGQRVAITHKALIHGPAYLGDDCFVGFRSTV
Seq4   65 NTNLQDGVVIHGLEQGRVIGDDDNQYSVWIGKNASITHMALIHGPAYVGDDCFIGFRSTV
           * * * ******  *** ***   ******    *** ******* **** ******

Seq1  123 FNARVGAGSVIMMHALVQDVEIPPGRYVPSGAIITTQQQADRLPEVRPEDREFARHIIGS
Seq4  125 FNARVGNGCIVMMHALIQDVEIPPGKYVPSGAIITNQQQADRLPDVQVQDREFSHHVVGI
          ****** *  ****** ******** ********* *********  *  ****   *

Seq1  183 PPVIVRSTPAATADFHSTPTPSPLRPSSSEATTVSAYNGQG----RLSSEVITQVRSLLN
Seq4  185 NQAL-RSGYLCAADNKCIKNIRNEMTSSYKTNGSNGYSGNGSVSSNLSSETVQQVRHLLE
              ** **       *                              ****   ** **

Seq1  239 QGYRIGTEHADKRRFRTSSWQPCAPIQSTNERQVLSELENCLSEHEGEYVRLLGIDTNTR
Seq4  244 QGYYQIGTEHVDQRRFRTGSWASCSPIATNSTSEAIAALESCLAEHSGEFVRLFGIDPKGK
          ***  ***** * ***** **   ** **    *     * ** *** *** ***  *

Seq1  299 SRVFEALIQRPDGSVPESLGSQPVAVASGGGRQSSYASVSGNLSAEVVNKVRNLLAQGYR
Seq4  304 RRVLETIIQRPDGVVQNGT-TPKLGVKSASYSGGNSYSGSSTLSGEAIEQVRQLLAGGYK
           **    ******        *     *        * **  **  * **** ** **

Seq1  359 IGTEHADKRRFRTSSWQSCAPIQSSNERQVLAELENCLSEHEGEYVRLLGIDTASRSRVF
Seq4  363 IGMEHVDKRRFRTGSWQSCTPIASSNEKEVISALEACVASHTGEYVRLVGIEPKARKRVL
          ** ** ******* ***** ** ****     **  *  * ****** **     **

Seq1  419 EALIQDPQGPVGSAKAAAAPVSSATPSSHSYTSNGSSSSDVAGQVRGLLAQGYRISAEVA
Seq4  423 ESIIQRPDGNVAEGSSNKFVASSSESRTSTNASTRLSPEVIDQLRQLINQGSKISAEHV
          * **  * *       ** ***      **  *      *   *  * ** ****
```

```
-continued
Seq1  479 DKRRFQTSSWQSLPALSGQSEATVLPALESILQEHKGKYVRLIGIDPAARRRVAELLIQK
Seq4  483 DKRRFRTGSWASCGQIQGNSEREAIAALEGYLREYQGEYVRLIGIEPKAKKRVLESIIQR
          *****  *  **  *       *  **       ***  *  *  *******  *  ** *  **

Seq1  539 P
Seq4  543 P
          *
```

This related CcmM protein from *Hassallia byssoidea* has a sequence that is available from the National Center for Biotechnology Information database (see website at ncbi.nlm.nih.gov) with accession number WP_039748670.1 (GI: 748175120), and with the sequence shown below (SEQ ID NO:4).

```
  1 MAVRSTAAPP TPWSRNLAEP NIDATAYIHP FSNVIGDVRI

41 GANVIVAPGT SIRADEGTPF NISENTNLQD GVVIHGLEQG

81 RVIGDDDNQY SVWIGKNASI THMALIHGPA YVGDDCFIGF

121 RSTVFNARVG NGCIVMMHAL IQDVEIPPGK YVPSGAIITN

161 QQQADRLPDV QVQDREFSHH VVGINQALRS GYLCAADNKC

201 IKNIRNEMTS SYKTNGSNGY SGNGSVSSNL SSETVQQVRH

241 LLEQGYQIGT EHVDQRRFRT GSWASCSPIA TNSTSEAIAA

281 LESCLAEHSG EFVRLFGIDP KGKRRVLETI IQRPDGVVQN

321 GTTPKLGVKS ASYSGGNSYS GSSTLSGEAI EQVRQLLAGG

361 YKIGMEHVDK RRFRTGSWQS CTPIASSNEK EVISALEACV

401 ASHTGEYVRL VGIEPKARKR VLESIIQRPD GNVAEGSSNK

441 FVASSSSESR TSTNASTRLS PEVIDQLRQL INQGSKISAE

481 HVDKRRFRTG SWASCGQIQG NSEREAIAAL EGYLREYQGE

521 YVRLIGIEPK AKKRVLESII QRPDDSVAQS SRSDNQVVAS

561 SSSSTSKTSN TATSTRLSSE VVDQLRQLRN QGSKISVEHV

601 DQRRFRTGSW TSGGQIQGNS EREAIAALEG YLREYEGEYV

641 RLIGINPKDK RRVLETIIQR P
```

CcmM comprises an N-terminal γ-CA domain followed by three small subunit-like domains (SSLDs) with sequence homology to RbcS, the small subunit of Rubisco (Long et al., 2007).

M35 Protein

The ccmM gene encodes two essential carboxysome components, the full-length protein and a truncated form containing only the SSLDs (known as M35 in *Synechococcus elongatus* PCC 7942). In *Synechococcus*, the short form is composed of three SSLDs, which are believed to aggregate Rubisco. An amino acid sequence for the CcmM short form from *Synechococcus elongatus* PCC 7942 is shown below as SEQ ID NO:5, where the SSLD domains are identified in bold and with underlining.

```
215     TVSAYN GQGRLSSEVI TQVRSLLNQG YRIGTEHADK

251 RRFRTSSWQP CAPIQSTNER QVLSELENCL SEHEGEYVRL

291 LGIDTNTRSR VFEALIQRPD GSVPESLGSQ PVAVASGGGR

331 QSSYASVSGN LSAEVVNKVR NLLAQGYRIG TEHADKRRFR

371 TSSWQSCAPI QSSNERQVLA ELENCLSEHE GEYVRLLGID

411 TASRSRVFEA LIQDPQGPVG SAKAAAAPVS SATPSSHSYT

451 SNGSSSSDVA GQVRGLLAQG YRISAEVADK RRFQTSSWQS

491 LPALSGQSEA TVLPALESIL QEHKGKYVRL IGIDPAARRR

531 VAELLIQKP
```

As illustrated, an SSLD can include any of SEQ ID NOs: 75-77.

```
                                              (SEQ ID NO: 75)
215     TVSAYN GQGRLSSEVI TQVRSLLNQG YRIGTEHADK

251 RRFRTSSWQP CAPIQSTNER QVLSELENCL SEHEGEYVRL

291 LGIDTNTRSR VFEALIQRP
```

```
                                              (SEQ ID NO: 76)
331         SAEVVNKVR NLLAQGYRIG TEHADKRRFR

371 TSSWQSCAPI QSSNERQVLA ELENCLSEHE GEYVRLLGID

411 TASRSRVFEA LIQDP
```

```
                                              (SEQ ID NO: 77)
451     SSSDVA GQVRGLLAQG YRISAEVADK RRFQTSSWQS

491 LPALSGQSEA TVLPALESIL QEHKGKYVRL IGIDPAARRR

531 VAELLIQKP
```

Some forms of M35 in other cyanobacteria (also referred to as a short form CcmM) can have more SSLDs and can be of varying lengths. Some forms of M35 can have a few amino acids missing from the N-terminus or the C-terminus when compared to the *Synechococcus elongatus* PCC 7942 M35 protein. For example, there can be one, or two, or three, or four, or five, or six, or seven, or eight, or nine, or ten few amino acids missing from the N-terminus or the C-terminus of some forms of M35 when compared to the *Synechococcus elongatus* PCC 7942 M35 protein. In addition, the N-terminus of M35 proteins can have a methionine.

A related short form CcmM protein from *Acaryochloris marina* has a sequence has at least 56% sequence identity to SEQ ID NO:5, as illustrated below (where the SEQ ID NO:5 sequence is the Query protein).

57.1% identity in 326 residues overlap; Score: 877.0; Gap frequency: 4.0%

```
Seq5   11 LSSEVITQVRSLLNQGYRIGTEHADKRRFRTSSWQPCAPIQSTNERQVLSELENCLSEHE
Seq6  228 LDAAIVSQVRSLLAQGYRIGSEHADKRRFQTSSWQSCPSITSTNESQVLAGIESCMSEHQ
          *     ****** ****** ******** *****  *  * **** ***   * * ***

Seq5   71 GEYVRLLGIDTNTRSRVFEALIQRPDGSVPESLGSQPVAVASGGGRQSSYASVSGNLSAE
Seq6  288 GEYVRLIGIDTQARQRVLETIIQRPDGPVKSASISSVTKTIK--NYTTSHISSSGNIDAE
          ****** ****  *  * **  ****** *              *  * *** **

Seq5  131 VVNKVRNLLAQGYRIGTEHADKRRFRTSSWQSCAPIQSSNERQVLAELENCLSEHEGEYV
Seq6  346 TIAHVRSLLGQGYRIGTEHADARRFQTSSWQSCSPIASQQESQVVAALEACIVEHQGEYV
             ** ** *********** *** ******* ** *  * ** *  ** *  ** ****

Seq5  191 RLLGIDTASRSRVFEALIQDPQGPVGSAKAAAAPVSSATPSSH----SYTSNGSSS----
Seq6  406 RMLGIDTQAKQRVFEAIIQRPSDKPKAAPKASRPASTSSSSSSYASPSYASSSPNSGTST
          * *****     ***** **  *   *     *      **      **  *

Seq5  243 ---SDVAGQVRGLLAQGYRISAEVADKRRFQTSSWQSLPALSGQSEATVLPALESILQEH
Seq6  466 GLGADAIAQVRSLLAQGYRVGYEYADKRRFQTSSWQSCTPINSQQESQVIAALESCIAEH
             *   ********   *  ************    *   *   *  *****   **

Seq5  300 KGKYVRLIGIDPAARRRVAELLIQKP
Seq6  526 PGNYVRLIGIDPKAKRRVLEVIIQRP
            * ********  * *** *  ** *
```

This related protein from *Acaryochloris marina* has a sequence that is available from the National Center for Biotechnology Information database (see website at ncbi.nlm.nih.gov) with accession number WP_012165581.1 (GI: 501116295), and with the full length sequence shown below (SEQ ID NO:6).

```
  1 MVIHSPSTSA SMQAGNLPDP RVSSSAYVHS FAKVMGDVHV
 41 GANALIAPGS TIQADQGLPF HIGDNVNIQD GAVIHAIEPG
 81 QVRGKDGQNY AVWIGNNSCV THMALIHGPA FIGDNCFIGF
121 RSTVFNAKVG DNCVIMMHAL IQGVEIPPGK YVPSGAVITK
161 QEQANLLPDV LESDRKFTQQ IIHVNEALKS EISGASTKTS
201 IRPARANIGH SQSHRFTTDT KPMNHTTLDA AIVSQVRSLL
241 AQGYRIGSEH ADKRRFQTSS WQSCPSITST NESQVLAGIE
281 SCMSEHQGEY VRLIGIDTQA RQRVLETIIQ RPDGPVKSAS
321 ISSVTKTIKN YTTSHISSSG NIDAETIAHV RSLLGQGYRI
361 GTEHADARRF QTSSWQSCSP IASQQESQVV AALEACIVEH
401 QGEYVRMLGI DTQAKQRVFE AIIQRPSDKP KAAPKASRPA
441 STSSSSSSYA SPSYASSSPN SGTSTGLGAD AIAQVRSLLA
481 QGYRVGYEYA DKRRFQTSSW QSCTPINSQQ ESQVIAALES
521 CIAEHPGNYV RLIGIDPKAK RRVLEVIIQR PDSNSKASPS
561 APKARPASSS SSYSSKVESN SSSYRPAPSA GLDGTVVNQI
601 RSLLAQGYRI GTEYADKRRF QTSSWQSCTP IASQQESQVI
641 AGVEACMAEH PNDYVRLIGI DKRAKRRMSE TIIQRPGGST
681 ATSSSVKTSS SRSYQAPAAK SSRGRGFSPR NGGSLDADTV
721 AQVRSLLAQG YRISTEYADK RRFQTSSWQS CPPIKTQQES
761 QVIAALESCM ADHQKEYVRL IGIDTNAKRR VLESVIQKPV
801 AAH
```

The short form CcmM portion of this *Acaryochloris marina* related protein contains five SSLDs and is shown below as SEQ ID NO:7.

```
        KPMNHTTLDA AIVSQVRSLL
241 AQGYRIGSEH ADKRRFQTSS WQSCPSITST NESQVLAGIE
281 SCMSEHQGEY VRLIGIDTQA RQRVLETIIQ RPDGPVKSAS
321 ISSVTKTIKN YTTSHISSSG NIDAETIAHV RSLLGQGYRI
361 GTEHADARRF QTSSWQSCSP IASQQESQVV AALEACIVEH
401 QGEYVRMLGI DTQAKQRVFE AIIQRPSDKP KAAPKASRPA
441 STSSSSSSYA SPSYASSSPN SGTSTGLGAD AIAQVRSLLA
481 QGYRVGYEYA DKRRFQTSSW QSCTPINSQQ ESQVIAALES
521 CIAEHPGNYV RLIGIDPKAK RRVLEVIIQR PDSNSKASPS
561 APKARPASSS SSYSSKVESN SSSYRPAPSA GLDGTVVNQI
601 RSLLAQGYRI GTEYADKRRF QTSSWQSCTP IASQQESQVI
641 AGVEACMAEH PNDYVRLIGI DKRAKRRMSE TIIQRPGGST
681 ATSSSVKTSS SRSYQAPAAK SSRGRGFSPR NGGSLDADTV
721 AQVRSLLAQG YRISTEYADK RRFQTSSWQS CPPIKTQQES
761 QVIAALESCM ADHQKEYVRL IGIDTNAKRR VLESVIQKPV
801 AAH
```

Some forms of CcmM can have a few amino acids missing from the N-terminus or the C-terminus of the short form CcmM protein. In addition, the N-terminus of the short form CcmM protein can have a methionine.

A related short form CcmM protein from *Thermosynechococcus elongatus* BP-1 has a sequence has at least 49% sequence identity to SEQ ID NO:5, as illustrated below.

```
48.1% identity in 316 residues overlap; Score: 685.0; Gap frequency:
3.8%
Seq5    11 LSSEVITQVRSLLNQGYRIGTEHADKRRFRTSSWQPCAPIQSTNERQVLSELENCLSEHE
Seq8   229 MTTDYGTHVRQLLQQGYQISLEYADARRYRTSSWQSGPTLTGQQESQVMAAIAQLLKEHE
              *  **  **  ***   *   *  **  **  ******       * **         * ***

Seq5    71 GEYVRLLGIDTNTRSRVFEALIQRP-DGSVPESLGSQPVAVASGGGRQSSYASVSGNLSA
Seq8   289 GEYVRLIGVDPKAKRRVFEEIIQRPGQAAVASSSSSRPSATVN--------ASPVGSLDA
              ****** * *      ****  ****    *  *  * * *                    **   *  *

Seq5   130 EVVNKVRNLLAQGYRIGTEHADKRRFRTSSWQSCAPIQSSNERQVLAELENCLSEHEGEY
Seq8   341 AVVAQVRQLLQQGYQIGTEHADARRYRTSSWTSCAPIQSKQEPEVLAALEACLQEHAGEY
              **  **  ** ***  *******  ** *****  ******* *    *** **  ** **  ***

Seq5   190 VRLLGIDTASRSRVFEALIQDPQGPVGSAKAAAAPVSSATPSSHSYTSNGSSSSDVAGQV
Seq8   401 VRLIGIDQKQKRRVLEQIIQRPQGPVAIAPKTPTPVATSHASVSSGGNDTLLSADLVNQI
              *** ***       ** *   ** *****       **              *  *              ** *    *

Seq5   250 RGLLAQGYRISAEVADKRRFQTSSWQSLPALSGQSEATVLPALESILQEHKGKYVRLIGI
Seq8   461 QDLLRQGCQVITEYADQRRFRTSSWQSGIKITSAQQ---INDLRSFLAEHQRDYIRLVGV
                ** **     *  ** ***  ******           *  *  **      *  **    *

Seq5   310 DPAARRRVAELLIQKP
Seq8   518 NPQAKQRVLETIIHRP
              *  *   ** *    *   *
```

This related protein from *Thermosynechococcus elongatus* BP-1 has a sequence that is available from the National Center for Biotechnology Information database (see website at ncbi.nlm.nih.gov) with accession number NP_681734.1 (GI:22298487) and with the sequence shown below (SEQ ID NO:8).

```
  1 MAVQSYAAPP TPWSRDLAEP EIAPTAYVHS FSNLIGDVRI
 41 KDYVHIAPGT SIRADEGTPF HIGSRTNIQD GVVIHGLQQG
 81 RVIGDDGQEY SVWIGDNVSI THMALIHGPA YIGDGCFIGF
121 RSTVFNARVG AGCVVMMHVL IQDVEIPPGK YVPSGMVITT
161 QQQADRLPNV EESDIHFAQH VVGINEALLS GYQCAENIAC
201 IAPIRNELQR QEDPPTLHVE MLTGEKNTMT TDYGTHVRQL
241 LQQGYQISLE YADARRYRTS SWQSGPTLTG QQESQVMAAI
281 AQLLKEHEGE YVRLIGVDPK AKRRVFEEII QRPGQAAVAS
321 SSSSRPSATV NASPVGSLDA AVVAQVRQLL QQGYQIGTEH
361 ADARRYRTSS WTSCAPIQSK QEPEVLAALE ACLQEHAGEY
401 VRLIGIDQKQ KRRVLEQIIQ RPQGPVAIAP KTPTPVATSH
441 ASVSSGGNDT LLSADLVNQI QDLLRQGCQV ITEYADQRRF
481 RTSSWQSGIK ITSAQQINDL RSFLAEHQRD YIRLVGVNPQ
521 AKQRVLETII HRPNGKAASN GNSTRGQGFT PRPTASSQGS
561 PSTHSLSQEV IEQVRQLLQQ GYTLGLEHVD ARRYRTNSWQ
601 SGPRIEAKNL NEALAAIQAC LQEYSGEYVR LIGINPAGKQ
641 RVAEILLQQA AK
```

The short form CcmM portion of this *Thermosynechococcus elongatus* BP-1 related protein has four SSLDS and is shown below as SEQ ID NO:9.

```
201                                            THVRQL
241 LQQGYQISLE YADARRYRTS SWQSGPTLTG QQESQVMAAI
281 AQLLKEHEGE YVRLIGVDPK AKRRVFEEII QRPGQAAVAS
321 SSSSRPSATV NASPVGSLDA AVVAQVRQLL QQGYQIGTEH
361 ADARRYRTSS WTSCAPIQSK QEPEVLAALE ACLQEHAGEY
401 VRLIGIDQKQ KRRVLEQIIQ RPQGPVAIAP KTPTPVATSH
441 ASVSSGGNDT LLSADLVNQI QDLLRQGCQV ITEYADQRRF
481 RTSSWQSGIK ITSAQQINDL RSFLAEHQRD YIRLVGVNPQ
521 AKQRVLETII HRPNGKAASN GNSTRGQGFT PRPTASSQGS
561 PSTHSLSQEV IEQVRQLLQQ GYTLGLEHVD ARRYRTNSWQ
601 SGPRIEAKNL NEALAAIQAC LQEYSGEYVR LIGINPAGKQ
641 RVAEILLQQA AK
```

Some short forms of CcmM can have a few amino acids missing from the N-terminus or the C-terminus of the M35 protein. In addition, the N-terminus of the short form protein can have a methionine.

A related short form CcmM protein from *Trichormus azollae* has a sequence has at least 52% sequence identity to SEQ ID NO:5, as illustrated below.

```
51.1% identity in 321 residues overlap; Score: 798.0; Gap frequency:
1.9%
Seq5     10 RLSSEVITQVRSLLNQGYRIGTEHADKRRFRTSSWQPCAPIQSTNERQVLSELENCLSEH
Seq10   233 KLGAEIVDQVRYLLNQGYKIGTEHVDQRRFRTGSWQSCQPIETRSLGEAITALESCLIDH
                 *  *    ***  ******   *****  ***** ***   *  *  **  **   *       ** **  *
```

```
Seq5    70 EGEYVRLLGIDTNTRSRVFEALIQRPDGSVPESLGSQPVAVAS----GGGRQSSYASVSG
Seq10  293 SGEYVRLFGID-NGRKRVLETIIQRPDGVVATSTSSFKTPAASYSSYNGNGNSNGAVASG
           ****** ***  *  ** *  ****** *   *       **     *   *   * **

Seq5   126 NLSAEVVNKVRNLLAQGYRIGTEHADKRRFRTSSWQSCAPIQSSNERQVLAELENCLSEH
Seq10  352 SLSAETVNQIRQLLANGYKIGTEHVDQRRFRTGSWQSCNPIEATSANDVVAALEECMTSH
           **** **  * *** ** ***** * ***** ***** **  * ** **    *

Seq5   186 EGEYVRLLGIDTASRSRVFEALIQDPQGPVGSAKAAAAPVSSATPSSHSYTSNGSS-SSD
Seq10  412 QGEYVRLIGIDSKAKRRVLEAIIQRPNGQVVSSGSAKTSGTLYSGATASATATSTRLSTE
            ****** ***     ** ** ** * *      *            * *       *

Seq5   245 VAGQVRGLLAQGYRISAEVADKRRFQTSSWQSLPALSGQSEATVLPALESILQEHKGKYV
Seq10  472 VVDQLKQLLTGGFKISVEHVDQRRFRTGSWVSCGQIQATSERDVLAALEAVISEYAGEYV
           *  *  **     *** *  * *** * *** * ** * *  ** *** * ** **

Seq5   305 RLIGIDPAARRRVAELLIQKP
Seq10  532 RLIGIDPVAKRRVLEAIIQRP
           ******* * *** *  ** *
```

This short form CcmM related protein from *Trichormus azollae* has a sequence that is available from the National Center for Biotechnology Information database (see website at ncbi.nlm.nih.gov) with accession number WP_013190978.1 (GI:502956002), and with the sequence shown below (SEQ ID NO:10).

```
  1 MVVRSTAAPP TPWSRSLAEP DIHQTAFVHS SCNLIGDVHL

41 GQNVIIAPGT SIRADEGTPF FIGENTNIQD GVVIHGLEQG

81 RVIGDDGKNY SVWVGKDASI THMALIHGPA YVGESCFIGF

121 RSTVFNARVG AGCIVMMHAL IQDVEIPPGK YVASGSIITM

161 QQQADRLPDV QAQDQQFAHH VVGINQALRA GYRCVEDIKC

201 IAPIRDELNL SGDRSYTSII VDELERSSEV ASKLGAEIVD

241 QVRYLLNQGY KIGTEHVDQR RFRTGSWQSC QPIETRSLGE

281 AITALESCLI DHSGEYVRLF GIDNGRKRVL ETIIQRPDGV

321 VATSTSSFKT PAASYSSYNG NGNSNGAVAS GSLSAETVNQ

361 IRQLLANGYK IGTEHVDQRR FRTGSWQSCN PIEATSANDV

401 VAALEECMTS HQGEYVRLIG IDSKAKRRVL EAIIQRPNGQ

441 VVSSGSAKTS GTLYSGATAS ATATSTRLST EVVDQLKQLL

481 TGGFKISVEH VDQRRFRTGS WVSCGQIQAT SERDVLAALE

521 AVISEYAGEY VRLIGIDPVA KRRVLEAIIQ RP
```

The short form portion of this *Trichormus azollae* related protein contains three SSLDs and is shown below as SEQ ID NO:11.

```
233                                  V ASKLGAEIVD

241 QVRYLLNQGY KIGTEHVDQR RFRTGSWQSC QPIETRSLGE

281 AITALESCLI DHSGEYVRLF GIDNGRKRVL ETIIQRPDGV

321 VATSTSSFKT PAASYSSYNG NGNSNGAVAS GSLSAETVNQ

361 IRQLLANGYK IGTEHVDQRR FRTGSWQSCN PIEATSANDV

401 VAALEECMTS HQGEYVRLIG IDSKAKRRVL EAIIQRPNGQ

441 VVSSGSAKTS GTLYSGATAS ATATSTRLST EVVDQLKQLL

481 TGGFKISVEH VDQRRFRTGS WVSCGQIQAT SERDVLAALE

521 AVISEYAGEY VRLIGIDPVA KRRVLEAIIQ RP
```

Some short forms of CcmM can have a few amino acids missing from the N-terminus or the C-terminus of the protein. In addition, the N-terminus of the short form CcmM protein can have a methionine.

CcmN Protein—Encapsulation Peptide (EP)

CcmN contains multiple hexapeptide-repeats and, at its C-terminus, an encapsulation peptide (EP), which is a short α-helical segment linked to the hexapeptide-repeat domains by a flexible linker sequence (Kinney et al., 2012). In general, encapsulation peptides have poorly conserved sequences but are amphipathic in nature (Aussignargues et al., 2015) A schematic diagram of the CcmN protein is shown in FIG. 1A.

An amino acid sequence for a *Synechococcus elongatus* PCC 7942 carbon dioxide concentrating mechanism protein (CcmN: Synpcc7942_1424) is available as accession number ABB57454 (SEQ ID NO:12).

```
  1 MHLPPLEPPI SDRYFASGEV TIAADVVIAP GVLLIAEADS

41 RIEIASGVCI GLGSVIHARG GAIIIQAGAL LAAGVLIVGQ

81 SIVGRQACLG ASTTLVNTSI EAGGVTAPGS LLSAETPPTT

121 ATVSSSEPAG RSPQSSAIAH PTKVYGKEQF LRMRQSMFPD

161 R
```

As illustrated herein, SSLDs domains are fused with an encapsulation peptide from a CcmN protein. Such an encapsulation peptide can have the following sequence (SEQ ID NO:13).

```
  1            VYGKEQFLRM RQSMFPDR
```

A related CcmN encapsulation peptide is available from *Prochlorothrix hollandica* that has at least 65% sequence identity to SEQ ID NO:13, as illustrated below.

| Score | Expect | Identities | Positives | Gaps |
|---|---|---|---|---|
| 30.8 bits (65) | 0.32 | 11/17 (65%) | 13/17 (76%) | 0/17 (0%) |

```
Seq 13    VYGKEQFLRMRQSMFPD     17
Seq 14    VYGRDYFLQMRFSLFPD    414
          ***  **  ** * ***
```

This *Prochlorothrix hollandica* related encapsulation peptide has the following sequence: VYGRDYFLQMRFSLFPD (SEQ ID NO:14).

A related CcmN encapsulation peptide is available from *Halothece* sp. PCC 7418 (Cai et al, 2016) that has at least 27% sequence identity to SEQ ID NO:13, as illustrated below.

```
Seq13   VYGKEQFLRMRQSMFPDR-------------------------     18
Seq15   IYGQTHIERLMVTLFPHKEKFKKKTNDWFLVLGSLLFDDFPNNE    44
        :**: :: *:   ::**.:
```

The *Halothece* sp. PCC 7418 related encapsulation peptide has the following sequence: IYGQTHIERLMVTLFPH-KEKFKKKTNDWFLVLGSLLFDDFPNNE (SEQ ID NO:15).

A related CcmN encapsulation peptide is available from *Moorea producens* that has at least 56% sequence identity to SEQ ID NO:13, as illustrated below.

| Score | Expect | Identities | Positives | Gaps |
|---|---|---|---|---|
| 28.2 bits (59) | 2.6 | 10/18 (56%) | 12/18 (66%) | 4/18 (22%) |

```
Seq13         EQFLR-MRQSM---FPDR         18
Seq16   606   EQFFRRMRQSLNRAFSER         623
              *** * ****    * *
```

The *Moorea producens* related encapsulation peptide has the following sequence: EQFFRRMRQSLNRAFSER (SEQ ID NO:16).

```
  1 MRKLIEGLRH FRTSYYPSHR DLFEQFAKGQ HPRVLFITCS

41 DSRIDPNLIT QSGMGELFVI RNAGNLIPPF GAANGGEGAS

81 IEYAIAALNI EHVVVCGHSH CGAMKGLLKL NQLQEDMPLV

121 YDWLQHAQAT RRLVLDNYSG YETDDLVEIL VAENVLTQIE

161 NLKTYPIVRS RLFQGKLQIF GWIYEVESGE VLQISRTSSD

201 DTGIDECPVR LPGSQEKAIL GRCVVPLTEE VAVAPPEPEP

241 VIAAVAAPPA NYSSRGWLAP EQQQRIYRGN AS
```

A related CcaA carbonate dehydratase is available from *Synechococcus elongatus* that has at least 99% sequence identity to SEQ ID NO:17, as illustrated below.

```
99.6% identity in 272 residues overlap; Score: 1415.0;
Gap frequency: 0.0%
Seq17    1 MRKLIEGLRHFRTSYYPSHRDLFEQFAKGQHPRVLFITCSDSRIDPNLITQSGMGELFVI
Seq18    1 MRKLIEGLRHFRTSYYPSHRDLFEQFAKGQHPRVLFITCSDSRIDPNLITQSGMGELFVI
           ************************************************************

Seq17   61 RNAGNLIPPFGAANGGEGASIEYAIAALNIEHVVVCGHSHCGAMKGLLKLNQLQEDMPLV
Seq18   61 RNAGNLIPPFGAANGGEGASIEYAIAALNIEHVVVCGHSHCGAMKGLLKLNQLQEDMPLV
           ************************************************************

Seq17  121 YDWLQHAQATRRLVLDNYSGYETDDLVEILVAENVLTQIENLKTYPIVRSRLFQGKLQIF
Seq18  121 YDWLQHAQATRRLVLDNYSGYETDDLVEFLVAENVLTQIENLKTYPIVRSRLFQGKLQIF
           **************************** *******************************

Seq17  181 GWIYEVESGEVLQISRTSSDDTGIDECPVRLPGSQEKAILGRCVVPLTEEVAVAPPEPEP
Seq18  181 GWIYEVESGEVLQISRTSSDDTGIDECPVRLPGSQEKAILGRCVVPLTEEVAVAPPEPEP
           ************************************************************

Seq17  241 VIAAVAAPPANYSSRGWLAPEQQQRIYRGNAS
Seq18  241 VIAAVAAPPANYSSRGWLAPEQQQRIYRGNAS
           ********************************
```

CcaA Carbonate Dehydratase (Carbonic Anhydrase)

While the CcmM and CcmN are typically conserved and are needed for native carboxysome formation (Long et al., 2010; Kinney et al., 2012), CcaA deletion mutant cell lines can still form carboxysomes (So et al., 2002b). Such CcaA deletion mutant cells exhibit a high carbon dioxide-requiring (hcr) phenotype. The CcaA genes encode carbonic anhydrase, also called carbonate dehydratase. A schematic diagram of the carbonate dehydratase, CcaA, protein is shown in FIG. 1A.

An amino acid sequence for a *Synechococcus elongatus* PCC 7942 carbonate dehydratase (CcaA; Synpcc7942_1447; 30185 daltons) is available as accession number ABB57477.1 (see website at uniprot.org/uniprot/P27134)(SEQ ID NO:17).

This CcaA related protein from *Synechococcus elongatus* has a sequence that is available from the National Center for Biotechnology Information database (see website at ncbi.nlm.nih.gov) with accession number WP_011242423.1 (GI: 499561640), and with the sequence shown below (SEQ ID NO:18).

```
  1 MRKLIEGLRH FRTSYYPSHR DLFEQFAKGQ HPRVLFITCS

41 DSRIDPNLIT QSGMGELFVI RNAGNLIPPF GAANGGEGAS

81 IEYAIAALNI EHVVVCGHSH CGAMKGLLKL NQLQEDMPLV

121 YDWLQHAQAT RRLVLDNYSG YETDDLVEFL VAENVLTQIE

161 NLKTYPIVRS RLFQGKLQIF GWIYEVESGE VLQISRTSSD
```

```
201 DTGIDECPVR LPGSQEKAIL GRCVVPLTEE VAVAPPEPEP
241 VIAAVAAPPA NYSSRGWLAP EQQQRIYRGN AS
```

A related CcaA carbonate dehydratase is available from *Geminocystis herdmanii* that has at least 55% sequence identity to SEQ ID NO:17, as illustrated below.

```
58.3% identity in 278 residues overlap; Score: 779.0;
Gap frequency: 2.9%
Seq17    1 MRKLIEGLRHFRTSYYPSHRDLFEQFAKGQHPRVLFITCSDSRIDPNLITQSGMGELFVI
Seq19    1 MKKIIEGLHRFQAGYFESHRDLFEQLSHGQHPRILFITCSDSRIDPNLITQANVGELFVI
           * * ****  *   * ******* ***** ******************      ******

Seq17   61 RNAGNLIPPFGAANGGEGASIEYAIAALNIEHVVVCGHSHCGAMKGLLKLNQLQEDMPLV
Seq19   61 RNAGNIIPPFGATNGGEGASIEYAITALDIEQVIVCGHSHCGAMKGLLKMSKLADKMPLV
           ***** ****** ************ **  * ****************  *    ****

Seq17  121 YDWLQHAQATRRLVLDNYSGYETDDLVEILVAENVLTQIENLKTYPIVRSRLFQGKLQIF
Seq19  121 YEWLKQAEATRRLIIDNYSHLEGEELLQITVAENVLTQLENLNTYPIVRSRLHQGRLSLH
           * ** * ***** ****   *   *  * ******** *** ******** ** * *

Seq17  181 GWIYEVESGEVLQISRTSSDDTGID------ECPVRLPGSQEKAILGRCVVPLTEEVAVA
Seq19  181 GWIYGIETGEVLTYDPKVHDFVNLESRTDNSEYIYNLHPSCSVAKSMFYGIPDENDDKVQ
           ****   * ****        *        *     *    *  *     *       *

Seq17  235 PPEPEPVIAAVAAPPANYSSR--GWLAPEQQQRIYRGN
Seq19  241 PSEPIPQTINPNLPRSRSGAARSNRLSPEQEQRIYRGS
           * **  *       *         * *** ****** *
```

This CcaA related protein from *Geminocystis herdmanii* has a sequence that is available from the National Center for Biotechnology Information database (see website at ncbi.nlm.nih.gov) with accession number WP_017295030.1 (GI: 515864402), and with the sequence shown below (SEQ ID NO:19).

```
  1 MKKIIEGLHR FQAGYFESHR DLFEQLSHGQ HPRILFITCS
 41 DSRIDPNLIT QANVGELFVI RNAGNIIPPF GATNGGEGAS
 81 IEYAITALDI EQVIVCGHSH CGAMKGLLKM SKLADKMPLV
121 YEWLKQAEAT RRLIIDNYSH LEGEELLQIT VAENVLTQLE
161 NLNTYPIVRS RLHQGRLSLH GWIYGIETGE VLTYDPKVHD
201 FVNLESRTDN SEYIYNLHPS CSVAKSMFYG IPDENDDKVQ
241 PSEPIPQTIN PNLPRSRSGA ARSNRLSPEQ EQRIYRGST
```

A related CcaA carbonate dehydratase is available from *Aliterella atlantica* that has at least 74% sequence identity to SEQ ID NO:17, as illustrated below.

```
57.2% identity in 271 residues overlap; Score: 786.0;
Gap frequency: 0.4%
Seq17    1 MRKLIEGLRHFRTSYYPSHRDLFEQFAKGQHPRVLFITCSDSRIDPNLITQSGMGELFVI
Seq20    1 MRKLIKGLRAFKDNYYSNHLELFEKLTHAQKPRVLFITCSDSRIDPNLITQAAVGELFVI
           ***** ***  *  ** * ** **    * ******************      ******

Seq17   61 RNAGNLIPPFGAANGGEGASIEYAIAALNIEHVVVCGHSHCGAMKGLLKLNQLQEDMPLV
Seq20   61 RNAGNLIPPFGATNGGEGATVEYAVHALGIEQIVVCGHSHCGAMKGLLKLNKLQQDMPLV
           ************ ****** **** **  ** ****************** ** *****

Seq17  121 YDWLQHAQATRRLVLDNYSGYETDDLVEILVAENVLTQIENLKTYPIVRSRLFQGKLQIF
Seq20  121 YNWLQYAESTRRLVQENYNSYSEEELVEIAVAENVLTQIENLKTYPVVRSKLYQGKLQIY
           * *** * * ****   **  *   ****  ***************  ***  ******

Seq17  181 GWIYEVESGEVLQISRTSSDDTGIDECPVRLPGSQE-KAILGRCVVPLTEEVAVAPPEPE
Seq20  181 AWIYHLETGEVLAYDPQSHAYVAPQSQLMNGDTTESIETRIANTSAPIVACEFPSRHKQR
            ***  * ****     *                *           *

Seq17  240 PVIAAVAAPPANYSSRGWLAPEQQQRIYRGN
Seq20  241 QVAHNTANNDGDTLPDMWLSPQQAERIYRGS
            *   *               ** *  ****
```

This CcaA related protein from *Aliterella atlantica* has a sequence that is available from the National Center for Biotechnology Information database (see website at ncbi.nlm.nih.gov) with accession number WP_045053064.1 (GI: 769918643), and with the sequence shown below (SEQ ID NO:20).

```
  1 MRKLIKGLRA FKDNYYSNHL ELFEKLTHAQ KPRVLFITCS

41 DSRIDPNLIT QAAVGELFVI RNAGNIIPPF GATNGGEGAT

81 VEYAVHALGI EQIVVCGHSH CGAMKGLLKL NKLQQDMPLV

121 YNWLQYAEST RRLVQENYNS YSEEELVEIA VAENVLTQIE

161 NLKTYPVVRS KLYQGKLQIY AWIYHLETGE VLAYDPQSHA

201 YVAPQSQLMN GDTTESIETR IANTSAPIVA CEFPSRHKQR

241 QVAHNTANND GDTLPDMWLS PQQAERIYRG SNGNR
```

A related CcaA carbonate dehydratase is available from *Leptolyngbya boryana* that has at least 74% sequence identity to SEQ ID NO:17, as illustrated below.

```
74.5% identity in 192 residues overlap; Score: 794.0;
Gap frequency: 0.0%
Seq17     1 MRKLIEGLRHFRTSYYPSHRDLFEQFAKGQHPRVLFITCSDSRIDPNLITQSGMGELFVI
Seq21     1 MKKLIQGHQQFWESYVPSHLDQLEELSHGQKPRVLFITCSDSRIDPNLITQAGIGELFVI
            * ***  *   *  ** ***  *    ** ******************** * ******

Seq17    61 RNAGNLIPPFGAANGGEGASIEYAIAALNIEHVVVCGHSHCGAMKGLLKLNQLQEDMPLV
Seq21    61 RNAGNIIPPFGAANGGEGAAVEYAIAALDIQQIIVCGHSHCGAMKGLLKLNKLQEDMPLV
            ***** *************  ******* *   ****************** *******

Seq17   121 YDWLQHAQATRRLVLDNYSGYETDDLVEILVAENVLTQIENLKTYPIVRSRLFQGKLQIF
Seq21   121 YDWLKHAEATRRLVKENYSQYSGEELLEITIAENVLTQIENLKTYPVVHSRLYQGKLEIY
            ****  ** *****  *** **  **  **  ************* * *** **** *

Seq17   181 GWIYEVESGEVL
Seq21   181 GWVYHIETGELL
            ** * * **  *
```

This CcaA related protein from *Leptolyngbya boryana* has a sequence that is available from the National Center for Biotechnology Information database (see website at ncbi.nlm.nih.gov) with accession number WP_017285834.1 (GI: 515855206), and with the sequence shown below (SEQ ID NO:21).

```
  1 MKKLIQGHQQ FWESYVPSHL DQLEELSHGQ KPRVLFITCS

41 DSRIDPNLIT QAGIGELFVI RNAGNIIPPF GAANGGEGAA

81 VEYAIAALDI QQIIVCGHSH CGAMKGLLKL NKLQEDMPLV

121 YDWLKHAEAT RRLVKENYSQ YSGEELLEIT IAENVLTQIE

161 NLKTYPVVHS RLYQGKLEIY GWVYHIETGE LLAFDPETHA

201 YVPPQSQLSP RELGAFYEKT SAPPVACNLP HKEDNGNGQL

241 RQPVTIRSQV KSAEPVPQTE VMPWLTAEQA QRIYQGSKR
```

Many cyanobacteria lack CcaA (Zarzycki et al., 2013) and its function can be replaced by the γ-CA domain of CcmM (Peña et al., 2010).

CcmC Chimeric Protein

A streamlined carboxysome core, referred to as CcmC, is described herein that combines segments of several carboxysome components into a single chimeric protein. CcmC contains scaffolding domains (the SSLDs that are involved in nucleating Rubisco), an enzymatic domain (carbonic anhydrase), and an encapsulating domain (the EP). FIG. 1B shows a schematic diagram of the chimeric protein. The following is an amino acid sequence for a CcmC gene (SEQ ID NO:22).

```
  1 MTVSAYNGQG RLSSEVITQV RSLLNQGYRI GTEHADKRRF

41 RTSSWQPCAP IQSTNERQVL SELENCLSEH EGEYVRLLGI

81 DTNTRSRVFE ALIQRPDGSV PESLGSQPVA VASGGGRQSS

121 YASVSGNLSA EVVNKVRNLL AQGYRIGTEH ADKRRFRTSS

161 WQSCAPIQSS NERQVLAELE NCLSEHEGEY VRLLGIDTAS

201 RSRVFEALIQ DPQGPVGSAK AAAAPVSSAT PSSHSYTSNG

241 SSSSDVAGQV RGLLAQGYRI SAEVADKRRF QTSSWQSLPA

281 LSGQSEATVL PALESILQEH KGKYVRLIGI DPAARRRVAE

321 LLIQKPGSRK LIEGLRHFRT SYYPSHRDLF EQFAKGQHPR
```

-continued
```
361 VLFITCSDSR IDPNLITQSG MGELFVIRNA GNLIPPFGAA

401 NGGEGASIEY AIAALNIEHV VVCGHSHCGA MKGLLKLNQL

441 QEDMPLVYDW LQHAQATRRL VLDNYSGYET DDLVEILVAE

481 NVLTQIENLK TYPIVRSRLF QGKLQIFGWI YEVESGEVLQ

521 ISRTSSDDTG IDECPVRLPG SQEKAILGRC VVPLTEEVAV

561 APPEPEPVIA AVAAPPANYS SRGWLGSGGS VYGKEQFLRM

601 RQSMFPDR
```

Note that amino acids 2-326 of the CcmC protein (with SEQ ID NO:22) are the same as the CcmM short form from *Synechococcus elongatus* PCC 7942 provided as SEQ ID NO:5. Similarly, amino acids 1-328 of the CcmC protein (with SEQ ID NO:22) are the same as amino acids 1-328 of the M35-EP protein with SEQ ID NO:37. The central amino acids 329-585 of the SEQ ID NO:38 CcmC protein correspond to amino acids 2-258 of the carbonate dehydratase (CcaA) with SEQ ID NO:71. Amino acids 591-608 of the SEQ ID NO:38 CcmC protein correspond to the encapsulation peptide (EP) from a CcmN protein, which has SEQ ID NO:13. Other M35, CcaA, and EP polypeptide segments can substitute for these M35, CcaA, and EP segments to form related CmcC proteins.

Such synthetic CcmC core proteins can support the assembly of functionally competent carboxysomes in cyanobacteria.

Such synthetic CcmC core proteins can have some sequence variation. For example, a CcmC core protein can have at least 40% sequence identity, or at least 50% sequence identity, or at least 60% sequence identity, or at least 70% sequence identity, or at least 80% sequence identity, or at least 90% sequence identity, or at least 95% sequence identity, or at least 96% sequence identity, or at least 97% sequence identity, or at least 98% sequence identity, or at least 99% sequence identity sequence identity (or complementarity) with SEQ ID NO:22. Related CcmC proteins can have, for example, 60-99% sequence identity, or 70-99% sequence identity, or 80-99% sequence identity, or 90-95% sequence identity, or 90-99% sequence identity, or 95-97% sequence identity, or 95-98% sequence identity, or 97-99% sequence identity, or 95-99% sequence identity, or 95-100% sequence identity, or 96-100% sequence identity, or 97-100% sequence identity, or 100% sequence identity (or complementarity) with SEQ ID NO:22.

Expression of multiple genes has previously been deemed to be necessary to assemble a BMC core in heterologous systems. However, the construct described herein has a streamlined design that functions to fix carbon even though it is smaller, and consists of a single polypeptide that has small subunit-like domains (SSLDs), Encapsulation peptide (EP), and carbonic anhydrase domains.

The more compact CcmC core protein can accommodate domain components with a variety sequences related to those described herein. For example, a CcmC core protein can have SSLDs (small subunit-like domains), encapsulation peptide (EP), and carbonic anhydrase domains that have at least 40% sequence identity, or at least 50% sequence identity, or at least 60% sequence identity, or at least 70% sequence identity, or at least 80% sequence identity, or at least 90% sequence identity, or at least 95% sequence identity, or at least 96% sequence identity, or at least 97% sequence identity, or at least 98% sequence identity, or at least 99% sequence identity, or 60-99% sequence identity, or 70-99% sequence identity, or 80-99% sequence identity, or 90-95% sequence identity, or 90-99% sequence identity, or 95-97% sequence identity, or 97-99% sequence identity, or 100% sequence identity (or complementarity) with any of the SEQ ID NOs described herein.

Previous attempts to engineer bacterial microcompartments have focused on associating heterologous proteins to shell proteins using encapsulation peptides (EPs). For example, through the addition of two different EPs to pyruvate decarboxylase and alcohol dehydrogenase, Lawrence et al. were able to repurpose a propanediol utilization (PDU) compartment for ethanol production (Lawrence et al., 2014). Lin et al. showed that the encapsulation peptide from CcmN targets yellow fluorescent protein into carboxysome-like structures formed in mutant tobacco (*Nicotiana benthamiana*) plants (Lin et al., 2014b).

In contrast to such previous studies the approach reported here focuses on assembling a multifunctional bacterial microcompartment core using a single polypeptide to nucleate assembly and provide key functions: CcmC nucleates Rubisco, supplies carbonic anhydrase activity, and recruits the shell. This approach allows the packaging of multiple protein domains within a shell using only a single encapsulation peptide (EP).

Shell Proteins

In some cases, it may be useful to express carboxysome shell protein(s) along with the CcmC chimeric core protein.

For example, a carbon dioxide concentrating mechanism protein CcmK and/or CcmL shell protein from *Synechococcus elongatus* PCC 7942 can be expressed along with the CcmC chimeric core protein. An example of a sequence for such a CcmK shell protein from *Synechococcus elongatus* PCC 7942 is provided below as SEQ ID NO:23 (see NCBI accession number (ABB56317.1; GI:81167977).

```
  1 MSQQAIGSLE TKGFPPILAA ADAMVKAGRI TIVSYMRAGS
 41 ARFAVNIRGD VSEVKTAMDA GIEAAKNTPG GTLETWVIIP
 81 RPHENVEAVF PIGFGPEVEQ YRLSAEGTGS GRR
```

An example of a sequence for such a CcmL shell protein from *Synechococcus elongatus* PCC 7942 is provided below as SEQ ID NO:24 (see NCBI accession number (ABB57452.1; GI:81169112).

```
  1 MRIAKVRGTV VSTYKEPSLQ GVKFLVVQFL DEAGQALQEY
 41 EVAADMVGAG VDEWVLISRG SQARHVRDCQ ERPVDAAVIA
 81 IIDTVNVENR SVYDKREHS
```

Such shell proteins can have some sequence variation. For example, such shell proteins can have at least 40% sequence identity, or at least 50% sequence identity, or at least 60% sequence identity, or at least 70% sequence identity, or at least 80% sequence identity, or at least 90% sequence identity, or at least 95% sequence identity, or at least 96% sequence identity, or at least 97% sequence identity, or at least 98% sequence identity, or at least 99% sequence identity, or 60-99% sequence identity, or 70-99% sequence identity, or 80-99% sequence identity, or 90-95% sequence identity, or 90-99% sequence identity, or 95-97% sequence identity, or 97-99% sequence identity, or 100% sequence identity (or complementarity) with SEQ ID NO:23 and/or SEQ ID NO:24.

Rubisco

In some cases, ribulose-1,5-bisphosphate carboxylase/oxygenase, abbreviated as Rubisco herein (also abbreviated as RuBPCase), can also be expressed with the chimeric core carboxysome CcmC protein. Rubisco is an enzyme that can be involved carbon fixation, to provide building blocks for energy-rich molecules such as glucose. Rubisco can catalyze the carboxylation of ribulose-1,5-bisphosphate, and may be one of the most abundant enzymes on Earth.

For example, a ribulose-1,5-bisphosphate carboxylase/oxygenase (Rubisco) protein can be expressed along with the CcmC chimeric core protein. An example of a sequence for such a Rubisco protein from *Synechococcus elongatus* PCC 7942 is provided below as SEQ ID NO:25 (see NCBI accession number (ABB57456.1; GI:81169116).

```
  1 MPKTQSAAGY KAGVKDYKLT YYTPDYTPKD TDLLAAFRFS
 41 PQPGVPADEA GAAIAAESST GTWTTVWTDL LTDMDRYKGK
 81 CYHIEPVQGE ENSYFAFIAY PLDLFEEGSV TNILTSIVGN
121 VFGFKAIRSL RLEDIRFPVA LVKTFQGPPH GIQVERDLLN
161 KYGRPMLGCT IKPKLGLSAK NYGRAVYECL RGGLDFTKDD
201 ENINSQPFQR WRDRFLFVAD AIHKSQAETG EIKGHYLNVT
241 APTCEEMMKR AEFAKELGMP IIMHDFLTAG FTANTTLAKW
```

```
281 CRDNGVLLHI HRAMHAVIDR QRNHGIHFRV LAKCLRLSGG
321 DHLHSGTVVG KLEGDKASTL GFVDLMREDH IEADRSRGVF
361 FTQDWASMPG VLPVASGGIH VWHMPALVEI FGDDSVLQFG
401 GGTLGHPWGN APGATANRVA LEACVQARNE GRDLYREGGD
441 ILREAGKWSP ELAAALDLWK EIKFEFETMD KL
```

Expression

The chimeric carboxysome core protein, shell protein(s), Rubisco protein(s), and combinations thereof can be expressed from an expression cassette or expression vector. An expression cassette can include a nucleic acid segment that encodes a chimeric carboxysome core protein, shell protein, or Rubisco protein operably linked to a promoter to drive expression. In some cases, such polypeptide(s) can be expressed using convenient vectors, or expression systems. The invention therefore provides expression cassettes or vectors useful for expressing one or more chimeric carboxysome core protein, shell protein, Rubisco protein.

For example, a nucleotide sequence that encodes the chimeric core carboxysome CcmC protein and that can be expressed in a variety of organisms, including *Synechococcus elongatus* PCC 7942, is shown below as SEQ ID NO:26.

```
  1 ATGACCGTGA GCGCTTATAA CGGCCAAGGC CGACTCAGTT
 41 CCGAAGTCAT CACCCAAGTC CGGAGTTTGC TGAACCAGGG
 81 CTATCGGATT GGGACGGAAC ATGCGGACAA GCGCCGCTTC
121 CGGACTAGCT CTTGGCAGCC CTGCGCGCCG ATTCAAAGCA
161 CGAACGAGCG CCAGGTCTTG AGCGAACTGG AAAATTGTCT
201 GAGCGAACAC GAAGGTGAAT ACGTTCGCTT GCTCGGCATC
241 GATACCAATA CTCGCAGCCG TGTTTTTGAA GCCCTGATTC
281 AACGGCCCGA TGGTTCGGTT CCTGAATCGC TGGGGAGCCA
321 ACCGGTGGCA GTCGCTTCCG GTGGTGGCCG TCAGAGCAGC
361 TATGCCAGCG TCAGCGGCAA CCTCTCAGCA GAAGTGGTCA
401 ATAAAGTCCG CAACCTCTTA GCCCAAGGCT ATCGGATTGG
441 GACGAAACAT GCAGACAAGC GCCGCTTTCG GACTAGCTCT
481 TGGCAGTCCT GCGCACCGAT TCAAAGTTCG AATGAGCGCC
521 AGGTTCTGGC TGAACTGGAA AACTGTCTGA GCGAGCACGA
561 AGGTGAGTAC GTTCGCCTGC TGGGCATCGA CACTGCTAGC
601 CGCAGTCGTG TTTTTGAAGC CCTGATCCAA GATCCCCAAG
641 GACCGGTGGG TTCCGCCAAA GCGGCCGCCG CACCTGTGAG
681 TTCGGCAACG CCCAGCAGCC ACAGCTACAC CTCAAATGGA
721 TCGAGTTCGA GCGATGTCGC TGGACAGGTT CGGGGTCTGC
761 TAGCCCAAGG CTACCGGATC AGTGCGGAAG TCGCCGATAA
801 GCGTCGCTTC CAAACCAGCT CTTGGCAGAG TTTGCCGGCT
841 CTGAGTGGCC AGAGCGAAGC AACTGTCTTG CCTGCTTTGG
881 AGTCAATTCT GCAAGAGCAC AAGGGTAAGT ATGTGCGCCT
921 GATTGGGATT GACCCTGCGG CTCGTCGTCG CGTGGCTGAA
961 CTGTTGATTC AAAAGCCGGG ATCTCGCAAG CTCATCGAGG
1001 GGTTACGGCA TTTCCGTACG TCCTACTACC CGTCTCATCG
1041 GGACCTGTTC GAGCAGTTTG CCAAAGGTCA GCACCCTCGA
1081 GTCCTGTTCA TTACCTGCTC AGACTCGCGC ATTGACCCTA
1121 ACCTCATTAC CCAGTCGGGC ATGGGTGAGC TGTTCGTCAT
1161 TCGCAACGCT GGCAATCTGA TCCCGCCCTT CGGTGCCGCC
1201 AACGGTGGTG AAGGGGCATC GATCGAATAC GCGATCGCAG
1241 CTTTGAACAT TGAGCATGTT GTGGTCTGCG GTCACTCGCA
1281 CTGCGGTGCG ATGAAAGGGC TGCTCAAGCT CAATCAGCTG
1321 CAAGAGGACA TGCCGCTGGT CTATGACTGG CTGCAGCATG
1361 CCCAAGCCAC CCGCCGCCTA GTCTTGGATA ACTACAGCGG
1401 TTATGAGACT GACGACTTGG TAGAGATTCT GGTCGCCGAG
1441 AATGTGCTGA CGCAGATCGA GAACCTTAAG ACCTACCCGA
1481 TCGTGCGATC GCGCCTTTTC CAAGGCAAGC TGCAGATTTT
1521 TGGCTGGATT TATGAAGTTG AAAGCGGCGA GGTCTTGCAG
1561 ATTAGCCGTA CCAGCAGTGA TGACACAGGC ATTGATGAAT
1601 GTCCAGTGCG TTTGCCCGGC AGCCAGGAGA AAGCCATTCT
1641 CGGTCGTTGT GTCGTCCCCC TGACCGAAGA AGTGGCCGTT
1681 GCTCCACCAG AGCCGGAGCC TGTGATCGCG GCTGTGGCGG
1721 CTCCACCCGC CAACTACTCC AGTCGCGGTT GGTTGGGATC
1761 TGGAGGCAGT GTCTACGGCA AGGAACAGTT TTTGCGGATG
1801 CGCCAGAGCA TGTTCCCCGA TCGCTAA
```

Another nucleotide sequence is provided below that encodes the chimeric core carboxysome CcmC protein and that has been codon-optimized for expression in *Escherichia coli* (SEQ ID NO:27).

```
  1 ATGACCGTTT CCGCGTACAA CGGACAGGGC AGACTTTCGA
 41 GTGAAGTTAT AACCCAGGTC CGGTCTTTGT TGAACCAAGG
 81 CTATCGCATC GGGACCGAAC ATGCCGATAA GCGCCGTTTC
121 CGGACCTCAA GTTGGCAACC GTGCGCGCCC ATCCAGTCAA
161 CCAATGAACG CCAGGTATTG TCTGAATTAG AGAATTGCTT
201 ATCGGAACAC GAAGGAGAAT ACGTTCGCTT GTTAGGAATT
241 GACACTAACA CAAGAAGTCG GGTTTTCGAA GCACTGATCC
281 AGCGCCCGGA CGGGTCTGTT CCTGAATCTT TGGGCAGCCA
321 GCCAGTAGCA GTGGCTTCCG GAGGCGGAAG ACAATCGTCC
361 TATGCATCTG TTTCCGGCAA CTTGTCTGCT GAGGTTGTTA
401 ATAAGGTGCG CAACCTGCTT GCCCAGGGTT ACAGAATTGG
441 CACGGAGCAC GCCGATAAGC GCCGTTTTAG AACCAGCTCG
481 TGGCAGTCTT GTGCGCCGAT ACAGTCCTCG AATGAACGGC
521 AGGTGCTGGC AGAGTTAGAG AATTGCCTGA GTGAGCATGA
561 AGGAGAATAC GTCCGCCTTC TGGGCATTGA CACCGCTTCC
```

-continued

```
 601 CGTTCGCGTG TTTTCGAAGC CCTTATTCAG GATCCGCAAG
 641 GCCCCGTGGG TTCCGCCAAA GCTGCCGCAG CACCTGTATC
 681 AAGTGCTACC CCTTCGTCCC ACAGTTATAC GTCGAACGGC
 721 AGCTCATCAT CTGACGTGGC GGGCCAGGTT CGTGGGTTGT
 761 TGGCTCAAGG GTATCGGATA TCGGCTGAGG TTGCGGATAA
 801 ACGTCGGTTC CAAACATCGT CGTGGCAGTC CTTGCCTGCA
 841 TTATCGGGTC AATCGGAAGC AACGGTCCTT CCTGCGCTGG
 881 AGAGTATCCT TCAGGAGCAC AAGGGCAAGT ACGTCAGATT
 921 GATAGGGATC GATCCGGCGG CGCGGAGACG GGTGGCAGAA
 961 TTGCTTATCC AAAAACCCGG TTCGCGCAAG TTGATCGAAG
1001 GATTAAGACA TTTTAGAACC TCATATTACC CGAGTCATAG
1041 AGATTTATTC GAGCAGTTTG CAAAGGGTCA ACACCCTAGA
1081 GTCCTGTTCA TCACTTGCTC GGATTCACGG ATCGATCCTA
1121 ATTTGATCAC GCAGTCTGGT ATGGGAGAGC TTTTCGTCAT
1161 CCGTAACGCA GGTAACCTGA TTCCACCTTT CGGCGCGGCA
1201 AATGGGGGTG AGGGTGCGTC CATTGAATAT GCCATCGCCG
1241 CATTGAATAT CGAACACGTA GTTGTATGTG GCCACTCGCA
1281 CTGTGGAGCG ATGAAAGGGC TGCTGAAGCT TAACCAGCTG
1321 CAAGAAGACA TGCCCCTTGT TTACGATTGG TTGCAACACG
1361 CGCAGGCCAC GAGACGTCTG GTCCTTGACA ACTACAGCGG
1401 ATATGAAACG GACGACCTTG TCGAGATCCT GGTCGCCGAG
1441 AACGTATTGA CCCAAATAGA GAATCTGAAG ACCTACCCAA
1481 TTGTGCGCTC GCGCTTGTTC CAGGGTAAGT TACAAATTTT
1521 CGGTTGGATC TATGAAGTGG AAAGTGGAGA GGTCTTGCAA
1561 ATCTCACGTA CATCCTCGGA CGACACAGGA ATAGACGAGT
1601 GCCCCGTCCG TTTACCGGGA TCGCAAGAGA AGGCCATTTT
1641 AGGACGGTGC GTCGTGCCAC TGACAGAGGA AGTGGCTGTT
1681 GCCCCTCCAG AACCAGAGCC TGTCATTGCT GCGGTGGCCG
1721 CACCACCCGC GAATTACTCC AGTCGCGGTT GGCTGGGCTC
1761 TGGAGGCTCT GTCTACGGAA AGGAACAATT CCTTCGTATG
1801 CGGCAATCAA TGTTCCCGGA CCGCTAA
```

Another nucleotide sequence is provided below that encodes the chimeric core carboxysome CcmC protein and that has been codon-optimized for expression in *Nicotiana tabacum* (SEQ ID NO:28).

```
   1 ATGACTGTGA GTGCATATAA TGGACAAGGT AGATTGAGTT
  41 CTGAAGTGAT AACTCAAGTG CGTAGCCTTT TGAATCAAGG
  81 ATACAGAATT GGGACCGAAC ACGCAGATAA AAGAAGGTTT
 121 AGAACCAGTT CATGGCAGCC ATGCGCCCCC ATCCAGTCTA
 161 CTAATGAAAG ACAAGTGCTT TCTGAGCTGG AAAACTGTCT
 201 TAGTGAACAT GAAGGCGAGT ATGTGCGATT GCTGGGTATC
 241 GATACTAACA CTCGTAGCCG TGTTTTTGAA GCTCTGATAC
 281 AACGACCTGA CGGTAGTGTC CCCGAATCAC TGGGTAGCCA
 321 GCCCGTAGCA GTAGCTAGCG GGGGCGGGCG ACAGTCCTCC
 361 TACGCCTCTG TTAGCGGCAA CCTCTCAGCC GAAGTAGTGA
 401 ACAAAGTAAG AAACCTCCTC GCCCAGGGTT ACCGTATAGG
 441 AACCGAGCAC GCAGACAAAC GAAGATTCAG GACTAGCAGC
 481 TGGCAATCCT GCGCACCCAT ACAATCTTCC AACGAAAGAC
 521 AGGTACTGGC AGAATTGGAA AACTGTCTTT CAGAACATGA
 561 AGGCGAGTAC GTCCGTCTGC TGGGGATCGA CACAGCAAGC
 601 AGAAGCCGAG TATTTGAAGC CCTCATTCAA GATCCACAGG
 641 GGCCAGTAGG TAGTGCAAAG GCAGCTGCAG CTCCCGTTTC
 681 ATCTGCTACT CCCAGCAGTC ACAGCTACAC TTCTAATGGG
 721 TCTTCCAGTA GTGACGTCGC CGGACAGGTA AGAGGCCTGT
 761 TGGCACAGGG TTACCGAATA TCTGCCGAAG TAGCTGATAA
 801 AAGGCGATTC CAGACTTCAT CCTGGCAGTC CCTTCCTGCA
 841 TTGTCTGGCC AATCTGAAGC CACTGTTCTT CCTGCACTTG
 881 AATCCATTTT GCAGGAACAT AAAGGTAAGT ATGTTCGATT
 921 GATCGGTATC GATCCAGCTG CACGTAGAAG GGTTGCAGAG
 961 TTATTGATTC AGAAGCCAGG ATCTGAAAAA TTAATAGAGG
1001 GTTTACGACA TTTCAGAACT TCTTACTACC CTTCCCATCG
1041 TGACTTATTC GAGCAATTTG CAAAAGGCCA ACATCCCAGA
1081 GTCTTGTTTA TCACTTGTTC AGACTCTCGA ATAGACCCCA
1121 ATCTCATAAC ACAGTCTGGA ATGGGCGAGC TTTTCGTGAT
1161 ACGTAACGCC GGCAACCTCA TTCCTCCCTT TGGTGCAGCT
1201 AACGGGGGCG AGGGGCTTC AATAGAGTAC GCTATCGCTG
1241 CCCTCAATAT CGAACACGTC GTAGTATGCG GACATTCACA
1281 TTGCGGGGCG ATGAAGGGAC TGTTGAAGCT GAATCAACTC
1321 CAAGAGGACA TGCCCCTGGT CTATGATTGG TTGCAGCACG
1361 CCCAAGCTAC TAGGAGATTA GTTTTAGACA ACTACTCTGG
1401 CTATGAAACT GATGACCTGG TAGAAATACT GGTCGCAGAA
1441 AACGTATTAA CTCAGATAGA AAATTTAAAG ACTTATCCCA
1481 TAGTCCGTAG CCGATTGTTC CAAGGAAAAT TGCAAATATT
1521 CGGGTGGATC TATGAGGTTG AGTCCGGAGA GGTCTTGCAG
1561 ATAAGTCGAA CTAGCTCCGA CGACACAGGG ATAGACGAAT
1601 GCCCAGTCAG GTTGCCCGGG TCTCAAGAGA AGCTATCTT
1641 GGGGAGGTGT GTCGTTCCTT TAACCGAGGA AGTTGCTGTC
1681 GCCCCCCCTG AGCCTGAACC TGTGATAGCT GCCGTAGCCG
1721 CACCCCCTGC CAACTATTCA TCACGAGGCT GGCTTGGCTC
1761 AGGGGGCTCA GTTTATGGGA AGGAACAATT CCTGAGGATG
1801 AGACAGTCAA TGTTCCCCGA TAGATAA
```

Another nucleotide sequence is provided below that encodes the chimeric core carboxysome CcmC protein and that has been codon-optimized for expression in *Chlamydomonas reinhardtii* (SEQ ID NO:29).

```
   1  ATGACGGTGT CGGCTTACAA CGGCCAGGGC CGCCTCTCGT
  41  CCGAGGTCAT TACGCAGGTC CGGAGCCTCC TGAACCAGGG
  81  GTACCGGATT GGTACCGAGC ATGCCGACAA GCGGCGCTTT
 121  CGGACGTCGT CCTGGCAGCC CTGCGCGCCC ATTCAGAGCA
 161  CCAACGAGCG GCAGGTCCTC TCCGAGCTGG AGAACTGCCT
 201  CAGCGAGCAT GAGGGGGAGT ACGTCCGCCT GCTGGGGATC
 241  GATACGAACA CGCGCTCCCG GGTCTTCGAG GCTCTCATCC
 281  AGCGCCCTGA CGGCTCGGTG CCTGAGAGCC TCGGCTCGCA
 321  GCCTGTGGCC GTGGCGAGCG GCGGTGGGCG GCAGTCCAGC
 361  TACGCCAGCG TGTCGGGTAA CCTCTCCGCC GAGGTCGTCA
 401  ACAAGGTGCG GAACCTCCTG GCCCAGGGCT ACCGGATCGG
 441  TACCGAGCAC GCCGACAAGC GCCGCTTTCG CACGAGCTCG
 481  TGGCAGAGCT GCGCCCCCAT TCAGTCGAGC AACGAGCGGC
 521  AGGTGCTCGC TGAGCTGGAG AACTGCCTCT CCGAGCATGA
 561  GGGCGAGTAC GTGCGGCTGC TCGGGATTGA TACGGCCTCG
 601  CGGTCGCGCG TGTTTGAGGC GCTGATCCAG GACCCCCAGG
 641  GTCCTGTCGG TTCGGCTAAG GCTGCGGCTG CCCCTGTGTC
 681  CTCGGCCACC CCCAGCTCGC ATTCGTACAC CTCGAACGGC
 721  TCCTCGTCGT CCGATGTGGC GGGTCAGGTG CGCGGGCTCC
 761  TCGCTCAGGG CTACCGCATC AGCGCTGAGG TCGCCGATAA
 801  GCGGCGGTTT CAGACGAGCT CGTGGCAGTC CCTCCCGGCG
 841  CTCTCGGGTC AGAGCGAGGC CACCGTCCTC CCTGCTCTCG
 881  AGTCGATTCT CCAGGAGCAT AAGGGGAAGT ACGTCCGGCT
 921  CATCGGGATT GACCCGGCTG CTCGGCGCCG CGTGGCGGAG
 961  CTGCTGATTC AGAAGCCTGG CAGCCGGAAG CTCATCGAGG
1001  GGCTCCGCCA TTTCCGGACG TCCTACTACC CCTCCCACCG
1041  CGATCTCTTC GAGCAGTTTG CCAAGGGGCA GCACCCGCGG
1081  GTCCTGTTCA TTACGTGCTC CGATAGCCGC ATTGACCCGA
1121  ACCTCATCAC GCAGAGCGGT ATGGGTGAGC TCTTTGTGAT
1161  TCGCAACGCT GGTAACCTCA TTCCTCCCTT TGGGGCGGCG
1201  AACGCGGCG AGGGTGCGTC GATTGAGTAC GCTATCGCCG
1241  CCCTCAACAT TGAGCATGTC GTGGTGTGCG GTCATAGCCA
1281  TTGCGGCGCG ATGAAGGGCC TCCTCAAGCT GAACCAGCTG
1321  CAGGAGGACA TGCCTCTGGT GTACGACTGG CTGCAGCATG
1361  CTCAGGCTAC GCGGCGCCTC GTCCTGGACA ACTACTCGGG
1401  CTACGAGACC GATGACCTCG TCGAGATCCT CGTCGCGGAG
1441  AACGTGCTGA CCCAGATTGA GAACCTCAAG ACGTACCCCA
1481  TCGTGCGCTC GCGCCTCTTC CAGGGCAAGC TGCAGATCTT
1521  CGGTTGGATT TACGAGGTGG AGTCGGGGGA GGTCCTGCAG
1561  ATCAGCCGGA CGAGCTCCGA CGACACCGGG ATCGATGAGT
1601  GCCCTGTCCG CCTGCCGGGC TCGCAGGAGA AGGCCATTCT
1641  GGGTCGGTGC GTGGTCCCCC TGACGGAGGA GGTGGCTGTG
1681  GCTCCTCCCG AGCCTGAGCC CGTCATTGCG GCGGTCGCCG
1721  CCCCTCCGGC TAACTACTCC AGCCGGGGGT GGCTCGGCTC
1761  CGGGGGGAGC GTCTACGGCA AGGAGCAGTT TCTGCGCATG
1801  CGGCAGTCGA TGTTCCCGGA TCGCTAA
```

The expression cassettes or vectors can include a promoter that is operably linked to a nucleic acid segment that encodes the chimeric core carboxysome CcmC protein. A promoter is a nucleotide sequence that controls expression of an operably linked nucleic acid sequence by providing a recognition site for RNA polymerase, and possibly other factors, required for proper transcription. A promoter includes a minimal promoter, consisting only of all basal elements needed for transcription initiation, such as a TATA-box and/or other sequences that serve to specify the site of transcription initiation. A promoter may be obtained from a variety of different sources. For example, a promoter may be derived entirely from a native gene, be composed of different elements derived from different promoters found in nature, or be composed of nucleic acid sequences that are entirely synthetic. A promoter may be derived from many different types of organisms and tailored for use within a given cell.

Any promoter able to direct transcription of an encoded peptide or polypeptide may be used. Accordingly, many promoters may be included within the expression cassette. Some useful promoters include constitutive promoters, inducible promoters, regulated promoters, cell specific promoters, viral promoters, and synthetic promoters. Particularly useful promoters are inducible promoters, especially those induced by inexpensive signals, or promoters that are auto-inducing under certain environmental conditions (e.g. a relatively dense cyanobacterial population).

For expression of one or more chimeric carboxysome core protein, shell protein, Rubisco protein, or combinations thereof in a host cell, one or more expression cassette can be used that has a nucleic acid segment encoding such protein(s) and a promoter operably linked thereto. Such a promoter can be any DNA sequence capable of binding a RNA polymerase and initiating the downstream (3") transcription of a coding sequence into mRNA. A promoter has a transcription initiation region that is usually placed proximal to the 5' end of the coding sequence. This transcription initiation region usually includes an RNA polymerase binding site and a transcription initiation site. A second domain called an operator may be present and overlap an adjacent RNA polymerase binding site at which RNA synthesis begins. The operator permits negatively regulated (inducible) transcription, as a gene repressor protein may bind the operator and thereby inhibit transcription of a specific gene.

Constitutive expression may occur in the absence of negative regulatory elements, such as the operator. In addition, positive regulation may be achieved by a gene activator protein binding sequence, which, if present is usually proximal (5') to the RNA polymerase binding sequence. An example of a gene activator protein is the catabolite activator protein (CAP), which helps initiate transcription of the lac operon in *E. coli* (Raibaud et al., *Ann. Rev. Genet.*, 18:173

(1984)). Regulated expression may therefore be positive or negative, thereby either enhancing or reducing transcription.

Other examples of promoters that can be employed include promoters of sugar metabolizing enzymes, such as galactose, lactose (lac) (Chang et al., *Nature*, 198:1056 (1977), and maltose. Additional examples include promoter sequences derived from biosynthetic enzymes such as tryptophan (Trp) (Goeddel et al., *Nuc. Acids Res.,* 8:4057 (1980); Yelverton et al., *Nuc. Acids Res.,* 9:731 (1981); U.S. Pat. No. 4,738,921; and EPO Publ. Nos. 036 776 and 121 775). The β-lactamase (bla) promoter system (Weissmann, "The cloning of interferon and other mistakes", in: Interferon 3 (ed. I. Gresser), 1981), and bacteriophage lambda $P_L$ (Shimatake et al., *Nature,* 292:128 (1981)) and T5 (U.S. Pat. No. 4,689,406) promoter systems also provide useful promoter sequences. Another example is the Chlorella virus promoter (U.S. Pat. No. 6,316,224).

Synthetic promoters that do not occur in nature also function as promoters in host cells. For example, transcription activation sequences of a promoter may be joined with the operon sequences of another promoter, creating a synthetic hybrid promoter (U.S. Pat. No. 4,551,433). For example, the tac promoter is a hybrid trp-lac promoter comprised of both trp promoter and lac operon sequences that is regulated by the lac repressor (Amann et al., Gene, 25:167 (1983); de Boer et al., Proc. Natl. Acad. Sci. USA, 80:21 (1983)). Furthermore, a promoter can include naturally occurring promoters of non-bacterial origin that have the ability to bind RNA polymerase and initiate transcription in cyanobacteria or other types of host cells. A naturally occurring promoter of non-bacterial origin can also be coupled with a compatible RNA polymerase to produce high levels of expression of some genes in prokaryotes. The bacteriophage T7 RNA polymerase/promoter system is an example of a coupled promoter system (Studier et al., *J. Mol. Biol.,* 189:113 (1986); Tabor et al., *Proc. Natl. Acad. Sci. USA,* 82:1074 (1985)). In addition, a hybrid promoter can also be comprised of a bacteriophage promoter and an *E. coli* operator region (EPO Publ. No. 267 851).

In some cases, quorum sensing-responsive promoters can be employed in the expression cassettes/vectors. Quorum sensing is a mechanism whereby bacteria are able to indirectly detect the concentration of neighboring cells. A quorum sensing pathway is one that is usually activated when a bacterial population becomes concentrated. For example, biofilm formation is controlled often by quorum sensing. Such quorum sensing promoters can make bacteria, cyanobacteria, or other cells self-induce the genes of interest when a certain cell concentration is reached (e.g., when the cells are ready, or will soon be ready, to be harvested), without the addition of chemical inducers. See, e.g., Miller, Melissa B., and Bonnie L. Bassler, "Quorum sensing in bacteria." Annual Reviews in Microbiology 55(1): 165-199 (2001).

In some cases, the promoter can become active at certain times during culture or fermentation. For example, the promoter can in some cases be active before, during, or after log phase growth of the cells during culture or fermentation.

For example, LuxI/LuxR genes are a family of genes that produce quorum sensing behavior in bacteria. See, e.g., Waters & Bassler, "Quorum sensing: cell-to-cell communication in bacteria," Ann Rev Cell Dev Biol 21: 319-46 (2005). Quorum sensing pathways in natural contexts involve a microbe that is capable of producing a diffusible molecule that can pass through the cell membrane, such as the class of molecules called acyl-homoserine lactones (AHL). These molecules can diffuse from the cell that produces them to the outside environment, and then back into other neighboring bacteria. When the concentration of AHL of a specific type becomes high enough, it can stabilize a transcription factor that turns on specific genes. Usually, quorum sensing pathways are utilized for bacteria to sense how large its population is—the more surrounding bacteria in the environment, the higher the AHL levels. At a certain cell density, the AHL builds up to a level that it can bind a receptor protein (e.g. LuxR), stabilizing it and allowing for downstream gene regulation.

Quorum sensing-responsive promoters can be used in any of the expression cassettes or expression vectors described herein. For example, host cells expressing LuxI (or similar protein) can make an AHL signal that could then build up as the cell density increases. When the cells become dense enough, they can turn on the expression of chimeric carboxysome core protein(s), shell protein(s), Rubisco protein(s), or combinations thereof.

One example of a protein that can modulate quorum sensing-responsive promoters is the LuxI from *Vibrio fishcheri*, with the following sequence (SEQ ID NO:30).

```
  1 MIKKSDFLGI PSEEYRGILS LRYQVFKRRL EWDLVSEDNL

41 ESDEYDNSNA EYIYACDDAE EVNGCWRLLP TTGDYMLKTV

81 FPELLGDQVA PRDPNIVELS RFAVGKNSSK INNSASEITM

121 KLFQAIYKHA VSQGITEYVT VTSIAIERFL KRIKVPCHRI

161 GDKEIHLLGN TRSVVLSMPI NDQFRKAVSN
```

A nucleic acid encoding this *Vibrio fishcheri* LuxI protein shown below (SEQ ID NO:31).

```
  1 ATGATAAAAA AATCGGACTT TTTGGGCATT CCATCAGAGG

41 AGTATAGAGG TATTCTTAGT CTTCGTTATC AGGTATTTAA

81 ACGAAGACTG GAGTGGGACT TGGTAAGTGA GGATAATCTT

121 GAATCAGATG AATATGATAA CTCAAATGCA GAATATATTT

161 ATGCTTGTGA TGATGCGGAA GAGGTAAATG GCTGTTGGCG

201 TTTGTTACCT ACAACGGGTG ATTACATGTT AAAAACTGTT

241 TTTCCTGAAT TGCTCGGAGA TCAAGTAGCC CCAAGAGATC

281 CAAATATAGT CGAATTAAGC CGTTTTGCTG TGGGAAAAAA

321 TAGCTCAAAA ATAAATAACT CTGCTAGTGA AATAACAATG

361 AAATTGTTTC AAGCTATATA TAAACACGCA GTTAGTCAAG

401 GTATTACAGA ATATGTAACA GTAACATCAA TAGCAATAGA

441 GCGATTTCTG AAACGTATTA AAGTTCCTTG TCATCGCATT

481 GGTGATAAGG AGATTCATTT ATTAGGTAAT ACTAGATCTG

521 TTGTATTGTC TATGCCTATT AATGATCAGT TTAGAAAAGC

561 TGTATCAAAT TAA
```

A sequence of a LuxR receptor protein from *Vibrio fishcheri* is shown below (SEQ ID NO:32).

```
  1 MIYNTQNLRQ TIGKDKEMGM KNINADDTYR IINKIKACRS

41 NNDINQCLSD MTKMVHCEYY LLAIIYPHSM VKSDISILDN

81 YPKKWRQYYD DANLIKYDPI VDYSNSNHSP INWNIFENNA
```

```
121  VNKKSPNVIK EAKTSGLITG FSFPIHTANN GFGMLSFAHS

161  EKDNYIDSLF LHACMNIPLI VPSLVDNYRK INIANNKSNN

201  DLTKREKECL AWACEGKSSW DISKILGCSE RTVTFHLTNA

241  QMKLNTTNRC QSISKAILTG AIDCPYFKN
```

A nucleic acid sequence for this LuxR protein from *Vibrio fishcheri* is provided below as SEQ ID NO:33.

```
  1  ATGATATATA ACACGCAAAA CTTGCGACAA ACAATAGGTA

41  AGGATAAAGA GATGGGTATG AAAAACATAA ATGCCGACGA

81  CACATACAGA ATAATTAATA AAATTAAAGC TTGTAGAAGC

121  AATAATGATA TTAATCAATG CTTATCTGAT ATGACTAAAA

161  TGGTACATTG TGAATATTAT TTACTCGCGA TCATTTATCC

201  TCATTCTATG GTTAAATCTG ATATTTCAAT TCTAGATAAT

241  TACCCTAAAA AATGGAGGCA ATATTATGAT GACGCTAATT

281  TAATAAAATA TGATCCTATA GTAGATTATT CTAACTCCAA

321  TCATTCACCA ATTAATTGGA ATATATTTGA AAACAATGCT

361  GTAAATAAAA AATCTCCAAA TGTAATTAAA GAAGCGAAAA

401  CATCAGGTCT TATCACTGGG TTTAGTTTCC CTATTCATAC

441  GGCTAACAAT GGCTTCGGAA TGCTTAGTTT TGCACATTCA

481  GAAAAAGACA ACTATATAGA TAGTTTATTT TTACATGCGT

521  GTATGAACAT ACCATTAATT GTTCCTTCTC TAGTTGATAA

561  TTATCGAAAA ATAAATATAG CAAATAATAA ATCAAACAAC

601  GATTTAACCA AAAGAGAAAA AGAATGTTTA GCGTGGGCAT

641  GCGAAGGAAA AAGCTCTTGG GATATTTCAA AAATATTAGG

681  CTGCAGTGAG CGTACTGTCA CTTTCCATTT AACCAATGCG

721  CAAATGAAAC TCAATACAAC AAACCGCTGC CAAAGTATTT

761  CTAAAGCAAT TTTAACAGGA GCAATTGATT GCCCATACTT

801  TAAAAATTAA
```

An example of a LuxR-responsive promoter from *Vibrio fishcheri* is shown below as (SEQ ID NO:34).

```
  1  TGTCGCAAGT TTTGCGTGTT ATATATCATT AAAACGGTAA

41  TGGATTGACA TTTGATTCTA ATAAATTGGA TTTTTGTCAC

81  ACTATTGTAT CGCTGGGAAT ACAATTACTT AACATAAGCA

121  CCTGTAGGAT CGTACAGGTT TACGCAAGAA AATGGTTTGT

161  TATAGTCGAA TGAATTCATT AAAGAGGAGA AAGGTACC
```

When LuxR is expressed and stabilized (because AHL is present), the LuxR protein binds to a promoter sequence like that shown above as (SEQ ID NO:34) and drives gene expression from it.

It is understood that many promoters and associated regulatory elements may be used within the expression cassette/vector to transcribe an RNA encoding a chimeric carboxysome core protein. The promoters described above are provided merely as examples and are not to be considered as a complete list of promoters that are included within the scope of the invention.

The expression cassette of the invention may contain a nucleic acid sequence for increasing the translation efficiency of an mRNA encoding a chimeric carboxysome core protein. Such increased translation serves to increase production of the protein. The presence of an efficient ribosome binding site is useful for gene expression in prokaryotes. In bacterial mRNA, a conserved stretch of six nucleotides, the Shine-Dalgarno sequence, is usually found upstream of the initiating AUG codon. (Shine et al., *Nature,* 254:34 (1975)). This sequence is thought to promote ribosome binding to the mRNA by base pairing between the ribosome binding site and the 3' end of *Escherichia coli* 16S rRNA. (Steitz et al., "Genetic signals and nucleotide sequences in messenger RNA", in: Biological Regulation and Development: Gene Expression (ed. R. F. Goldberger), 1979)). Such a ribosome binding site, or operable derivatives thereof, are included within the expression cassette of the invention.

A translation initiation sequence can be derived from any expressed gene and can be used within an expression cassette/vector of the invention. Preferably the gene from which the translation initiation sequence is obtained is a highly expressed gene. A translation initiation sequence can be obtained via standard recombinant methods, synthetic techniques, purification techniques, or combinations thereof, which are all well known. (Ausubel et al., *Current Protocols in Molecular Biology,* Green Publishing Associates and Wiley Interscience, NY. (1989); Beaucage and Caruthers, *Tetra. Letts.,* 22:1859 (1981); VanDevanter et al., *Nucleic Acids Res.,* 12:6159 (1984). Alternatively, translational start sequences can be obtained from numerous commercial vendors. (Operon Technologies; Life Technologies Inc, Gaithersburg, Md.). In some embodiments, the T7 translation initiation sequence is used. The T7 translation initiation sequence is derived from the highly expressed T7 Gene 10 cistron and can have a sequence that includes TCTAGAAATAATTTTGTTTAACTTTAAGAA GGAGATATA (SEQ ID NO:35). Other examples of translation initiation sequences include, but are not limited to, the maltose-binding protein (Mal E gene) start sequence (Guan et al., *Gene,* 67:21 (1997)) present in the pMalc2 expression vector (New England Biolabs, Beverly, Mass.) and the translation initiation sequence for the following genes: thioredoxin gene (Novagen, Madison, Wis.), Glutathione-S-transferase gene (Pharmacia, Piscataway, N.J.), β-galactosidase gene, chloramphenicol acetyltransferase gene and *E. coli* Trp E gene (Ausubel et al., 1989, *Current Protocols in Molecular Biology,* Chapter 16, Green Publishing Associates and Wiley Interscience, NY).

The invention therefore provides an expression cassette or vector that includes a promoter operable in a selected host and a nucleic acid encoding one of the chimeric carboxysome core proteins described herein. The expression cassette can have other elements, for example, termination signals, origins of replication, enhancers, and the like as described herein. The expression cassette can also be placed in a vector for easy replication and maintenance.

An expression cassette or nucleic acid construct of the invention is thought to be particularly advantageous for inducing expression of the polypeptides.

Host Organisms

The chimeric carboxysome core protein can be expressed by a variety of organisms. Examples of organisms that can be modified to express the chimeric carboxysome core protein can include microorganisms, plants (including land-based plants and aqueous plants), and fungi. For example, bacteria, cyanobacteria, algae, microalgae, seaweed, plankton, single-celled fungal cells, multi-celled fungi, plant cells, and multi-celled plants can be modified to express the chimeric carboxysome core protein.

In some cases, the chimeric carboxysome core protein can be expressed in addition to native or endogenous carboxysome components.

Any cyanobacteria can be modified to express the chimeric carboxysome core protein, either permanently or transiently.

Examples of cyanobacterial species that can be changed include *Synechococcus elongatus* sp. PCC 7942; *Synechococcus elongatus* 7002; *Synechococcus elongatus* UTEX 2973; *Anthropira platensis*; and *Leptolyngbya* sp. strain BL0902. *Synechococcus elongatus* sp. PCC 7942 is one of the dominant model organisms, providing a variety of useful genetic tools. *Synechococcus elongatus* 7002 is a well-developed model organism with improved productivity and resilience. *Synechococcus elongatus* UTEX 2973 is related to *S. elongatus* 7942, and it has greatly improved growth properties. *Anthropira platensis* is perhaps the most broadly utilized cyanobacteria in scaled applications. *Leptolyngbya* sp. strain BL0902 is a bioindustrial strain whose genetic make-up is not as well-studied as some of the model cyanobacterial species.

Further examples of cyanobacterial species that can be modified include, for example, any of those in Table 1.

TABLE 1

Types of Cyanobacteria

| Species | Lineage | Release |
|---|---|---|
| *Synechococcus elongatus* sp. PCC 7942 | Cyanobacteria; Oscillatoriophycideae; Chroococcales; Synechococcus | American Type Culture Collection, ATCC accession no. 33912. |
| *Synechococcus elongatus* UTEX 2973 | Cyanobacteria; Oscillatoriophycideae; Chroococcales; Synechococcus | UTEX Culture Collection of Algae, University of Texas at Austin |
| *Anthropira platensis* | Cyanobacteria; Oscillatoriophycideae; Oscillatoriales; Arthrospira | American Type Culture Collection, ATCC accession no. 29408. |
| *Prochlorococcus marinus* str. AS9601 | Cyanobacteria; Prochlorales; Prochlorococcaceae; Prochlorococcus | The Gordon and Betty Moore Foundation Marine Microbiology Initiative (2007) |
| *Acaryochloris marina* MBIC11017 | Cyanobacteria; Acaryochloris | TGen Sequencing Center (2008) |
| Anabaena sp. PCC 7120 | Cyanobacteria; Nostocales; Nostocaceae; Nostoc | Kazusa (2001) |
| *Anabaena variabilis* ATCC 29413 | Cyanobacteria; Nostocales; Nostocaceae; Anabaena | JGI (2007) |
| Synechococcus sp. CC9311 | Cyanobacteria; Chroococcales; Synechococcus | TIGR (2006) |
| Cyanothece sp. ATCC 51142 | Cyanobacteria; Chroococcales; Cyanothece | Washington University (2008) |
| *Chlorobium tepidum* TLS | Chlorobi; Chlorobia; Chlorobiales; Chlorobiaceae; Chlorobaculum | TIGR (2002) |
| Synechococcus sp. JA-3-3Ab | Cyanobacteria; Chroococcales; Synechococcus | TIGR (2007) |
| Cyanothece sp. PCC 7425 | Cyanobacteria; Chroococcales; Cyanothece | |
| Synechococcus sp. JA-2-3B'a(2-13) | Cyanobacteria; Chroococcales; Synechococcus | TIGR (2007) |
| *Gloeobacter violaceus* PCC 7421 | Cyanobacteria; Gloeobacteria; Gloeobacterales; Gloeobacter | Kazusa (2003) |
| *Prochlorococcus marinus* MED4 | Cyanobacteria; Prochlorales; Prochlorococcaceae; Prochlorococcus | JGI (2003) |
| *Microcystis aeruginosa* NIES-843 | Cyanobacteria; Chroococcales; Microcystis | Kazusa, Tsukuba, NIES (2007) |
| *Prochlorococcus marinus* MIT9313 | Cyanobacteria; Prochlorales; Prochlorococcaceae; Prochlorococcus | JGI (2003) |
| *Prochlorococcus marinus* str. NATL1A | Cyanobacteria; Prochlorales; Prochlorococcaceae; Prochlorococcus | The Gordon and Betty Moore Foundation Marine Microbiology Initiative (2007) |
| *Arthrospira platensis* NIES-39 | Cyanobacteria; Oscillatoriales; Arthrospira; *Arthrospira platensis* | |
| *Nostoc punctiforme* ATCC 29133 | Cyanobacteria; Nostocales; Nostocaceae; Nostoc | JGI (2008) |
| *Prochlorococcus marinus* str. MIT 9211 | Cyanobacteria; Prochlorales; Prochlorococcaceae; Prochlorococcus | The Gordon and Betty Moore Foundation Marine Microbiology Initiative (2008) |
| *Prochlorococcus marinus* str. MIT 9215 | Cyanobacteria; Prochlorales; Prochlorococcaceae; Prochlorococcus | JGI (2007) |

TABLE 1-continued

Types of Cyanobacteria

| Species | Lineage | Release |
|---|---|---|
| *Prochlorococcus marinus* str. MIT 9301 | Cyanobacteria; Prochlorales; Prochlorococcaceae; Prochlorococcus | The Gordon and Betty Moore Foundation Marine Microbiology Initiative (2007) |
| *Prochlorococcus marinus* str. MIT 9303 | Cyanobacteria; Prochlorales; Prochlorococcaceae; Prochlorococcus | The Gordon and Betty Moore Foundation Marine Microbiology Initiative (2007) |
| *Prochlorococcus marinus* str. MIT 9515 | Cyanobacteria; Prochlorales; Prochlorococcaceae; Prochlorococcus | The Gordon and Betty Moore Foundation Marine Microbiology Initiative (2007) |
| *Synechococcus elongatus* PCC 6301 | Cyanobacteria; Chroococcales; Synechococcus | Nagoya U. (2007) |
| Cyanothece sp. PCC 7424 | Cyanobacteria; Chroococcales; Cyanothece | |
| Cyanothece sp. PCC 8801 | Cyanobacteria; Chroococcales; Cyanothece | |
| *Prochlorococcus marinus* str. NATL2A | Cyanobacteria; Prochlorales; Prochlorococcaceae; Prochlorococcus | JGI (2007) |
| *Prochlorococcus marinus* str. MIT 9312 | Cyanobacteria; Prochlorales; Prochlorococcaceae; Prochlorococcus | JGI (2007) |
| *Rhodopseudomonas palustris* CGA009 | Proteobacteria; Alphaproteobacteria; Rhizobiales; Bradyrhizobiaceae; Rhodopseudomonas | JGI (2003) |
| *Prochlorococcus marinus* SS120 | Cyanobacteria; Prochlorales; Prochlorococcaceae; Prochlorococcus | Genoscope (2003) |
| Synechococcus sp. CC9605 | Cyanobacteria; Chroococcales; Synechococcus | JGI (2007) |
| Synechococcus sp. CC9902 | Cyanobacteria; Chroococcales; Synechococcus | JGI (2007) |
| Synechocystis sp. PCC 6803 | Cyanobacteria; Chroococcales; Synechocystis | Kazusa (1996, 2002, 2003) |
| Synechococcus sp. PCC 7002 | Cyanobacteria; Chroococcales; Synechococcus | Penn State University (2008) |
| *Synechococcus elongatus* PCC 7942 | Cyanobacteria; Chroococcales; Synechococcus | JGI (2007) |
| Synechococcus sp. RCC307 | Cyanobacteria; Chroococcales; Synechococcus | Genoscope (2007) |
| Synechococcus sp. WH 7803 | Cyanobacteria; Chroococcales; Synechococcus | Genoscope (2007) |
| *Trichodesmium erythraeum* IMS101 | Cyanobacteria; Oscillatoriales; Trichodesmium; *Trichodesmium erythraeum* | |
| *Thermosynechococcus elongatus* BP-1 | Cyanobacteria; Chroococcales; Thermosynechococcus | Kazusa (2002) |
| Synechococcus sp. WH8102 | Cyanobacteria; Chroococcales; Synechococcus | JGI (2003) |

Useful Products

The cells, plants, cyanobacteria, bacteria, algae, microalgae and other cells/organisms that express the fusion proteins described herein can produce a variety of products such as oils, carbohydrates, grains, vegetables, fruits and other components, as well as 3-phosphoglycerate (3-PGA). Examples include oils (fatty acids), alkenes, polyhydroxybutyrate, biomass, carbohydrates, phycocyanin, ethanol, hydrogen, isobutanol, ethylene, and combinations thereof. Products such as oils (fatty acids), alkenes, ethanol, hydrogen, isobutanol, ethylene, and combinations thereof can be used in manufacturing and as biofuels. For example, ethanol, carbohydrate feedstocks, and biomass can be used to make bioethanol. Polyhydroxybutyrate is useful, for example, in bioplastics. Biomass, carbohydrates, and ethanol can also be used in foods and food manufacturing. Ethanol, hydrogen, isobutanol, and ethylene are useful in manufacturing, as a source of energy, and/or for making fuel.

The following non-limiting Examples describe some of the experiments performed.

Example 1: Materials and Methods

This Example describes some of the methods that were used during development of the invention.

Cyanobacterial Strain and Growth Conditions

*Synechococcus elongatus* PCC 7942 (Syn 7942) cultures were grown in 250 ml baffled Erlenmeyer flasks with 60 ml BG-11 medium (Rippka et al., 1979) buffered with 10 mM HEPES pH 8.0 under the following growth chamber settings: temperature of 30° C., light intensity of 40 moles photons $m^{-2}s^{-1}$, shaking at 150 rpm and $CO_2$ concentrations of 5%, 3% or air. Unless otherwise indicated, experiments were performed in cultures at exponential growth phase ($OD_{730}$=0.4-0.7).

Mutant Generation

*Synechococcus elongatus* PCC 7942 cells were transformed as described by Kufryk et al. (2002). Cultures were grown to $OD_{730}$=0.5 and concentrated to $OD_{730}$=2.5 by centrifugation at 5000 relative centrifugal force (rcf) for 5 minutes. Five microliters of plasmids (~1 µg of DNA) prepared from *E. coli* DH5α cells were added to 400 µl of the cyanobacterial cell suspension and incubated for 6 hours. The 400 µl-aliquots were dried on Nucleopore track-etched polycarbonate membranes (GE Healthcare) on top of BG-11 plates and incubated for 12-24 hours. The membranes were transferred to BG-11 plates with the proper selectable marker until resistant colonies were obtained.

All mutant strains were transformed with pJCC008 plasmid (rbcL-GFP placed under the control of the ccmk2 promoter) (Cameron et al., 2013) for GFP-labeling of the large subunit of Rubisco (RbcL) to enable carboxysome visualization by fluorescence microscopy. The carboxysome-minus strain COREΔ2/RbcL-GFP was generated by replacing synpcc7942_1423 and synpcc7942_1424 genes with a kanamycin resistance/sucrose sensitivity cassette obtained from the pPSBAII-KS plasmid (Lagarde et al., 2000) and using synpcc7942_1422 and synpcc7942_1425 sequences as flanking regions for double homologous recombination. Domains for the generation of chimeric proteins were assigned using the InterPro software (Hunter et al., 2012) and the HMM tool from JCVI institute (see website at blast.jcvi.org/web-hmm).

DNA was obtained from Cyanobase (see website at genome.microbedb.jp/cyanobase) and cloned by methods involving restriction digestion and ligation (see, e.g., Sambrook and Russell, 2001) as follows.

Plasmids with genes coding for the chimeric proteins had the following amino acid sequences.

The following is an amino acid sequence for a CcaA-M35 gene (SEQ ID NO:36).

```
  1 MRKLIEGLRH FRTSYYPSHR DLFEQFAKGQ HPRVLFITCS
 41 DSRIDPNLIT QSGMGELFVI RNAGNLIPPF GAANGGEGAS
 81 IEYAIAALNI EHVVVCGHSH CGAMKGLLKL NQLQEDMPLV
121 YDWLQHAQAT RRLVLDNYSG YETDDLVEIL VAENVLTQIE
141 NLKTYPIVRS RLFQGKLQIF GWIYEVESGE VLQISRTSSD
181 DTGIDECPVR LPGSQEKAIL GRCVVPLTEE VAVAPPEPEP
221 VIAAVAAPPA NYSSRGWLAP EQQQRIYRGN ASGSVSAYNG
261 QGRLSSEVIT QVRSLLNQGY RIGTEHADKR RFRTSSWQPC
281 APIQSTNERQ VLSELENCLS EHEGEYVRLL GIDTNTRSRV
321 FEALIQRPDG SVPESLGSQP VAVASGGGRQ SSYASVSGNL
361 SAEVVNKVRN LLAQGYRIGT EHADKRRFRT SSWQSCAPIQ
401 SSNERQVLAE LENCLSEHEG EYVRLLGIDT ASRSRVFEAL
441 IQDPQGPVGS AKAAAAPVSS ATPSSHSYTS NGSSSSDVAG
481 QVRGLLAQGY RISAEVADKR RFQTSSWQSL PALSGQSEAT
521 VLPALESILQ EHKGKYVRLI GIDPAARRRV AELLIQKP
```

The following is an amino acid sequence for an M35-EP (SEQ ID NO:37).

```
  1 MTVSAYNGQG RLSSEVITQV RSLLNQGYRI GTEHADKRRF
 41 RTSSWQPCAP IQSTNERQVL SELENCLSEH EGEYVRLLGI
 81 DTNTRSRVFE ALIQRPDGSV PESLGSQPVA VASGGGRQSS
121 YASVSGNLSA EVVNKVRNLL AQGYRIGTEH ADKRRFRTSS
161 WQSCAPIQSS NERQVLAELE NCLSEHEGEY VRLLGIDTAS
201 RSRVFEALIQ DPQGPVGSAK AAAAPVSSAT PSSHSYTSNG
241 SSSSDVAGQV RGLLAQGYRI SAEVADKRRF QTSSWQSLPA
281 LSGQSEATVL PALESILQEH KGKYVRLIGI DPAARRRVAE
321 LLIQKPGSGG SVYGKEQFLR MRQSMFPDR
```

The following is an amino acid sequence for a CcmC protein (SEQ ID NO:38).

```
  1 MTVSAYNGQG RLSSEVITQV RSLLNQGYRI GTEHADKRRF
 41 RTSSWQPCAP IQSTNERQVL SELENCLSEH EGEYVRLLGI
 81 DTNTRSRVFE ALIQRPDGSV PESLGSQPVA VASGGGRQSS
121 YASVSGNLSA EVVNKVRNLL AQGYRIGTEH ADKRRFRTSS
161 WQSCAPIQSS NERQVLAELE NCLSEHEGEY VRLLGIDTAS
201 RSRVFEALIQ DPQGPVGSAK AAAAPVSSAT PSSHSYTSNG
241 SSSSDVAGQV RGLLAQGYRI SAEVADKRRF QTSSWQSLPA
281 LSGQSEATVL PALESILQEH KGKYVRLIGI DPAARRRVAE
321 LLIQKPGSRK LIEGLRHFRT SYYPSHRDLF EQFAKGQHPR
361 VLFITCSDSR IDPNLITQSG MGELFVIRNA GNLIPPFGAA
401 NGGEGASIEY AIAALNIEHV VVCGHSHCGA MKGLLKLNQL
441 QEDMPLVYDW LQHAQATRRL VLDNYSGYET DDLVEILVAE
481 NVLTQIENLK TYPIVRSRLF QGKLQIFGWI YEVESGEVLQ
521 ISRTSSDDTG IDECPVRLPG SQEKAILGRC VVPLTEEVAV
561 APPEPEPVIA AVAAPPANYS SRGWLGSGGS VYGKEQFLRM
601 RQSMFPDR
```

Note that amino acids 1-328 of the CcmC protein (with SEQ ID NO:38) are the same as amino acids 1-328 of the M35-EP protein with SEQ ID NO:37. The central amino acids 329-585 (in bold) of the SEQ ID NO:38 CcmC protein correspond to amino acids 2-258 of the carbonate dehydratase (CcaA) with SEQ ID NO:71. Amino acids 591-608 of the SEQ ID NO:38 CcmC protein correspond to the encapsulation peptide from a CcmN protein, which has SEQ ID NO:13.

Note also that in the case of CcmC, the C-terminal extension of the β-CA was used as linker and its terminal 14 amino acids were replaced by 18 amino acids comprising the EP with synpcc7942_1422 and synpcc7942_1425 sequences as flanking regions were transformed into the COREΔ2/RbcL-GFP strain.

Growth in air was used for positive selection and growth in 5% sucrose as confirmation. The COREΔ2/CcmC/RbcL-GFP strain is obtained after CcmC restores growth in air. CcaA (Synpcc7942_1447) was interrupted in the COREΔ2/CcmC/RbcL-GFP strain and in Wild-type/RbcL-GFP by insertion of a gentamycin resistance cassette and selection with 5 µg/ml gentamycin in solid BG-11 plates (resulting in COREΔ3/CcmC/RbcL-GFP strain and ΔCcaA/RbcL-GFP strain, respectively). Primers used are described in Table 2.

TABLE 2

Primers

| Primer ID | Purpose | Sequence |
|---|---|---|
| pUC19 speI fwd | CcmM-N deletion | GGTGCACTACTAGTACAATCTGC (SEQ ID NO: 39) |
| pUC19 speI rv | CcmM-N deletion | GTGAAATACCGCACTAGTGCGTAAG (SEQ ID NO: 40) |
| FR left (ccmL-O) fwd | CcmM-N deletion | CTTTCATCTTGAATTCCGACTCTTTAGG (SEQ ID NO: 41) |
| FR left (ccmL-O) rv | CcmM-N deletion | GCTCGGCATATGCTAACCTC (SEQ ID NO: 42) |
| FR right (ccmL-O) fwd | CcmM-N deletion | GGGAGGTTAGCATATGCTCTAGAAGCTGCAGG (SEQ ID NO: 43) |
| FR right (ccmL-O) rv | CcmM-N deletion | CTACTGAGTCCGAAGCTTTCAGC (SEQ ID NO: 44) |
| $Km^R$/SacB fwd | CcmM-N deletion | GAATTATAACCATATGCATCCTAGG (SEQ ID NO: 45) |
| $Km^R$/SacB rv | CcmM-N deletion | TCCCGTCTAGACAGCGTAATG (SEQ ID NO: 46) |
| CcaA ndeI fwd | ccmC, ccaA-M35 | GAGTATCACTCATATGCGCAAGC (SEQ ID NO: 47) |
| CcaA BamHI rv | ccaA-M35 | CTTCGGGATCCGCTAGCATTG (SEQ ID NO: 48) |
| SSLDs-CcmN bglII fwd- | ccaA-M35 | TAGCGAGGCAAGATCTGTGAGC (SEQ ID NO: 49) |
| SSLDs-CcmN xhoI rv- | ccaA-M35 | CCTGCAGCTTCTAGAGCTGCTGTG (SEQ ID NO: 50) |
| CcaA$_{(short)}$ bamHI rv | ccmC | GTTGTTGTTCGGATCCCAACCAAC (SEQ ID NO: 51) |
| EP bglII fwd | ccmC, M35-EP | CCCAGATCTGGAGGCAGTGTCTACGGCAAGGAAC (SEQ ID NO: 52) |
| EP NcoI rv | ccmC, M35-EP | CGTGGCCATGGCTTCTTGGGAGAGC (SEQ ID NO: 53) |
| ccaA$_{(short)}$ bglII fwd | ccmC | GCCCTTGTCAGATCTCGCAAGCTCATCG (SEQ ID NO: 54) |
| SSLDs ndeI fwd | ccmC, M35-EP | CTAGCGAGCATATGACCGTGAGCGC (SEQ ID NO: 55) |
| SSLDs bamHI rv | ccmC, M35-EP | CAGGATCCTCCCGGCTTTTGTTAGAGC (SEQ ID NO: 56) |
| FR left (ccaA) notI fwd | CcaA deletion | CAGCGGCCGCGCCTAGTGC (SEQ ID NO: 57) |
| FR left (ccaA) xhoI rv | CcaA deletion | GCTTGCGCATCTCGAGTGATACTCGGGAC (SEQ ID NO: 58) |
| FR right (ccaA) xbaI fwd | CcaA deletion | GCGGCAATTCTAGATAGGATCGAAGCATC (SEQ ID NO: 59) |
| FR right (ccaA) ncoI rv | CcaA deletion | TACCCATGGACTCAAGCGCTCATTGCCAG (SEQ ID NO: 60) |
| $Gm^R$ xhoI fwd | CcaA deletion | GGTACCGAGCTCGAGTTGACATAAGC (SEQ ID NO: 61) |
| $Gm^R$ xbaI rv | CcaA deletion | TCCGCGGCTCTAGAGCCGATC (SEQ ID NO: 62) |

TABLE 2-continued

Primers

| Primer ID | Purpose | Sequence |
|---|---|---|
| Primer A | Screening | TGCCTATTGCGGTTGGAATG (SEQ ID NO: 63) |
| Primer B | Screening | AATCATGATGCACGCCCTTG (SEQ ID NO: 64) |
| Primer C | Screening | AATCATGATGCACGCCCTTG (SEQ ID NO: 65) |
| Primer D | Screening | TTAGCCGATTTGAGCATGGC (SEQ ID NO: 66) |
| Primer E | Screening | CAGCTTTGAACATTGAGCATGTTGTG (SEQ ID NO: 67) |
| Primer F | Screening | ATTGCCGCGATAAATCCGCTG (SEQ ID NO: 68) |

Structural Modeling

The predicted domains obtained (FIG. 1A) were used as input for the automated mode of the SwissModel (Biasini et al., 2014) server. The EP was manually added to the predicted structure of CcmC using the software Chimera (Pettersen et al., 2004).

Spectrophotometric Measurements

Culture growth was monitored as the change in optical density at 730 nm ($OD_{730}$). Chl α concentration was determined by absorbance measurements (at 663 nm) of methanol extracts from 1-ml culture aliquots and calculated according to Lichtenthaler (Lichtenthaler, 1987). Total cell spectra were obtained from 1-ml aliquots of cultures in exponential growth phase, which were diluted to $OD_{730}$=0.3, and the obtained spectra were normalized to that of Chl α ($OD_{663}$). Doubling times were calculated using the exponential regression curve fitting online tool available at website doubling-time.com/compute.php. All measurements were performed at least in triplicate from aliquots from different cultures (using the same inoculum from a BG-11 agar plate). All measurements were performed in a Nanodrop2000C spectrophotometer (Thermo Scientific, USA).

PCR and Immunoblot Analysis

Standard PCR was performed as described in the manufacturer's protocol using EconoTaq Plus Green 2X (Lucigen, USA) and gene-specific primer pairs (Table 2). For protein extraction, pellets from 50 ml culture aliquots were resuspended in 1 ml of lysis buffer (25 mM HEPES-NaOH pH 7, 15 mM $CaCl_2$, 5 mM $MgCl_2$, 15% Glycerol, 200 μM PMSF and cOmplete, Mini protease inhibitor (Roche)) and broken in a BeadBug homogenizer (Biospec Products, USA), by beating for 6 cycles of 30 seconds and 2 minutes of incubation in ice between each cycle. After 20 minutes of centrifugation at 20000 rcf, 15-μl aliquots plus SDS loading dye were loaded onto an acrylamide gel (without boiling the sample) for SDS-PAGE. SDS-PAGE and immunoblot analysis were performed according to the manufacturer's protocol (BioRad's bulletin 6376) using a polyclonal antibody from rabbit against Syn 7942 CcmM (dilution 1:5000) (Rothamstead Research, UK) as a primary antibody and Goat Anti-Rabbit IgG-HRP (Dilution 1:7000) (Life Tech. #656120) as secondary antibody and 1-Step Ultra TMB-Blotting Solution as substrate (Thermo #37574). For densitometries, total protein extract samples from three independent cultures were normalized according to the peak absorbance at 663 nm, loaded at four decreasing serial dilutions, and blotted as described using Anti-RbcL antibody (Agrisera Cat. AS03 037) at a dilution of 1:10000. Densitometry measurements were performed on the different immunoblots using ImageJ software (Schneider et al., 2012).

Oxygen Evolution

Two-ml aliquots were harvested from exponential-phase cultures, supplemented with 10 mM bicarbonate prior to the measurement, and the steady-state rate of oxygen evolution was determined at saturating light intensity (950 moles photons $m^{-2}s^{-1}$) and 30° C. using an LMI-6000 illuminator (Dolan-Jenner, USA) and an Oxygraph Plus Clark-type electrode (Hansatech, UK).

Fluorescence and Electron Microscopy

Cultures grown to $OD_{730}$=0.5 in 3% $CO_2$ were transferred to air and grown overnight. For fluorescence microscopy, 1-ml aliquots were concentrated by centrifugation (1500 rcf for 5 minutes and resuspended in 100 μl of BG11) and visualized (autofluorescence and GFP) using a Zeiss Axio Observer.D1 inverted microscope. For electron microscopy, pellets from 50-ml aliquots were chemically fixed with 2% glutaraldehyde in 50 mM phosphate buffer for 2 hours at room temperature, followed by 1% osmium tetroxide for 2 hours at room temperature, and block stained with 2% aqueous uranyl acetate overnight at 4° C. Cells were dehydrated in an increasing acetone series (2 minutes at 37° C.; 20% acetone increments) and embedded in Spurr's resin (15 minutes at 37° C.; 25% increments) using an MS-9000 Laboratory Microwave Oven (Electron Microscopy Science, USA). Sections (70 nm thick) were cut on a MYX ultramicrotome (RMC Products, USA), positively stained with 6% uranyl acetate and Reynolds lead citrate (Reynolds, 1963) and visualized on a JEM 100CX II transmission electron microscope (JEOL) equipped with an Orius SC200-830 CCD camera (Gatan Inc., USA).

Quantum Efficiency of Photosystem II $F_v/F_m$ was determined in triplicate using 4-ml culture aliquots from biological replicates at exponential phase in cells dark adapted for three minutes as described previously (Cameron et al., 2013). Briefly, aliquots were diluted with BG-11 immediately before dark adaptation to a chlorophyll concentration of ~1-2 μg/ml and measured using an Aqua-pen AP100 (Photon Systems Instruments, Czech Republic). Measurement started at time=0 h when the cultures were transferred from 3% $CO_2$ to air.

Sequences

Sequences can be found in the GenBank/EMBL data libraries. For example, an amino acid sequence for a *Synechococcus elongatus* PCC 7942 carbonate dehydratase (CcmM: Synpcc7942_1423) is available as accession number ABB57453 (SEQ ID NO:69).

```
  1  MPSPTTVPVA TAGRLAEPYI DPAAQVHAIA SIIGDVRIAA
 41  GVRVAAGVSI RADEGAPFQV GKESILQEGA VIHGLEYGRV
 81  LGDDQADYSV WIGQRVAITH KALIHGPAYL GDDCFVGFRS
121  TVFNARVGAG SVIMMHALVQ DVEIPPGRYV PSGAIITTQQ
161  QADRLPEVRP EDREFARHII GSPPVIVRST PAATADFHST
201  PTPSPLRPSS SEATTVSAYN GQGRLSSEVI TQVRSLLNQG
241  YRIGTEHADK RRFRTSSWQP CAPIQSTNER QVLSELENCL
281  SEHEGEYVRL LGIDTNTRSR VFEALIQRPD GSVPESLGSQ
321  PVAVASGGGR QSSYASVSGN LSAEVVNKVR NLLAQGYRIG
361  TEHADKRRFR TSSWQSCAPI QSSNERQVLA ELENCLSEHE
401  GEYVRLLGID TASRSRVFEA LIQDPQGPVG SAKAAAAPVS
441  SATPSSHSYT SNGSSSSDVA GQVRGLLAQG YRISAEVADK
481  RRFQTSSWQS LPALSGQSEA TVLPALESIL QEHKGKYVRL
521  IGIDPAARRR VAELLIQKP
```

An amino acid sequence for a *Synechococcus elongatus* PCC 7942 carbon dioxide concentrating mechanism protein (CcmN: Synpcc7942_1424) is available as accession number ABB57454 (SEQ ID NO:70).

```
  1  MHLPPLEPPI SDRYFASGEV TIAADVVIAP GVLLIAEADS
 41  RIEIASGVCI GLGSVIHARG GAIIIQAGAL LAAGVLIVGQ
 81  SIVGRQACLG ASTTLVNTSI EAGGVTAPGS LLSAETPPTT
121  ATVSSSEPAG RSPQSSAIAH PTKVYGKEQF LRMRQSMFPD
161  R
```

An amino acid sequence for a *Synechococcus elongatus* PCC 7942 Carbonate dehydratase (CcaA; Synpcc7942_1447) is available as accession number ABB57477.1 (SEQ ID NO:71).

```
  1  MRKLIEGLRH FRTSYYPSHR DLFEQFAKGQ HPRVLFITCS
 41  DSRIDPNLIT QSGMGELFVI RNAGNLIPPF GAANGGEGAS
 81  IEYAIAALNI EHVVVCGHSH CGAMKGLLKL NQLQEDMPLV
121  YDWLQHAQAT RRLVLDNYSG YETDDLVEIL VAENVLTQIE
161  NLKTYPIVRS RLFQGKLQIF GWIYEVESGE VLQISRTSSD
201  DTGIDECPVR LPGSQEKAIL GRCVVPLTEE VAVAPPEPEP
241  VIAAVAAPPA NYSSRGWLAP EQQQRIYRGN AS
```

Example 2: Design of a Chimeric Protein that Supports Native Core Assembly and Cell Growth in Air This Example describes construction of chimeric proteins that assemble into a carboxysome core.

The design took into consideration observations that proteins evolve via domain fusions that are reflective of protein-protein interactions. The inventors predicted the domain boundaries in the CcmM, CcmN and CcaA proteins from *Synechococcus elongatus* PCC 7942 (FIG. 1A) using InterPro (Hunter et al., 2012). Three chimeric genes were then constructed encoding proteins that could assemble into a carboxysome core:

1) a ccaA-M35 fusion construct, where the γ-CA domain (Pfam00132) of CcmM was replaced by β-CA (Pfam00484) (FIG. 1D);

2) a M35-EP fusion construct, where three SSLD domains (Pfam00101) and their native linkers were fused to the EP (FIG. 1E); and 3) M35-ccaA$_{(short)}$-EP fusion construct, containing three SSLDs and their native linkers, the β-CA, CcaA with a short segment of its C-terminal tail as a linker, and the EP from the C-terminus of CcmN (FIGS. 1B, 1F-1H).

A gene coding for a green fluorescent protein (GFP)-labeled large subunit of Rubisco (rbcL-GFP) was inserted into each strain for in vivo visualization of carboxysome formation by fluorescence microscopy (Savage et al., 2010). To test whether the chimeric proteins can assemble into a carboxysome core, the *Synechococcus elongatus* PCC 7942 ccmM and ccmN were replaced with selectable marker genes (COREΔ2/RbcL-GFP strain; hcr phenotype). The chimeric genes were then transformed via double homologous recombination to replace the selectable markers of the COREΔ2/RbcL-GFP strain (placing the genes under the same regulation of the ccm operon genes) using growth in air for positive selection. In the case of ccaA-M35, the ccmN gene was reintroduced in the same vector.

Only M35-ccaA$_{(short)}$-EP expression was able to rescue the hcr phenotype. This construct was named CcmC where the final "C" was for chimeric (FIG. 1H). The resulting strain (COREΔ2/CcmC/RbcL-GFP) contained the original ccaA in its genome. Therefore, to further substantiate the evident functional rescue by CcmC, the native ccaA was replaced with a gentamycin resistance gene (resulting in strain COREΔ3/CcmC/RbcL-GFP). This triple mutant strain was able to grow in air.

The presence or absence of ccmM, ccmN and ccaA was confirmed by PCR. Sequencing of the region between ccmL and ccmO further indicated that ccmC was integrated into the ccm operon. The CCM insertion site sequence is shown below (SEQ ID NO:72), where the ccmC DNA insert is identified in bold and with underlining, and the portion of the genomic ccmK2 gene disrupted by the ccmC DNA insert is shown in bold (at the beginning of the SEQ ID NO:72 sequence).

```
  1 AGCCGCGGCA GTCAAGCGCG CCATGTGCGC GATTGTCAGG
 41 AACGACCGGT TGATGCAGCT GTCATTGCCA TCATCGATAC
 81 GGTCAACGTG GAAAACCGCT CCGTCTACGA CAAACGCGAG
121 CACAGCTAAT GGGCAGGGAT TGAATCCCTG CTGGTCATTG
161 ATCTGGATTG AGCCCAGGCT TGGGAGGTTA GCATATGACC
201 GTGAGCGCTT ATAACGGCCA AGGCCGACTC AGTTCCGAAG
241 TCATCACCCA AGTCCGGAGT TTGCTGAACC AGGGCTATCG
281 GATTGGGACG GAACATGCGG ACAAGCGCCG CTTCCGGACT
321 AGCTCTTGGC AGCCCTGCGC GCCGATTCAA AGCACGAACG
```

```
-continued
 361 AGCGCCAGGT CTTGAGCGAA CTGGAAAATT GTCTGAGCGA
 401 ACACGAAGGT GAATACGTTC GCTTGCTCGG CATCGATACC
 441 AATACTCGCA GCCGTGTTTT TGAAGCCCTG ATTCAACGGC
 481 CCGATGGTTC GGTTCCTGAA TCGCTGGGGA GCCAACCGGT
 521 GGCAGTCGCT TCCGGTGGTG GCCGTCAGAG CAGCTATGCC
 561 AGCGTCAGCG GCAACCTCTC AGCAGAAGTG GTCAATAAAG
 601 TCCGCAACCT CTTAGCCCAA GGCTATCGGA TTGGGACGGA
 641 ACATGCAGAC AAGCGCCGCT TTCGGACTAG CTCTTGGCAG
 681 TCCTGCGCAC CGATTCAAAG TTCGAATGAG CGCCAGGTTC
 721 TGGCTGAACT GGAAAACTGT CTGAGCGAGC ACGAAGGTGA
 761 GTACGTTCGC CTGCTGGGCA TCGACACTGC TAGCCGCAGT
 801 CGTGTTTTTG AAGCCCTGAT CCAAGATCCC CAAGGACCGG
 841 TGGGTTCCGC CAAAGCGGCC GCCGCACCTG TGAGTTCGGC
 881 AACGCCCAGC AGCCACAGCT ACACCTCAAA TGGATCGAGT
 921 TCGAGCGATG TCGCTGGACA GGTTCGGGGT CTGCTAGCCC
 961 AAGGCTACCGGATCAGTGCG GAAGTCGCCG ATAAGCGTCG
1001 CTTCCAAACC AGCTCTTGGC AGAGTTTGCC GGCTCTGAGT
1041 GGCCAGAGCG AAGCAACTGT CTTGCCTGCT TTGGAGTCAA
1081 TTCTGCAAGA GCACAAGGGT AAGTATGTGC GCCTGATTGG
1121 GATTGACCCT GCGGCTCGTC GTCGCGTGGC TGAACTGTTG
1161 ATTCAAAAGC CGGGATCTCG CAAGCTCATC GAGGGGTTAC
1201 GGCATTTCCG TACGTCCTAC TACCCGTCTC ATCGGGACCT
1241 GTTCGAGCAG TTTGCCAAAG GTCAGCACCC TCGAGTCCTG
1281 TTCATTACCT GCTCAGACTC GCGCATTGAC CCTAACCTCA
1321 TTACCCAGTC GGGCATGGGT GAGCTGTTCG TCATTCGCAA
1361 CGCTGGCAAT CTGATCCCGC CCTTCGGTGC CGCCAACGGT
1401 GGTGAAGGGG CATCGATCGA ATACGCGATC GCAGCTTTGA
1441 ACATTGAGCA TGTTGTGGTC TGCGGTCACT CGCACTGCGG
1481 TGCGATGAAA GGGCTGCTCA AGCTCAATCA GCTGCAAGAG
1521 GACATGCCGC TGGTCTATGA CTGGCTGCAG CATGCCCAAG
1561 CCACCCGCCG CCTAGTCTTG GATAACTACA GCGGTTATGA
1601 GACTGACGAC TTGGTAGAGA TTCTGGTCGC CGAGAATGTG
1641 CTGACGCAGA TCGAAACCT TAAGACCTAC CCGATCGTGC
1681 GATCGCGCCT TTTCCAAGGC AAGCTGCAGA TTTTTGGCTG
1721 GATTTATGAA GTTGAAAGCG GCGAGGTCTT GCAGATTAGC
1761 CGTACCAGCA GTGATGACAC AGGCATTGAT GAATGTCCAG
1801 TGCGTTTGCC CGGCAGCCAG GAGAAAGCCA TTCTCGGTCG
1841 TTGTGTCGTC CCCCTGACCG AAGAAGTGGC CGTTGCTCCA
1881 CCAGAGCCGG AGCCTGTGAT CGCGGCTGTG GCGGCTCCAC
1921 CCGCCAACTA CTCCAGTCGC GGTTGGTTGG GATCTGGAGG
1961 CAGTGTCTAC GGCAAGGAAC AGTTTTTGCG GATGCGCCAG
2001 AGCATGTTCC CCGATCGCTA AGATGTGCAC AGCAGCTCTA
2041 GGAGCTGCAG GGTACT
```

The portion of the sequence of the ccmL gene at the ccmC integration site is shown below (SEQ ID NO:73).

```
  1 AGCCGCGGCA GTCAAGCGCG CCATGTGCGC GATTGTCAGG
 41 AACGACCGGT TGATGCAGCT GTCATTGCCA TCATCGATAC
 81 GGTCAACGTG GAAAACCGCT CCGTCTACGA CAAACGCGAG
121 CACAGCTAA
```

Figure 2:
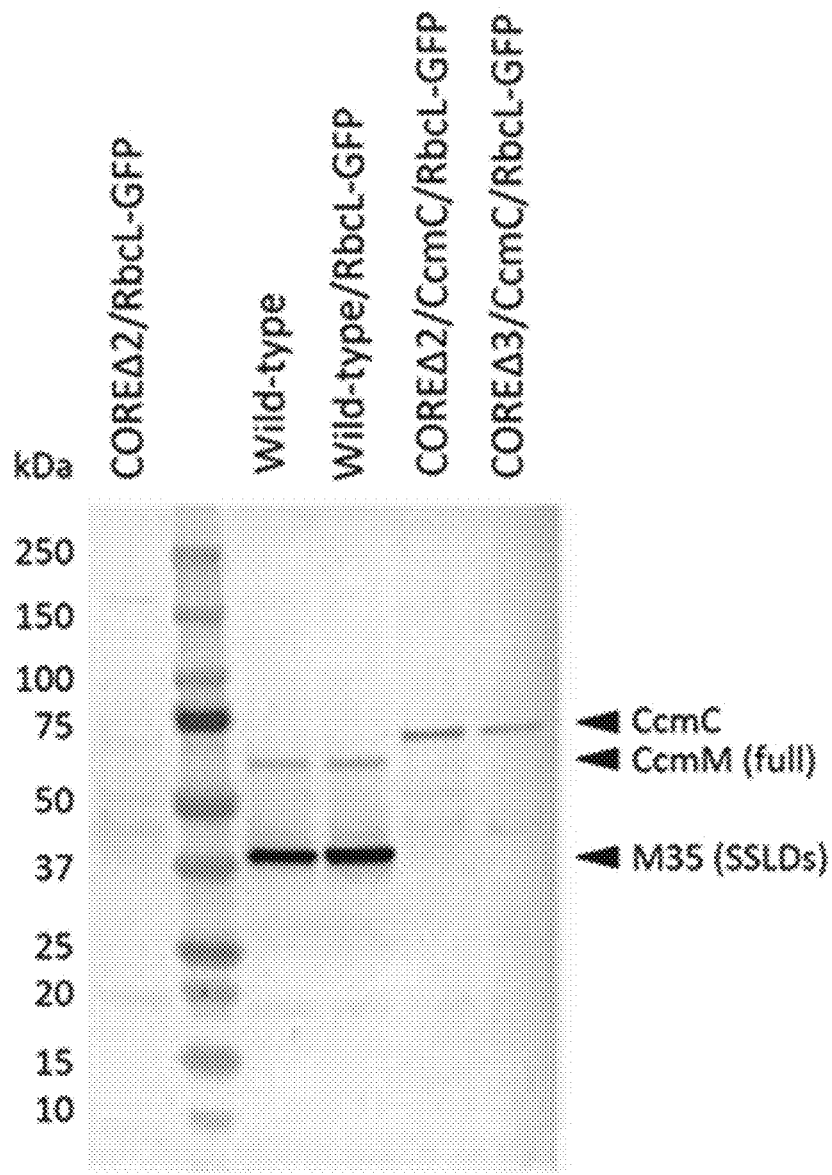
FIG. 2 illustrates cross-reactivity of the chimeric protein CcmC with anti-CcmM antibodies. Whole cell lysates were blotted and probed using anti-CcmM antibodies. Protein extracts from Controls (Wild-type background) show two bands corresponding to the full length and the short form of CcmM, while the mutants (CcmC background) show one band due to the cross-reactivity of the antibody with the small subunit-like domains.

Protein screening by immunoblot using polyclonal anti-CcmM antibodies showed no cross-reactivity with a total protein extract of the COREΔ2/RbcL-GFP strain, confirming the absence of those proteins (FIG. 2). In contrast, signals at ~37 kDa (major) and at ~63 kDa (minor) were observed in wild type and in the control strain expressing rbcL-GFP (hereafter Wild-type/RbcL-GFP strain), corresponding to the two forms of CcmM required for carboxysome assembly in Wild-type Syn 7942 carboxysomes (corresponding to M35 and full-length CcmM (So et al., 2002b; Long et al., 2010). These two bands are absent in the COREΔ2/CcmC/RbcL-GFP and COREΔ3/CcmC/RbcL-GFP strains, and replaced by cross-reactivity at ~75 kDa, corresponding to the fusion protein (predicted mass of 67 kDa; FIG. 2).

Example 3: CcmC Replaces Four Proteins of the β-carboxysome Core

This Example illustrates assembly of CcmC into functioning carboxysomes.

Figure 3:
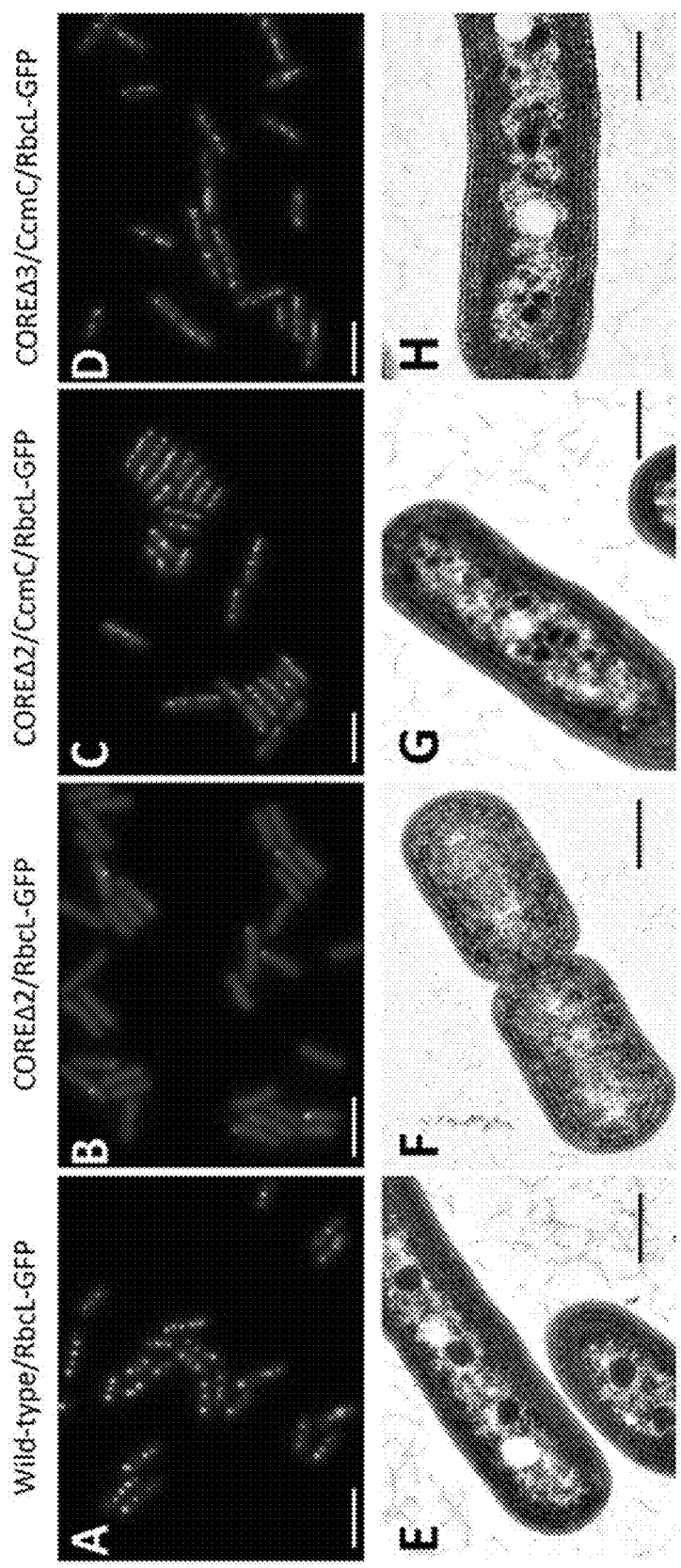
FIG. 3 illustrates structural complementation of the carboxysome core deletion strains with the chimeric protein CcmC.

Fluorescence and transmission electron microscopy were used to assay for formation of carboxysomes (FIG. 3). In the wild-type/RbcL-GFP strain, the carboxysomes were in the typical arrangement, along the longitudinal axes of the cells (FIG. 3 panel A). RbcL-GFP in the COREΔ2/RbcL-GFP strain was diffuse throughout the cell, as expected for strains lacking carboxysomes (Cameron et al., 2013) (FIG. 3 panel B). Occasional polar foci (n=150/556) were observed. Such polar foci may be due to misfolded and aggregated labeled protein. For example, polar localization of protein aggregates (Rokney et al., 2009) and false foci (Landgraf et al., 2012) have been observed in *E. coli*. Such foci may also be due to interaction with the remaining gene products of the carboxysome operon. They are not indicative of carboxysome formation, as the COREΔ2/RbcL-GFP strain has an her phenotype (i.e., a high $CO_2$-requiring phenotype).

In contrast, abundant GFP-labeled carboxysomes were observed in the mutant strains COREΔ2/CcmC/RbcL-GFP and COREΔ3/CcmC/RbcL-GFP (FIG. 3 panels C and D, respectively). Although occasionally clustered, the carboxysomes still localized along the longitudinal axis of the cell (FIG. 3 panels C and D, respectively).

The average carboxysome number (fluorescent puncta across the longitudinal plane) per cell in the wild-type/RbcL-GFP strain was 3.7±1.1 (FIG. 4A). The average carboxysome number was somewhat higher in the COREΔ2/CcmC/RbcL-GFP strain (average 6.4±1.8) and in the COREΔ3/CcmC/RbcL-GFP strain (average 6.4±2.0) (FIG. 4A).

The amount of Rubisco protein per mg Chlorophyll a (Chl α) protein in the different strains was compared by immunoblotting using antibodies against the large subunit RbcL. Both COREΔ2/CcmC/RbcL-GFP and COREΔ3/CcmC/RbcL-GFP strains contained more than a 2-fold increase in RbcL relative to the Wild-type/RbcL strain (FIG. 4B).

Analysis by transmission electron microscopy further confirmed carboxysome formation of native (FIG. 3 panel E) and streamlined carboxysomes (FIG. 3 panels G and H).

The chimeric carboxysomes were smaller than wild type carboxysomes. As illustrated in FIG. 4C, the average carboxysome diameter for wild-type/RbcL-GFP carboxysomes was 185±28 nm, but the average diameter of COREΔ2/CcmC carboxysomes was 103±25 nm and the average diameter of COREΔ3/CcmC carboxysomes was 95±19 nm. In addition, the CcmC strains typically had more carboxysomes and the CcmC carboxysomes tended to be more clustered compared to the wild-type carboxysomes.

Abnormally shaped carboxysomes were occasionally observed ("rod carboxysomes") in the CcmC strains but these have also been observed in wild type cyanobacteria (Gantt and Conti, 1969). Researchers have proposed that such rod carboxysomes may be a type of intermediate during carboxysome formation (Chen et al., 2013). Based on studies by the inventors, these rod carboxysomes could also be indicative of a deficiency in CA activity, as carboxysome aggregation and morphological variation were observed in the control strain ΔCcaA/RbcL-GFP (data not shown).

To determine if the reengineered carboxysomes function comparably to the Wild-type/RbcL-GFP carboxysomes, the growth of cells was analyzed at the exponential growth phase under high $CO_2$ (5%) and low $CO_2$ (air) conditions. No growth difference was observed between the strains when incubated in high $CO_2$ (FIG. 5B), because under these conditions, cyanobacterial $CO_2$ fixation does not depend upon proper carboxysome formation. As expected, the COREΔ2/RbcL-GFP strain (without the CcmC construct) failed to grow in air, whereas in air the other strains were able to grow (FIG. 5A). The COREΔ2/CcmC/RbcL-GFP strain had the fastest doubling time among the reengineered strains tested, while the growth rates of COREΔ3/CcmC/RbcL-GFP and the Wild-type/RbcL-GFP strain are comparable (FIG. 5A-5B).

Example 4: Physiology of a Cyanobacterial Strain with a Streamlined Carboxysome

This Example illustrates some of the physiological characteristics of a triple deletion strain containing carboxysomes with synthetic cores (COREΔ3/CcmC/RbcL-GFP).

Figure 6A:
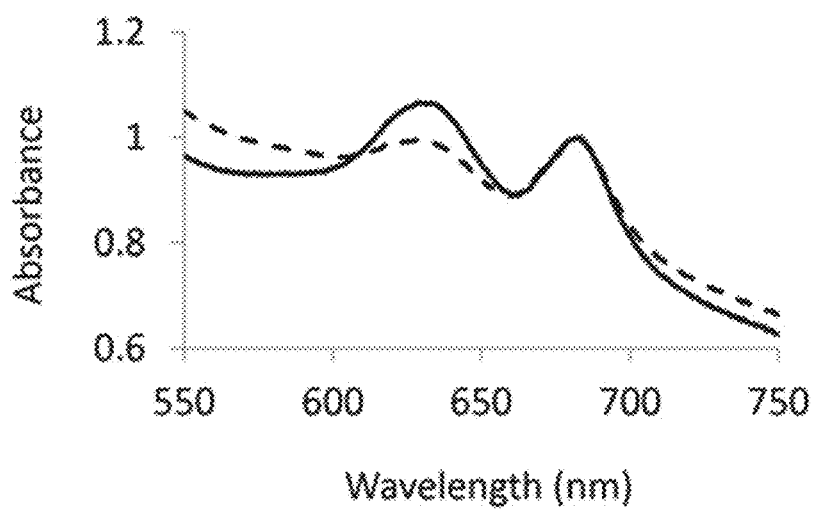
FIG. 6A-6C illustrate physiological parameters of wild-type vs. CcmC strains.

The COREΔ3/CcmC/RbcL-GFP strain has pigmentation differences when compared to Wild-type/RbcL-GFP (FIG. 6A). Such a difference could be attributed to decreased phycobilisome content.

The relative photosynthetic capacities of photosystem II were measure through quantification of chlorophyll fluorescence in dark adapted cells ($F_v/F_m$) upon transfer of the cultures from 3% $CO_2$ to air (FIG. 6B) The $F_v/F_m$ is widely used as a measure of the efficiency of the photosynthetic electron transport chain, which generates the ATP and reducing power that is consumed by the Calvin-Benson-Bassham (CBB) cycle (Baker, 2008). Accordingly, $F_v/F_m$ has been used as a proxy for carboxysome function. For example, carboxysome-deficient strains of Syn 7942 have an $F_v/F_m$ approximating zero in 3% $CO_2$ (Cameron et al., 2013).

Figure 6B:
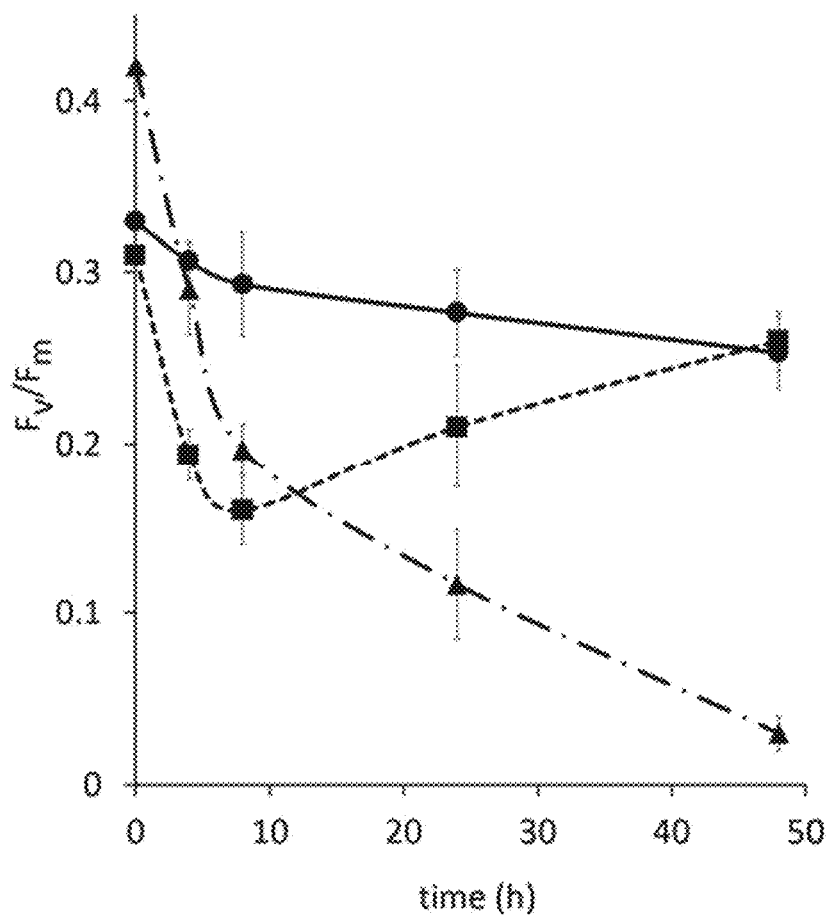

As illustrated in FIG. 6B, while the $F_v/F_m$ of Wild-type/RbcL-GFP remains relatively constant (solid line), a sharp decrease in $F_v/F_m$ relative to the high-$CO_2$ values is observed in both mutant core strains. The $F_v/F_m$ in the COREΔ2/RbcL-GFP control strain declined towards zero and did not recover (dashed, dotted line in FIG. 6B). However, the COREΔ3/CcmC/RbcL-GFP strain (dashed line in FIG. 6B) adapted within about 10 hr after the $CO_2$ step-down and eventually reached the same fluorescence levels as the wild-type/RbcL-GFP strain.

Figure 6C:
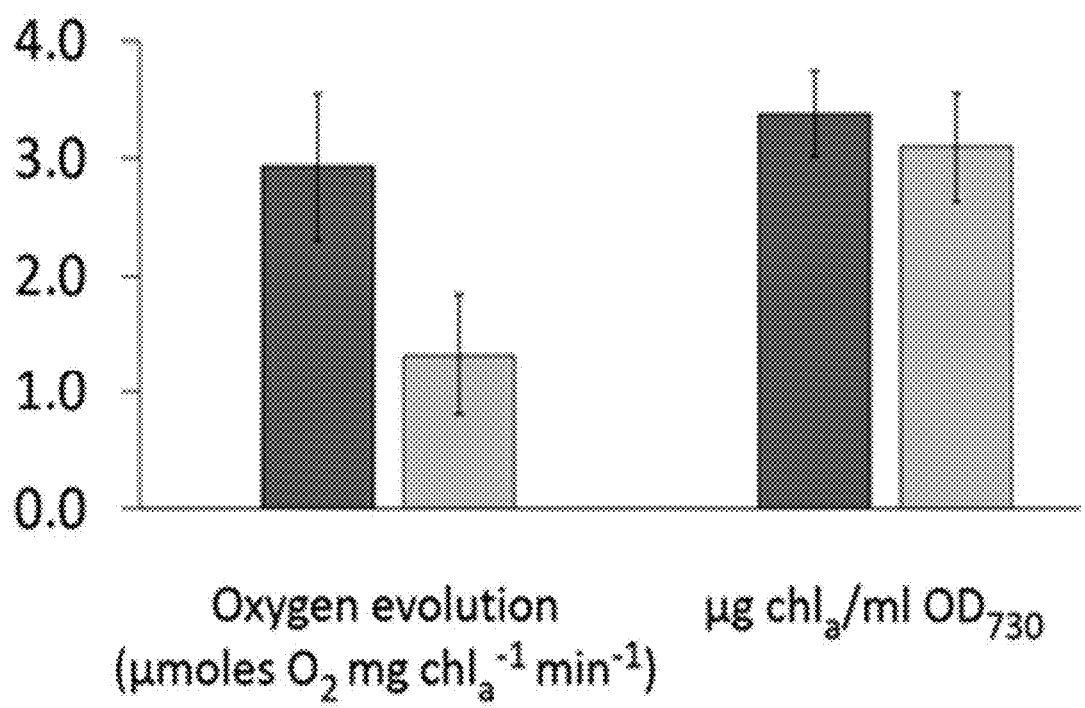

As an additional, complementary measure of photosynthetic activity, the oxygen evolution rates of air-grown cultures were compared at high light intensity (950 μmoles photons $m^{-2}$ $s^{-1}$). As shown in FIG. 6C, the wild-type/RbcL-GFP cells (dark gray bar) produced more oxygen than the COREΔ3/CcmC/RbcL-GFP strain (light gray bar) The amounts of oxygen produced by the wild-type/RbcL-GFP cells was 2.9±1.0 μmoles $O_2$ μg $Chl_a^{-1}$ $min^{-1}$ compared to 1.3±0.5 μmoles $O_2$ μg $Chl_a^{-1}$ $min^{-1}$ for the COREΔ3/CcmC/RbcL-GFP.

These results indicate that the altered composition of the core has a net effect on the physiology of the cell relative to the Wild-type/RbcL-GFP control. Nevertheless, the reengineered core is immediately able to effectively support functional carboxysome assembly (FIG. 3 panels C and D) and photosynthesis (FIG. 5A-5B).

REFERENCES

Aussignargues, C., Paasch, B. C., Gonzalez-Esquer, R., Erbilgin, O., and Kerfeld, C. A. (2015). Bacterial microcompartment assembly: The key role of encapsulation peptides. *Communicative & Integrative Biology*, 8(3), e1039755.

Axen, S. D., Erbilgin, O., and Kerfeld, C. A. (2014). A taxonomy of bacterial microcompartment loci constructed by a novel scoring method. PLoS Comput. Biol. 10, e1003898.

Baker, N. R. (2008). Chlorophyll fluorescence: A probe of photosynthesis in vivo. Annu. Rev. Plant Biol. 59, 89-113.

Biasini, M., Bienert, S., Waterhouse, A., Arnold, K., Studer, G., Schmidt, T., Kiefer, F., Cassarino, T. G., Bertoni, M., Bordoli, L., and Schwede, T. (2014). SWISS-MODEL: modelling protein tertiary and quaternary structure using evolutionary information. Nucleic Acids Res. 42, W252-W258.

Cai, F., Menon, B. B., Cannon, G. C., Curry, K. J., Shively, J. M., and Heinhorst, S. (2009). The pentameric vertex proteins are necessary for the icosahedral carboxysome shell to function as a $CO_2$ leakage barrier. PLoS ONE 4, e7521.

Cai, F., Dou, Z., Bernstein, S., Leverenz, R., Williams, E., Heinhorst, S., Shively, J., Cannon, G., and Kerfeld, C. (2015). Advances in understanding carboxysome assembly in *Prochlorococcus* and *Synechococcus* implicate CsoS2 as a critical component. Life 5, 1141-1171.

Cai, F., Bernstein, S. L., Wilson, S. C., & Kerfeld, C. A. (2016). Production and Characterization of Synthetic Carboxysome Shells with Incorporated Luminal Proteins. *Plant Physiology*, 170(3), 1868-1877.

Cameron, Jeffrey C., Wilson, Steven C., Bernstein, Susan L., and Kerfeld, Cheryl A. (2013). Biogenesis of a bacterial organelle: The carboxysome assembly pathway. Cell 155, 1131-1140.

Chen, A. H., Robinson-Mosher, A., Savage, D. F., Silver, P. A., and Polka, J. K. (2013). The bacterial carbon-fixing organelle is formed by shell envelopment of preassembled cargo. PLoS ONE 8, e76127.

Cheng, S., Liu, Y., Crowley, C. S., Yeates, T. O., and Bobik, T. A. (2008). Bacterial microcompartments: their properties and paradoxes. BioEssays 30, 1084-1095.

Dragosits, M., and Mattanovich, D. (2013). Adaptive laboratory evolution—principles and applications for biotechnology. Microb. Cell Fact. 12, 64.

Drews, G., and Niklowitz, W. (1956). [Cytology of Cyanophycea. II. Centroplasm and granular inclusions of *Phormidium uncinatum*]. Archiv fur Mikrobiologie 24, 147-162.

Frank, S., Lawrence, A. D., Prentice, M. B., and Warren, M. J. (2013). Bacterial microcompartments moving into a synthetic biological world. J. Biotechnol. 163, 273-279.

Gantt, E., and Conti, S. F. (1969). Ultrastructure of Blue-Green Algae. J. Bacteriol. 97, 1486-1493.

Hunter, S., Jones, P., Mitchell, A., Apweiler, R., Attwood, T. K., Bateman, A., Bernard, T., Binns, D., Bork, P., Burge, S., de Castro, E., Coggill, P., Corbett, M., Das, U., Daugherty, L., Duquenne, L., Finn, R. D., Fraser, M., Gough, J., Haft, D., Hulo, N., Kahn, D., Kelly, E., Letunic, I., Lonsdale, D., Lopez, R., Madera, M., Maslen, J., McAnulla, C., McDowall, J., McMenamin, C., Mi, H., Mutowo-Muellenet, P., Mulder, N., Natale, D., Orengo, C., Pesseat, S., Punta, M., Quinn, A. F., Rivoire, C., Sangrador-Vegas, A., Selengut, J. D., Sigrist, C. J., Scheremetjew, M., Tate, J., Thimmajanarthanan, M., Thomas, P. D., Wu, C. H., Yeats, C., and Yong, S. Y. (2012). InterPro in 2011: new developments in the family and domain prediction database. Nucleic Acids Res. 40, D306-312.

Kerfeld, C. A., and Erbilgin, O. (2015). Bacterial microcompartments and the modular construction of microbial metabolism. Trends Microbiol. 23, 22-34.

Kinney, J. N., Salmeen, A., Cai, F., and Kerfeld, C. A. (2012). Elucidating essential role of conserved carboxysomal protein CcmN reveals common feature of bacterial microcompartment assembly. J. Biol. Chem. 287, 17729-17736.

Kufryk, G. I., Sachet, M., Schmetterer, G., and Vermaas, W. F. (2002). Transformation of the cyanobacterium *Synechocystis* sp. PCC 6803 as a tool for genetic mapping: optimization of efficiency. FEMS Microbiol. Lett. 206, 215-219.

Lagarde, D., Beuf, L., and Vermaas, W. (2000). Increased production of zeaxanthin and other pigments by application of genetic engineering techniques to *Synechocystis* sp. Strain PCC 6803. Appl. Environ. Microbiol. 66, 64-72.

Landgraf, D., Okumus, B., Chien, P., Baker, T. A., and Paulsson, J. (2012). Segregation of molecules at cell division reveals native protein localization. Nat. Methods 9, 480-482.

Lawrence, A. D., Frank, S., Newnham, S., Lee, M. J., Brown, I. R., Xue, W.-F., Rowe, M. L., Mulvihill, D. P., Prentice, M. B., Howard, M. J., and Warren, M. J. (2014). Solution structure of a bacterial microcompartment targeting peptide and its application in the construction of an ethanol bioreactor. ACS Synth. Biol. 3, 454-465.

Lichtenthaler, H. K. (1987). Chlorophylls and carotenoids: Pigments of photosynthetic biomembranes. Methods Enzymol. 148, 350-382.

Lin, M. T., Occhialini, A., Andralojc, P. J., Parry, M. A. J., and Hanson, M. R. (2014a). A faster Rubisco with potential to increase photosynthesis in crops. Nature 513, 547-550.

Lin, M. T., Occhialini, A., Andralojc, P. J., Devonshire, J., Hines, K. M., Parry, M. A. J., and Hanson, M. R. (2014b). β-Carboxysomal proteins assemble into highly organized structures in *Nicotiana* chloroplasts. Plant J. 79, 1-12.

Lluch-Senar, M., Delgado, J., Chen, W. H., Lloréns-Rico, V., O'Reilly, F. J., Wodke, J. A., Unal, E. B., Yus, E., Martínez, S., Nichols, R. J., Ferrar, T., Vivancos, A., Schmeisky, A., Stülke, J., van Noort, V., Gavin, A. C., Bork, P., and Serrano, L. (2015). Defining a minimal cell: essentiality of small ORFs and ncRNAs in a genome-reduced bacterium. Mol. Syst. Biol. 11, 780.

Long, B. M., Badger, M. R., Whitney, S. M., and Price, G. D. (2007). Analysis of carboxysomes from *Synechococcus* PCC7942 reveals multiple Rubisco complexes with carboxysomal proteins CcmM and CcaA. J. Biol. Chem. 282, 29323-29335.

Long, B. M., Tucker, L., Badger, M. R., and Price, G. D. (2010). Functional cyanobacterial β-carboxysomes have an absolute requirement for both long and short forms of the CcmM protein. Plant Physiol. 153, 285-293.

Marsh, Joseph A., Hernandez, H., Hall, Z., Ahnert, Sebastian E., Perica, T., Robinson, Carol V., and Teichmann, Sarah A. (2013). Protein complexes are under evolutionary selection to assemble via ordered pathways. Cell 153, 461-470.

Pella, K. L., Castel, S. E., de Araujo, C., Espie, G. S., and Kimber, M. S. (2010). Structural basis of the oxidative activation of the carboxysomal γ-carbonic anhydrase, CcmM. Proc. Natl. Acad. Sci. 107, 2455-2460.

Pettersen, E. F., Goddard, T. D., Huang, C. C., Couch, G. S., Greenblatt, D. M., Meng, E. C., and Ferrin, T. E. (2004). UCSF Chimera—A visualization system for exploratory research and analysis. J. Comput. Chem. 25, 1605-1612.

Price, G. D., and Badger, M. R. (1989). Isolation and characterization of high $CO_2$-requiring-mutants of the cyanobacterium *Synechococcus* PCC7942: Two phenotypes that accumulate inorganic carbon but are apparently unable to generate $CO_2$ within the carboxysome. Plant Physiol. 91, 514-525.

Price, G. D., Badger, M. R., Woodger, F. J., and Long, B. M. (2008). Advances in understanding the cyanobacterial CO2-concentrating-mechanism (CCM): functional components, Ci transporters, diversity, genetic regulation and prospects for engineering into plants. J. Exp. Bot. 59, 1441-1461.

Price, G. D., Pengelly, J. J. L., Forster, B., Du, J., Whitney, S. M., von Caemmerer, S., Badger, M. R., Howitt, S. M., and Evans, J. R. (2013). The cyanobacterial CCM as a source of genes for improving photosynthetic $CO_2$ fixation in crop species. J. Exp. Bot. 64, 753-768.

Reynolds, E. S. (1963). The use of lead citrate at high pH as an electron-opaque stain in electron microscopy. J. Cell Biol. 17, 208-212.

Rippka, R., Deruelles, J., Waterbury, J. B., Herdman, M., and Stanier, R. Y. (1979). Generic assignments, strain histories and properties of pure cultures of cyanobacteria. J. Gen. Microbiol. 111, 1-61.

Rokney, A., Shagan, M., Kessel, M., Smith, Y., Rosenshine, I., and Oppenheim, A. B. (2009). *E. coli* transports aggregated proteins to the poles by a specific and energy-dependent process. J. Mol. Biol. 392, 589-601.

Sambrook, J., and Russell, D. W. (2001). Molecular cloning: a laboratory manual. (CSHL Press).

Savage, D. F., Afonso, B., Chen, A. H., and Silver, P. A. (2010). Spatially ordered dynamics of the bacterial carbon fixation machinery. Science 327, 1258-1261.

Schneider, C. A., Rasband, W. S., and Eliceiri, K. W. (2012). NIH Image to ImageJ: 25 years of image analysis. Nat. Methods 9, 671-675.

So, A. K.-C., Cot, S. S.-W., and Espie, G. S. (2002a). Characterization of the C-terminal extension of carboxysomal carbonic anhydrase from *Synechocystis* sp. PCC6803. Funct. Plant Biol. 29, 183-194.

So, A. K. C., John-McKay, M., and Espie, G. S. (2002b). Characterization of a mutant lacking carboxysomal carbonic anhydrase from the cyanobacterium *Synechocystis* PCC6803. Planta 214, 456-467.

Takahashi, S., and Murata, N. (2005). Interruption of the Calvin cycle inhibits the repair of Photosystem II from photodamage. Biochim. Biophys. Acta 1708, 352-361.

Zarzycki, J., Axen, S. D., Kinney, J. N., and Kerfeld, C. A. (2013). Cyanobacterial-based approaches to improving photosynthesis in plants. J. Exp. Bot. 64, 787-798.

All patents and publications referenced or mentioned herein are indicative of the levels of skill of those skilled in the art to which the invention pertains, and each such referenced patent or publication is hereby specifically incorporated by reference to the same extent as if it had been incorporated by reference in its entirety individually or set forth herein in its entirety. Applicants reserve the right to physically incorporate into this specification any and all materials and information from any such cited patents or publications.

The following statements are intended to describe and summarize various embodiments of the invention according to the foregoing description in the specification.

Statements:

1. A fusion protein comprising at least two small subunit-like domains (SSLDs), at least one carbonic anhydrase (CA) domain, and at least one encapsulation peptide (EP).
2. The fusion protein of statement 1, wherein the at least one carbonic anhydrase (CA) domain is flanked on one side by the at least two small subunit-like domains (SSLDs), and by the at least one encapsulation peptide (EP) on the other side.
3. The fusion protein of statement 1 or 2, wherein the at least two small subunit-like domains (SSLDs) comprise scaffolding domains that can bind or nucleate with ribulose-1,5-bisphosphate carboxylase/oxygenase (Rubisco).
4. The fusion protein of statement 1, 2, or 3, wherein the at least two small subunit-like domains (SSLDs) can nucleate with ribulose-1,5-bisphosphate carboxylase/oxygenase (Rubisco), and the Rubisco can synthesize 3-phosphoglycerate (3-PGA).
5. The fusion protein of statement 1-3, or 4, wherein the at least two small subunit-like domains (SSLDs) comprise at least 40% sequence identity, or at least 50% sequence identity, or at least 60% sequence identity, or at least 70% sequence identity, or at least 80% sequence identity, or at least 90% sequence identity, or at least 95% sequence identity, or at least 96% sequence identity, or at least 97% sequence identity, or at least 98% sequence identity, or at least 99% sequence identity, or 60-99% sequence identity, or 70-99% sequence identity, or 80-99% sequence identity, or 90-95% sequence identity, or 90-99% sequence identity, or 95-97% sequence identity, or 97-99% sequence identity, or 100% sequence identity (or complementarity) with any of SEQ ID NOs:1-11, 37, 75, 76, or 77.
6. The fusion protein of statement 1-4 or 5, wherein the at least two small subunit-like domains (SSLDs) comprise at least 40% sequence identity, or at least 50% sequence identity, or at least 60% sequence identity, or at least 70% sequence identity, or at least 80% sequence identity, or at least 90% sequence identity, or at least 95% sequence identity, or at least 96% sequence identity, or at least 97% sequence identity, or at least 98% sequence identity, or at least 99% sequence identity, or 60-99% sequence identity, or 70-99% sequence identity, or 80-99% sequence identity, or 90-95% sequence identity, or 90-99% sequence identity, or 95-97% sequence identity, or 97-99% sequence identity, or 100% sequence identity (or complementarity) with any of SEQ ID NOs:5-11, 37, 75, 76, or 77.
7. The fusion protein of statement 1-5 or 6, wherein the at least one carbonic anhydrase domain converts bicarbonate to carbon dioxide.
8. The fusion protein of statement 1-6 or 7, wherein the at least one carbonic anhydrase domain comprises at least 40% sequence identity, or at least 50% sequence identity, or at least 60% sequence identity, or at least 70% sequence identity, or at least 80% sequence identity, or at least 90% sequence identity, or at least 95% sequence identity, or at least 96% sequence identity, or at least 97% sequence identity, or at least 98% sequence identity, or at least 99% sequence identity, or 60-99% sequence identity, or 70-99% sequence identity, or 80-99% sequence identity, or 90-95% sequence identity, or 90-99% sequence identity, or 95-97% sequence identity, or 97-99% sequence identity, or 100% sequence identity with any of SEQ ID NOs:17-21 or 71.
9. The fusion protein of statement 1-7 or 8, wherein the at least one encapsulation peptide interacts with and/or binds one or more carboxysome shell protein.
10. The fusion protein of statement 1-8 or 9, wherein the at least one encapsulation peptide comprises at least 40% sequence identity, or at least 50% sequence identity, or at least 60% sequence identity, or at least 70% sequence identity, or at least 80% sequence identity, or at least 90% sequence identity, or at least 95% sequence identity, or at least 96% sequence identity, or at least 97% sequence identity, or at least 98% sequence identity, or at least 99% sequence identity, or 60-99% sequence identity, or 70-99% sequence identity, or 80-99% sequence identity, or 90-95% sequence identity, or 90-99% sequence identity, or 95-97% sequence identity, or 97-99% sequence identity, or 100% sequence identity (or complementarity) with any of SEQ ID NOs:12-16.
11. An expression cassette comprising a promoter operably linked to a nucleic acid segment encoding the fusion protein of statement 1-9 or 10.
12. The expression cassette of statement 11, wherein the promoter is a constitutive promoter, inducible promoter, regulated promoter, cell specific promoter, or synthetic promoter.
13. The expression cassette of statement 11 or 12, wherein the promoter is active before or during log phase growth of cells comprising the expression cassette.
14. The expression cassette of statement 11, 12, or 13, wherein the promoter is active after log phase growth of cells comprising the expression cassette.
15. The expression cassette of statement 11-13 or 14, wherein the nucleic acid segment encoding the fusion protein comprises at least 40% sequence identity, or at least 50% sequence identity, or at least 60% sequence identity, or at least 70% sequence identity, or at least 80% sequence identity, or at least 90% sequence identity, or at least 95% sequence identity, or at least 96% sequence identity, or at least 97% sequence identity, or at least 98% sequence identity, or at least 99% sequence identity, or 60-99% sequence identity, or 70-99% sequence identity, or 80-99% sequence identity, or 90-95% sequence identity, or 90-99% sequence identity, or 95-97% sequence identity, or 97-99% sequence identity, or 100% sequence identity (or complementarity) with any of SEQ ID NOs:26-29.
16. A cell comprising the expression cassette of statement 11-14 or 15.
17. An expression vector comprising the expression cassette of statement 11-14 or 15.
18. A cell comprising the expression vector of statement 16.
19. An organism comprising the fusion protein of statement 1-9 or 10.
20. An organism comprising a nucleic acid segment encoding the fusion protein of statement 1-9 or 10.
21. An organism comprising the expression cassette of statement 11-15, or the expression vector of statement 17.
22. A method comprising expressing the fusion protein of statement 1-9 or 10 in a cell.
23. A method comprising expressing the fusion protein of statement 1-9 or 10 from a nucleic acid in a cell.
24. A method comprising expressing the fusion protein of statement 1-9 or 10 from a heterologous nucleic acid in a cell.
25. A method comprising expressing a fusion protein encoded by the expression cassette of statement 11-14 or 15 in a cell.
26. A method for carbon fixation comprising expressing the fusion protein of statement 1-9 or 10 in a cell.
27. The method of statement 26, wherein the cell is a cyanobacteria, a bacteria, a plant cell, or an algae (e.g., a microalgae).
28. A method for carbon fixation comprising culturing a cell comprising the expression cassette of statement 11-14 or 15.
29. The method of statement 28, wherein the cell is a cyanobacteria, a bacteria, a plant cell, or an algae (e.g., a microalgae).
30. A method for oxygen evolution comprising culturing a cell comprising the expression cassette of statement 11-14 or 15.
31. A method comprising culturing a cell that can express the fusion protein of statement 1-9 or 10, and that can synthesize a product selected from a carbohydrate, sugar, protein, fatty acid, oil, biomass, alcohol, isobutyraldehyde, butanol, ethanol, propanediol, or isoprene.
32. The method of statement 31, wherein the cell is a cyanobacteria, a bacteria, a plant cell, or an algae (e.g., a microalgae).

The specific compositions and methods described herein are representative, exemplary and not intended as limitations on the scope of the invention. Other objects, aspects, and embodiments will occur to those skilled in the art upon consideration of this specification, and are encompassed within the spirit of the invention as defined by the scope of the claims. It will be readily apparent to one skilled in the art that varying substitutions and modifications may be made to the invention disclosed herein without departing from the scope and spirit of the invention. The terms and expressions that have been employed are used as terms of description and not of limitation, and there is no intent in the use of such terms and expressions to exclude any equivalent of the features shown and described or portions thereof, but it is recognized that various modifications are possible within the scope of the invention as claimed. Thus, it will be understood that although the present invention has been specifically disclosed by embodiments and optional features, modification and variation of the concepts herein disclosed may be resorted to by those skilled in the art, and that such modifications and variations are considered to be within the scope of this invention as defined by the appended claims and statements of the invention.

The invention illustratively described herein may be practiced in the absence of any element or elements, or limitation or limitations, which is not specifically disclosed herein as essential. The methods and processes illustratively described herein may be practiced in differing orders of steps, and the methods and processes are not necessarily restricted to the orders of steps indicated herein or in the claims.

As used herein and in the appended claims, the singular forms "a," "an," and "the" include plural reference unless the context clearly dictates otherwise. Thus, for example, a reference to "a plant" or "a seed" or "a cell" includes a plurality of such plants, seeds or cells, and so forth. In this document, the term "or" is used to refer to a nonexclusive or, such that "A or B" includes "A but not B," "B but not A," and "A and B," unless otherwise indicated.

Under no circumstances may the patent be interpreted to be limited to the specific examples or embodiments or methods specifically disclosed herein. Under no circumstances may the patent be interpreted to be limited by any statement made by any Examiner or any other official or employee of the Patent and Trademark Office unless such statement is specifically and without qualification or reservation expressly adopted in a responsive writing by Applicants.

The invention has been described broadly and generically herein. Each of the narrower species and subgeneric groupings falling within the generic disclosure also form part of the invention. This includes the generic description of the invention with a proviso or negative limitation removing any subject matter from the genus, regardless of whether or not the excised material is specifically recited herein. In addition, where features or aspects of the invention are described in terms of Markush groups, those skilled in the art will recognize that the invention is also thereby described in terms of any individual member or subgroup of members of the Markush group.

The Abstract is provided to comply with 37 C.F.R. § 1.72(b) to allow the reader to quickly ascertain the nature and gist of the technical disclosure. The Abstract is submitted with the understanding that it will not be used to interpret or limit the scope or meaning of the claims.

What is claimed:

1. A fusion protein comprising a polypeptide comprising at least two fused small subunit-like domains (SSLDs) that can bind or nucleate with ribulose-1,5-bisphosphate carboxylase/oxygenase (Rubisco), each SSLD comprising at least 95% sequence identity to any of SEQ ID NO: 75, 76 or 77, one SSLD fused to at least one domain having carbonic anhydrase activity, and at least one encapsulation peptide that interacts or binds with to one or more carboxysome shell protein, each encapsulation peptide comprising at least 95% sequence identity to any of SEQ ID NO: 14, 15 or 16 fused to the at least one carbonic anhydrase domain.

2. The fusion protein of claim 1, wherein the Rubisco can synthesize 3-phosphoglycerate (3-PGA).

3. The fusion protein of claim 1, wherein the at least one carbonic anhydrase domain comprises at least 95% sequence identity to any of SEQ ID NO:17-21 or 71.

* * * * *

SEQUENCE LISTING

<160> NUMBER OF SEQ ID NOS: 77

<210> SEQ ID NO 1
<211> LENGTH: 539
<212> TYPE: PRT
<213> ORGANISM: Synechococcus elongatus

<400> SEQUENCE: 1

```
Met Pro Ser Pro Thr Val Pro Val Ala Thr Ala Gly Arg Leu Ala
1               5                   10                  15

Glu Pro Tyr Ile Asp Pro Ala Ala Gln Val His Ala Ile Ala Ser Ile
            20                  25                  30

Ile Gly Asp Val Arg Ile Ala Ala Gly Val Arg Val Ala Ala Gly Val
            35                  40                  45

Ser Ile Arg Ala Asp Glu Gly Ala Pro Phe Gln Val Gly Lys Glu Ser
    50                  55                  60

Ile Leu Gln Glu Gly Ala Val Ile His Gly Leu Glu Tyr Gly Arg Val
65                  70                  75                  80

Leu Gly Asp Asp Gln Ala Asp Tyr Ser Val Trp Ile Gly Gln Arg Val
                85                  90                  95

Ala Ile Thr His Lys Ala Leu Ile His Gly Pro Ala Tyr Leu Gly Asp
                100                 105                 110

Asp Cys Phe Val Gly Phe Arg Ser Thr Val Phe Asn Ala Arg Val Gly
            115                 120                 125

Ala Gly Ser Val Ile Met Met His Ala Leu Val Gln Asp Val Glu Ile
            130                 135                 140

Pro Pro Gly Arg Tyr Val Pro Ser Gly Ala Ile Ile Thr Thr Gln Gln
145                 150                 155                 160

Gln Ala Asp Arg Leu Pro Glu Val Arg Pro Glu Asp Arg Glu Phe Ala
                165                 170                 175

Arg His Ile Ile Gly Ser Pro Val Ile Val Arg Ser Thr Pro Ala
                180                 185                 190

Ala Thr Ala Asp Phe His Ser Thr Pro Thr Pro Ser Pro Leu Arg Pro
            195                 200                 205

Ser Ser Ser Glu Ala Thr Thr Val Ser Ala Tyr Asn Gly Gln Gly Arg
210                 215                 220

Leu Ser Ser Glu Val Ile Thr Gln Val Arg Ser Leu Leu Asn Gln Gly
225                 230                 235                 240

Tyr Arg Ile Gly Thr Glu His Ala Asp Lys Arg Arg Phe Arg Thr Ser
                245                 250                 255

Ser Trp Gln Pro Cys Ala Pro Ile Gln Ser Thr Asn Glu Arg Gln Val
                260                 265                 270

Leu Ser Glu Leu Glu Asn Cys Leu Ser Glu His Glu Gly Glu Tyr Val
                275                 280                 285

Arg Leu Leu Gly Ile Asp Thr Asn Thr Arg Ser Arg Val Phe Glu Ala
                290                 295                 300

Leu Ile Gln Arg Pro Asp Gly Ser Val Pro Glu Ser Leu Gly Ser Gln
305                 310                 315                 320

Pro Val Ala Val Ala Ser Gly Gly Gly Arg Gln Ser Ser Tyr Ala Ser
                325                 330                 335

Val Ser Gly Asn Leu Ser Ala Glu Val Val Asn Lys Val Arg Asn Leu
                340                 345                 350

Leu Ala Gln Gly Tyr Arg Ile Gly Thr Glu His Ala Asp Lys Arg Arg
                355                 360                 365

Phe Arg Thr Ser Ser Trp Gln Ser Cys Ala Pro Ile Gln Ser Ser Asn
            370                 375                 380

Glu Arg Gln Val Leu Ala Glu Leu Glu Asn Cys Leu Ser Glu His Glu
385                 390                 395                 400

Gly Glu Tyr Val Arg Leu Leu Gly Ile Asp Thr Ala Ser Arg Ser Arg
                405                 410                 415
```

-continued

Val Phe Glu Ala Leu Ile Gln Asp Pro Gln Gly Pro Val Gly Ser Ala
            420                 425                 430

Lys Ala Ala Ala Pro Val Ser Ser Ala Thr Pro Ser Ser His Ser
        435                 440                 445

Tyr Thr Ser Asn Gly Ser Ser Ser Asp Val Ala Gly Gln Val Arg
    450                 455                 460

Gly Leu Leu Ala Gln Gly Tyr Arg Ile Ser Ala Glu Val Ala Asp Lys
465                 470                 475                 480

Arg Arg Phe Gln Thr Ser Ser Trp Gln Ser Leu Pro Ala Leu Ser Gly
                485                 490                 495

Gln Ser Glu Ala Thr Val Leu Pro Ala Leu Glu Ser Ile Leu Gln Glu
                500                 505                 510

His Lys Gly Lys Tyr Val Arg Leu Ile Gly Ile Asp Pro Ala Ala Arg
            515                 520                 525

Arg Arg Val Ala Glu Leu Leu Ile Gln Lys Pro
        530                 535

<210> SEQ ID NO 2
<211> LENGTH: 539
<212> TYPE: PRT
<213> ORGANISM: Synechococcus elongatus

<400> SEQUENCE: 2

Met Pro Ser Pro Thr Thr Val Pro Val Ala Thr Ala Gly Arg Leu Ala
1               5                   10                  15

Glu Pro Tyr Ile Asp Pro Ala Ala Gln Val His Ala Ile Ala Ser Ile
                20                  25                  30

Ile Gly Asp Val Arg Ile Ala Ala Gly Val Arg Val Ala Ala Gly Val
            35                  40                  45

Ser Ile Arg Ala Asp Glu Gly Ala Pro Phe Gln Val Gly Lys Glu Ser
    50                  55                  60

Ile Leu Gln Glu Gly Ala Val Ile His Gly Leu Glu Tyr Gly Arg Val
65                  70                  75                  80

Leu Gly Asp Asp Gln Ala Asp Tyr Ser Val Trp Ile Gly Gln Arg Val
                85                  90                  95

Ala Ile Thr His Lys Ala Leu Ile His Gly Pro Ala Tyr Leu Gly Asp
                100                 105                 110

Asp Cys Phe Val Gly Phe Arg Ser Thr Val Phe Asn Ala Arg Val Gly
            115                 120                 125

Ala Gly Ser Val Ile Met Met His Ala Leu Val Gln Asp Val Glu Ile
130                 135                 140

Pro Pro Gly Arg Tyr Val Pro Ser Gly Ala Ile Ile Thr Thr Gln Gln
145                 150                 155                 160

Gln Ala Asp Arg Leu Pro Glu Val Arg Pro Glu Asp Arg Glu Phe Ala
                165                 170                 175

Arg His Ile Ile Gly Ser Pro Pro Val Ile Val Arg Ser Thr Pro Ala
            180                 185                 190

Ala Thr Ala Asp Phe His Ser Thr Pro Thr Pro Ser Pro Leu Arg Pro
        195                 200                 205

Ser Ser Ser Glu Ala Thr Thr Val Ser Ala Tyr Asn Gly Gln Gly Arg
    210                 215                 220

Leu Ser Ser Glu Val Ile Thr Gln Val Arg Ser Leu Leu Asn Gln Gly
225                 230                 235                 240

Tyr Arg Ile Gly Thr Glu His Ala Asp Lys Arg Arg Phe Arg Thr Ser
                245                 250                 255

-continued

```
Ser Trp Gln Pro Cys Ala Pro Ile Gln Ser Thr Asn Glu Arg Gln Val
            260                 265                 270

Leu Ser Glu Leu Glu Asn Cys Leu Ser Glu His Glu Gly Glu Tyr Val
        275                 280                 285

Arg Leu Leu Gly Ile Asp Thr Asn Thr Arg Ser Arg Val Phe Glu Ala
    290                 295                 300

Leu Ile Gln Arg Pro Asp Gly Ser Val Pro Glu Ser Leu Gly Ser Gln
305                 310                 315                 320

Pro Val Ala Val Ala Ser Gly Gly Arg Gln Ser Ser Tyr Ala Ser
                325                 330                 335

Val Ser Gly Asn Leu Ser Ala Glu Val Val Asn Lys Val Arg Asn Leu
            340                 345                 350

Leu Ala Gln Gly Tyr Arg Ile Gly Thr Glu His Ala Asp Lys Arg Arg
        355                 360                 365

Phe Arg Thr Ser Ser Trp Gln Ser Cys Ala Pro Ile Gln Ser Ser Asn
    370                 375                 380

Glu Arg Gln Val Leu Ala Glu Leu Glu Asn Cys Leu Ser Glu His Glu
385                 390                 395                 400

Gly Glu Tyr Val Arg Leu Leu Gly Ile Asp Thr Ala Ser Arg Ser Arg
                405                 410                 415

Val Phe Glu Ala Leu Ile Gln Asp Pro Gln Gly Pro Val Gly Ser Ala
            420                 425                 430

Lys Ala Ala Ala Pro Val Ser Ala Thr Pro Ser Ser His Ser
        435                 440                 445

Tyr Thr Ser Asn Gly Ser Ser Ser Asp Val Ala Gly Gln Val Arg
    450                 455                 460

Gly Leu Leu Ala Gln Gly Tyr Arg Ile Ser Ala Glu Val Ala Asp Lys
465                 470                 475                 480

Arg Arg Phe Gln Thr Ser Ser Trp Gln Ser Leu Pro Ala Leu Ser Gly
                485                 490                 495

Arg Ser Glu Ala Thr Val Leu Pro Ala Leu Glu Ser Ile Leu Gln Glu
            500                 505                 510

His Lys Gly Lys Tyr Val Arg Leu Ile Gly Ile Asp Pro Ala Ala Arg
        515                 520                 525

Arg Arg Val Ala Glu Leu Leu Ile Gln Lys Pro
    530                 535
```

<210> SEQ ID NO 3
<211> LENGTH: 566
<212> TYPE: PRT
<213> ORGANISM: Prochlorothrix hollandica

<400> SEQUENCE: 3

```
Met Ala Gly Tyr Ser Ser Ala Ala Pro Pro Thr Pro Trp Ser Arg Gly
1               5                   10                  15

Leu Ala Glu Pro Gln Ile Asp Gly Ser Ala Tyr Val His Ala Phe Ser
            20                  25                  30

Asn Val Ile Gly Asp Val Trp Ile Gly Glu Asn Val Leu Ile Ala Pro
        35                  40                  45

Gly Thr Ser Ile Arg Ala Asp Glu Gly Ala Pro Phe His Ile Gly Ser
    50                  55                  60

Ser Thr Asn Ile Gln Asp Gly Val Val Ile His Gly Leu Glu Gln Gly
65                  70                  75                  80

Arg Val Leu Gly Asp Asp Gln Lys Glu Tyr Ser Val Trp Val Gly Arg
                85                  90                  95
```

```
Asp Ser Ser Leu Thr His Lys Ala Leu Ile His Gly Pro Ala Tyr Val
            100                 105                 110
Gly Asp Glu Cys Phe Ile Gly Phe Arg Ser Thr Val Phe Asn Ala Arg
        115                 120                 125
Val Gly His Gly Cys Ile Val Met Met His Ala Leu Ile Gln Asp Val
    130                 135                 140
Glu Ile Pro Pro Gly Lys Tyr Val Pro Ser Gly Ala Ile Ile Thr Ser
145                 150                 155                 160
Gln Gln Gln Ala Asp Arg Leu Pro Asp Val Arg Gln Glu Asp Lys Asp
                165                 170                 175
Phe Ala His His Val Val Gly Ile Asn Glu Ala Leu Leu Ala Gly Tyr
            180                 185                 190
His Cys Ala Arg Ser Ser Ala Cys Ile Asn Pro Ile Arg Ala Gly Leu
        195                 200                 205
Ser Gln Thr Phe Gln Gly Ser Thr Pro Gly Thr His Gly Leu Glu Glu
    210                 215                 220
Ser Ile Asn Gly Thr Thr Asn Thr Met Asn Asn Gly Tyr Gly Leu Ser
225                 230                 235                 240
Pro Ala Leu Ile Ser Gln Val Arg Ser Leu Leu Ala Gln Gly Tyr Arg
                245                 250                 255
Ile Gly Thr Glu His Ala Thr Pro Arg Arg Phe Lys Thr Ser Ser Trp
            260                 265                 270
Glu Ser Cys Ala Pro Ile Glu Ser Lys Asn Gly Gln Val Leu Ser
        275                 280                 285
Ala Leu Ser Gly Cys Leu Gln Glu His Gln Gly Glu Tyr Val Arg Leu
    290                 295                 300
Leu Gly Ile Asp Val Gln Ala Arg Arg Arg Val Leu Glu Val Leu Ile
305                 310                 315                 320
Gln Arg Pro Asp Gly Lys Pro Thr Ser Leu Ser Thr Arg Gly Thr Val
                325                 330                 335
Ser Val Ala Ala Pro Ser Ala Ser Asn Gly His Arg Ser Ser Thr Ala
            340                 345                 350
Gly Thr Ser Asn Gly Gly Ser Leu Ala Asp Gln Val Arg Gly Leu
        355                 360                 365
Leu Gln Gln Gly Cys Arg Ile Thr Thr Glu His Ala Asp Lys Arg Arg
    370                 375                 380
Phe Lys Thr Ser Ser Trp Gln Val Gly Ala Val Ile Glu Ser Ser Asn
385                 390                 395                 400
Phe Asn Gln Val Met Ala Ala Leu Asp Ser Ala Met Gln Gln Tyr Ser
                405                 410                 415
Gly Glu Tyr Val Arg Leu Ile Ala Val Asp Pro Leu Ala Lys Arg Arg
            420                 425                 430
Val Ala Glu Val Leu Ile His Arg Pro Asp Gly Lys Pro Val Ala Thr
        435                 440                 445
Thr Ala Ala Ser Lys Gly Ser Thr Tyr Ser Ser Asn Gly Ala Ser Asn
    450                 455                 460
Gly Ala Ser Asn Gly Ala Ser Asn Gly Tyr Gly Gly Gly Ser Val
465                 470                 475                 480
Ser Gly Leu Ser Gly Glu Thr Ala Asn Gln Val Arg Gly Trp Leu Gly
                485                 490                 495
Gln Gly Tyr Arg Ile Ser Ala Glu Tyr Ala Asp Lys Arg Arg Phe Lys
            500                 505                 510
```

Thr Gly Ser Trp Gln Thr His Gly Thr Leu Glu Gly Arg Gly Asp Gln
            515                 520                 525

Val Leu Gly Ser Ile Ser Thr Val Leu Ser Thr His Ser Gly Asn Tyr
        530                 535                 540

Val Arg Leu Val Gly Val Asp Pro Gln Ala Lys Arg Arg Val Gly Gln
545                 550                 555                 560

Val Ile Ile Gln Arg Pro
                565

<210> SEQ ID NO 4
<211> LENGTH: 661
<212> TYPE: PRT
<213> ORGANISM: Hassallia byssoidea

<400> SEQUENCE: 4

Met Ala Val Arg Ser Thr Ala Ala Pro Pro Thr Pro Trp Ser Arg Asn
1               5                   10                  15

Leu Ala Glu Pro Asn Ile Asp Ala Thr Ala Tyr Ile His Pro Phe Ser
            20                  25                  30

Asn Val Ile Gly Asp Val Arg Ile Gly Ala Asn Val Ile Val Ala Pro
        35                  40                  45

Gly Thr Ser Ile Arg Ala Asp Glu Gly Thr Pro Phe Asn Ile Ser Glu
    50                  55                  60

Asn Thr Asn Leu Gln Asp Gly Val Val Ile His Gly Leu Glu Gln Gly
65                  70                  75                  80

Arg Val Ile Gly Asp Asp Asn Gln Tyr Ser Val Trp Ile Gly Lys
                85                  90                  95

Asn Ala Ser Ile Thr His Met Ala Leu Ile His Gly Pro Ala Tyr Val
            100                 105                 110

Gly Asp Asp Cys Phe Ile Gly Phe Arg Ser Thr Val Phe Asn Ala Arg
        115                 120                 125

Val Gly Asn Gly Cys Ile Val Met Met His Ala Leu Ile Gln Asp Val
    130                 135                 140

Glu Ile Pro Pro Gly Lys Tyr Val Pro Ser Gly Ala Ile Ile Thr Asn
145                 150                 155                 160

Gln Gln Gln Ala Asp Arg Leu Pro Asp Val Gln Val Gln Asp Arg Glu
            165                 170                 175

Phe Ser His His Val Val Gly Ile Asn Gln Ala Leu Arg Ser Gly Tyr
        180                 185                 190

Leu Cys Ala Ala Asp Asn Lys Cys Ile Lys Asn Ile Arg Asn Glu Met
    195                 200                 205

Thr Ser Ser Tyr Lys Thr Asn Gly Ser Asn Gly Tyr Ser Gly Asn Gly
    210                 215                 220

Ser Val Ser Ser Asn Leu Ser Ser Glu Thr Val Gln Gln Val Arg His
225                 230                 235                 240

Leu Leu Glu Gln Gly Tyr Gln Ile Gly Thr Glu His Val Asp Gln Arg
            245                 250                 255

Arg Phe Arg Thr Gly Ser Trp Ala Ser Cys Ser Pro Ile Ala Thr Asn
        260                 265                 270

Ser Thr Ser Glu Ala Ile Ala Ala Leu Glu Ser Cys Leu Ala Glu His
    275                 280                 285

Ser Gly Glu Phe Val Arg Leu Phe Gly Ile Asp Pro Lys Gly Lys Arg
    290                 295                 300

Arg Val Leu Glu Thr Ile Ile Gln Arg Pro Asp Gly Val Val Gln Asn
305                 310                 315                 320

```
Gly Thr Thr Pro Lys Leu Gly Val Lys Ser Ala Ser Tyr Ser Gly Gly
            325                 330                 335

Asn Ser Tyr Ser Gly Ser Ser Thr Leu Ser Gly Glu Ala Ile Glu Gln
            340                 345                 350

Val Arg Gln Leu Leu Ala Gly Gly Tyr Lys Ile Gly Met Glu His Val
            355                 360                 365

Asp Lys Arg Arg Phe Arg Thr Gly Ser Trp Gln Ser Cys Thr Pro Ile
370                 375                 380

Ala Ser Ser Asn Glu Lys Glu Val Ile Ser Ala Leu Glu Ala Cys Val
385                 390                 395                 400

Ala Ser His Thr Gly Glu Tyr Val Arg Leu Val Gly Ile Glu Pro Lys
            405                 410                 415

Ala Arg Lys Arg Val Leu Glu Ser Ile Ile Gln Arg Pro Asp Gly Asn
            420                 425                 430

Val Ala Glu Gly Ser Ser Asn Lys Phe Val Ala Ser Ser Ser Ser Glu
            435                 440                 445

Ser Arg Thr Ser Thr Asn Ala Ser Thr Arg Leu Ser Pro Glu Val Ile
450                 455                 460

Asp Gln Leu Arg Gln Leu Ile Asn Gln Gly Ser Lys Ile Ser Ala Glu
465                 470                 475                 480

His Val Asp Lys Arg Arg Phe Arg Thr Gly Ser Trp Ala Ser Cys Gly
            485                 490                 495

Gln Ile Gln Gly Asn Ser Glu Arg Glu Ala Ile Ala Ala Leu Glu Gly
            500                 505                 510

Tyr Leu Arg Glu Tyr Gln Gly Glu Tyr Val Arg Leu Ile Gly Ile Glu
            515                 520                 525

Pro Lys Ala Lys Lys Arg Val Leu Glu Ser Ile Ile Gln Arg Pro Asp
530                 535                 540

Asp Ser Val Ala Gln Ser Ser Arg Ser Asp Asn Gln Val Val Ala Ser
545                 550                 555                 560

Ser Ser Ser Ser Thr Ser Lys Thr Ser Asn Thr Ala Thr Ser Thr Arg
            565                 570                 575

Leu Ser Ser Glu Val Val Asp Gln Leu Arg Gln Leu Arg Asn Gln Gly
            580                 585                 590

Ser Lys Ile Ser Val Glu His Val Asp Gln Arg Arg Phe Arg Thr Gly
            595                 600                 605

Ser Trp Thr Ser Gly Gly Gln Ile Gln Gly Asn Ser Glu Arg Glu Ala
            610                 615                 620

Ile Ala Ala Leu Glu Gly Tyr Leu Arg Glu Tyr Glu Gly Glu Tyr Val
625                 630                 635                 640

Arg Leu Ile Gly Ile Asn Pro Lys Asp Lys Arg Val Leu Glu Thr
            645                 650                 655

Ile Ile Gln Arg Pro
            660

<210> SEQ ID NO 5
<211> LENGTH: 325
<212> TYPE: PRT
<213> ORGANISM: Synechococcus elongatus

<400> SEQUENCE: 5

Thr Val Ser Ala Tyr Asn Gly Gln Gly Arg Leu Ser Ser Glu Val Ile
1               5                   10                  15

Thr Gln Val Arg Ser Leu Leu Asn Gln Gly Tyr Arg Ile Gly Thr Glu
            20                  25                  30
```

```
His Ala Asp Lys Arg Arg Phe Arg Thr Ser Ser Trp Gln Pro Cys Ala
         35                  40                  45

Pro Ile Gln Ser Thr Asn Glu Arg Gln Val Leu Ser Glu Leu Glu Asn
 50                  55                  60

Cys Leu Ser Glu His Glu Gly Glu Tyr Val Arg Leu Leu Gly Ile Asp
 65                  70                  75                  80

Thr Asn Thr Arg Ser Arg Val Phe Glu Ala Leu Ile Gln Arg Pro Asp
                 85                  90                  95

Gly Ser Val Pro Glu Ser Leu Gly Ser Gln Pro Val Ala Val Ala Ser
                100                 105                 110

Gly Gly Gly Arg Gln Ser Ser Tyr Ala Ser Val Ser Gly Asn Leu Ser
            115                 120                 125

Ala Glu Val Val Asn Lys Val Arg Asn Leu Leu Ala Gln Gly Tyr Arg
        130                 135                 140

Ile Gly Thr Glu His Ala Asp Lys Arg Arg Phe Arg Thr Ser Ser Trp
145                 150                 155                 160

Gln Ser Cys Ala Pro Ile Gln Ser Ser Asn Glu Arg Gln Val Leu Ala
                165                 170                 175

Glu Leu Glu Asn Cys Leu Ser Glu His Glu Gly Glu Tyr Val Arg Leu
            180                 185                 190

Leu Gly Ile Asp Thr Ala Ser Arg Ser Arg Val Phe Glu Ala Leu Ile
        195                 200                 205

Gln Asp Pro Gln Gly Pro Val Gly Ser Ala Lys Ala Ala Ala Ala Pro
    210                 215                 220

Val Ser Ser Ala Thr Pro Ser Ser His Ser Tyr Thr Ser Asn Gly Ser
225                 230                 235                 240

Ser Ser Ser Asp Val Ala Gly Gln Val Arg Gly Leu Leu Ala Gln Gly
                245                 250                 255

Tyr Arg Ile Ser Ala Glu Val Ala Asp Lys Arg Arg Phe Gln Thr Ser
            260                 265                 270

Ser Trp Gln Ser Leu Pro Ala Leu Ser Gly Ser Glu Ala Thr Val
        275                 280                 285

Leu Pro Ala Leu Glu Ser Ile Leu Gln Glu His Lys Gly Lys Tyr Val
    290                 295                 300

Arg Leu Ile Gly Ile Asp Pro Ala Ala Arg Arg Val Ala Glu Leu
305                 310                 315                 320

Leu Ile Gln Lys Pro
                325

<210> SEQ ID NO 6
<211> LENGTH: 803
<212> TYPE: PRT
<213> ORGANISM: Acaryochloris marina

<400> SEQUENCE: 6

Met Val Ile His Ser Pro Ser Thr Ser Ala Ser Met Gln Ala Gly Asn
 1               5                  10                  15

Leu Pro Asp Pro Arg Val Ser Ser Ala Tyr Val His Ser Phe Ala
                 20                  25                  30

Lys Val Met Gly Asp Val His Val Gly Ala Asn Ala Leu Ile Ala Pro
             35                  40                  45

Gly Ser Thr Ile Gln Ala Asp Gln Gly Leu Pro Phe His Ile Gly Asp
         50                  55                  60

Asn Val Asn Ile Gln Asp Gly Ala Val Ile His Ala Ile Glu Pro Gly
 65                  70                  75                  80
```

-continued

Gln Val Arg Gly Lys Asp Gly Gln Asn Tyr Ala Val Trp Ile Gly Asn
                85                  90                  95

Asn Ser Cys Val Thr His Met Ala Leu Ile His Gly Pro Ala Phe Ile
            100                 105                 110

Gly Asp Asn Cys Phe Ile Gly Phe Arg Ser Thr Val Phe Asn Ala Lys
            115                 120                 125

Val Gly Asp Asn Cys Val Ile Met Met His Ala Leu Ile Gln Gly Val
130                 135                 140

Glu Ile Pro Pro Gly Lys Tyr Val Pro Ser Gly Ala Val Ile Thr Lys
145                 150                 155                 160

Gln Glu Gln Ala Asn Leu Leu Pro Asp Val Leu Glu Ser Asp Arg Lys
                165                 170                 175

Phe Thr Gln Gln Ile Ile His Val Asn Glu Ala Leu Lys Ser Glu Ile
                180                 185                 190

Ser Gly Ala Ser Thr Lys Thr Ser Ile Arg Pro Ala Arg Ala Asn Ile
            195                 200                 205

Gly His Ser Gln Ser His Arg Phe Thr Thr Asp Thr Lys Pro Met Asn
            210                 215                 220

His Thr Thr Leu Asp Ala Ala Ile Val Ser Gln Val Arg Ser Leu Leu
225                 230                 235                 240

Ala Gln Gly Tyr Arg Ile Gly Ser Glu His Ala Asp Lys Arg Arg Phe
                245                 250                 255

Gln Thr Ser Ser Trp Gln Ser Cys Pro Ser Ile Thr Ser Thr Asn Glu
                260                 265                 270

Ser Gln Val Leu Ala Gly Ile Glu Ser Cys Met Ser Glu His Gln Gly
            275                 280                 285

Glu Tyr Val Arg Leu Ile Gly Ile Asp Thr Gln Ala Arg Gln Arg Val
            290                 295                 300

Leu Glu Thr Ile Ile Gln Arg Pro Asp Gly Pro Val Lys Ser Ala Ser
305                 310                 315                 320

Ile Ser Ser Val Thr Lys Thr Ile Lys Asn Tyr Thr Thr Ser His Ile
                325                 330                 335

Ser Ser Ser Gly Asn Ile Asp Ala Glu Thr Ile Ala His Val Arg Ser
            340                 345                 350

Leu Leu Gly Gln Gly Tyr Arg Ile Gly Thr Glu His Ala Asp Ala Arg
            355                 360                 365

Arg Phe Gln Thr Ser Ser Trp Gln Ser Cys Ser Pro Ile Ala Ser Gln
            370                 375                 380

Gln Glu Ser Gln Val Val Ala Ala Leu Glu Ala Cys Ile Val Glu His
385                 390                 395                 400

Gln Gly Glu Tyr Val Arg Met Leu Gly Ile Asp Thr Gln Ala Lys Gln
                405                 410                 415

Arg Val Phe Glu Ala Ile Ile Gln Arg Pro Ser Asp Lys Pro Lys Ala
                420                 425                 430

Ala Pro Lys Ala Ser Arg Pro Ala Ser Thr Ser Ser Ser Ser Ser Ser
            435                 440                 445

Tyr Ala Ser Pro Ser Tyr Ala Ser Ser Pro Asn Ser Gly Thr Ser
            450                 455                 460

Thr Gly Leu Gly Ala Asp Ala Ile Ala Gln Val Arg Ser Leu Leu Ala
465                 470                 475                 480

Gln Gly Tyr Arg Val Gly Tyr Glu Tyr Ala Asp Lys Arg Arg Phe Gln
                485                 490                 495

```
Thr Ser Ser Trp Gln Ser Cys Thr Pro Ile Asn Ser Gln Gln Glu Ser
            500                 505                 510

Gln Val Ile Ala Ala Leu Glu Ser Cys Ile Ala Glu His Pro Gly Asn
        515                 520                 525

Tyr Val Arg Leu Ile Gly Ile Asp Pro Lys Ala Lys Arg Arg Val Leu
        530                 535                 540

Glu Val Ile Ile Gln Arg Pro Asp Ser Asn Ser Lys Ala Ser Pro Ser
545                 550                 555                 560

Ala Pro Lys Ala Arg Pro Ala Ser Ser Ser Ser Tyr Ser Ser Lys
                565                 570                 575

Val Glu Ser Asn Ser Ser Ser Tyr Arg Pro Ala Pro Ser Ala Gly Leu
        580                 585                 590

Asp Gly Thr Val Val Asn Gln Ile Arg Ser Leu Leu Ala Gln Gly Tyr
        595                 600                 605

Arg Ile Gly Thr Glu Tyr Ala Asp Lys Arg Phe Gln Thr Ser Ser
        610                 615                 620

Trp Gln Ser Cys Thr Pro Ile Ala Ser Gln Gln Glu Ser Gln Val Ile
625                 630                 635                 640

Ala Gly Val Glu Ala Cys Met Ala Glu His Pro Asn Asp Tyr Val Arg
                645                 650                 655

Leu Ile Gly Ile Asp Lys Arg Ala Lys Arg Met Ser Glu Thr Ile
                660                 665                 670

Ile Gln Arg Pro Gly Gly Ser Thr Ala Thr Ser Ser Ser Val Lys Thr
        675                 680                 685

Ser Ser Ser Arg Ser Tyr Gln Ala Pro Ala Ala Lys Ser Ser Arg Gly
        690                 695                 700

Arg Gly Phe Ser Pro Arg Asn Gly Gly Ser Leu Asp Ala Asp Thr Val
705                 710                 715                 720

Ala Gln Val Arg Ser Leu Leu Ala Gln Gly Tyr Arg Ile Ser Thr Glu
                725                 730                 735

Tyr Ala Asp Lys Arg Arg Phe Gln Thr Ser Ser Trp Gln Ser Cys Pro
                740                 745                 750

Pro Ile Lys Thr Gln Gln Glu Ser Gln Val Ile Ala Ala Leu Glu Ser
        755                 760                 765

Cys Met Ala Asp His Gln Lys Glu Tyr Val Arg Leu Ile Gly Ile Asp
        770                 775                 780

Thr Asn Ala Lys Arg Arg Val Leu Glu Ser Val Ile Gln Lys Pro Val
785                 790                 795                 800

Ala Ala His

<210> SEQ ID NO 7
<211> LENGTH: 583
<212> TYPE: PRT
<213> ORGANISM: Acaryochloris marina

<400> SEQUENCE: 7

Lys Pro Met Asn His Thr Thr Leu Asp Ala Ala Ile Val Ser Gln Val
1               5                   10                  15

Arg Ser Leu Leu Ala Gln Gly Tyr Arg Ile Gly Ser Glu His Ala Asp
                20                  25                  30

Lys Arg Arg Phe Gln Thr Ser Ser Trp Gln Ser Cys Pro Ser Ile Thr
            35                  40                  45

Ser Thr Asn Glu Ser Gln Val Leu Ala Gly Ile Glu Ser Cys Met Ser
        50                  55                  60
```

-continued

```
Glu His Gln Gly Glu Tyr Val Arg Leu Ile Gly Ile Asp Thr Gln Ala
 65                  70                  75                  80

Arg Gln Arg Val Leu Glu Thr Ile Ile Gln Arg Pro Asp Gly Pro Val
                 85                  90                  95

Lys Ser Ala Ser Ile Ser Ser Val Thr Lys Thr Ile Lys Asn Tyr Thr
                100                 105                 110

Thr Ser His Ile Ser Ser Ser Gly Asn Ile Asp Ala Glu Thr Ile Ala
                115                 120                 125

His Val Arg Ser Leu Leu Gly Gln Gly Tyr Arg Ile Gly Thr Glu His
            130                 135                 140

Ala Asp Ala Arg Arg Phe Gln Thr Ser Ser Trp Gln Ser Cys Ser Pro
145                 150                 155                 160

Ile Ala Ser Gln Gln Glu Ser Gln Val Val Ala Ala Leu Glu Ala Cys
                165                 170                 175

Ile Val Glu His Gln Gly Glu Tyr Val Arg Met Leu Gly Ile Asp Thr
                180                 185                 190

Gln Ala Lys Gln Arg Val Phe Glu Ala Ile Ile Gln Arg Pro Ser Asp
            195                 200                 205

Lys Pro Lys Ala Ala Pro Lys Ala Ser Arg Pro Ala Ser Thr Ser Ser
210                 215                 220

Ser Ser Ser Ser Tyr Ala Ser Pro Ser Tyr Ala Ser Ser Ser Pro Asn
225                 230                 235                 240

Ser Gly Thr Ser Thr Gly Leu Gly Ala Asp Ala Ile Ala Gln Val Arg
                245                 250                 255

Ser Leu Leu Ala Gln Gly Tyr Arg Val Gly Tyr Glu Tyr Ala Asp Lys
            260                 265                 270

Arg Arg Phe Gln Thr Ser Ser Trp Gln Ser Cys Thr Pro Ile Asn Ser
            275                 280                 285

Gln Gln Glu Ser Gln Val Ile Ala Ala Leu Glu Ser Cys Ile Ala Glu
            290                 295                 300

His Pro Gly Asn Tyr Val Arg Leu Ile Gly Ile Asp Pro Lys Ala Lys
305                 310                 315                 320

Arg Arg Val Leu Glu Val Ile Ile Gln Arg Pro Asp Ser Asn Ser Lys
                325                 330                 335

Ala Ser Pro Ser Ala Pro Lys Ala Arg Pro Ala Ser Ser Ser Ser Ser
                340                 345                 350

Tyr Ser Ser Lys Val Glu Ser Asn Ser Ser Tyr Arg Pro Ala Pro
                355                 360                 365

Ser Ala Gly Leu Asp Gly Thr Val Val Asn Gln Ile Arg Ser Leu Leu
370                 375                 380

Ala Gln Gly Tyr Arg Ile Gly Thr Glu Tyr Ala Asp Lys Arg Arg Phe
385                 390                 395                 400

Gln Thr Ser Ser Trp Gln Ser Cys Thr Pro Ile Ala Ser Gln Gln Glu
                405                 410                 415

Ser Gln Val Ile Ala Gly Val Glu Ala Cys Met Ala Glu His Pro Asn
                420                 425                 430

Asp Tyr Val Arg Leu Ile Gly Ile Asp Lys Arg Ala Lys Arg Arg Met
            435                 440                 445

Ser Glu Thr Ile Ile Gln Arg Pro Gly Gly Ser Thr Ala Thr Ser Ser
            450                 455                 460

Ser Val Lys Thr Ser Ser Ser Arg Ser Tyr Gln Ala Pro Ala Ala Lys
465                 470                 475                 480
```

Ser Ser Arg Gly Arg Gly Phe Ser Pro Arg Asn Gly Ser Leu Asp
              485             490             495

Ala Asp Thr Val Ala Gln Val Arg Ser Leu Leu Ala Gln Gly Tyr Arg
          500             505             510

Ile Ser Thr Glu Tyr Ala Asp Lys Arg Phe Gln Thr Ser Ser Trp
      515             520             525

Gln Ser Cys Pro Pro Ile Lys Thr Gln Gln Glu Ser Gln Val Ile Ala
      530             535             540

Ala Leu Glu Ser Cys Met Ala Asp His Gln Lys Glu Tyr Val Arg Leu
545             550             555             560

Ile Gly Ile Asp Thr Asn Ala Lys Arg Arg Val Leu Glu Ser Val Ile
              565             570             575

Gln Lys Pro Val Ala Ala His
              580

<210> SEQ ID NO 8
<211> LENGTH: 652
<212> TYPE: PRT
<213> ORGANISM: Thermosynechococcus elongatus

<400> SEQUENCE: 8

Met Ala Val Gln Ser Tyr Ala Ala Pro Pro Thr Pro Trp Ser Arg Asp
1               5                   10                  15

Leu Ala Glu Pro Glu Ile Ala Pro Thr Ala Tyr Val His Ser Phe Ser
                20                  25                  30

Asn Leu Ile Gly Asp Val Arg Ile Lys Asp Tyr Val His Ile Ala Pro
            35                  40                  45

Gly Thr Ser Ile Arg Ala Asp Glu Gly Thr Pro Phe His Ile Gly Ser
        50                  55                  60

Arg Thr Asn Ile Gln Asp Gly Val Val Ile His Gly Leu Gln Gln Gly
65                  70                  75                  80

Arg Val Ile Gly Asp Asp Gly Gln Glu Tyr Ser Val Trp Ile Gly Asp
                85                  90                  95

Asn Val Ser Ile Thr His Met Ala Leu Ile His Gly Pro Ala Tyr Ile
            100                 105                 110

Gly Asp Gly Cys Phe Ile Gly Phe Arg Ser Thr Val Phe Asn Ala Arg
        115                 120                 125

Val Gly Ala Gly Cys Val Val Met Met His Val Leu Ile Gln Asp Val
    130                 135                 140

Glu Ile Pro Pro Gly Lys Tyr Val Pro Ser Gly Met Val Ile Thr Thr
145                 150                 155                 160

Gln Gln Gln Ala Asp Arg Leu Pro Asn Val Glu Glu Ser Asp Ile His
                165                 170                 175

Phe Ala Gln His Val Val Gly Ile Asn Glu Ala Leu Leu Ser Gly Tyr
            180                 185                 190

Gln Cys Ala Glu Asn Ile Ala Cys Ile Ala Pro Ile Arg Asn Glu Leu
        195                 200                 205

Gln Arg Gln Glu Asp Pro Pro Thr Leu His Val Glu Met Leu Thr Gly
    210                 215                 220

Glu Lys Asn Thr Met Thr Thr Asp Tyr Gly Thr His Val Arg Gln Leu
225                 230                 235                 240

Leu Gln Gln Gly Tyr Gln Ile Ser Leu Glu Tyr Ala Asp Ala Arg Arg
                245                 250                 255

Tyr Arg Thr Ser Ser Trp Gln Ser Gly Pro Thr Leu Thr Gly Gln Gln
            260                 265                 270

Glu Ser Gln Val Met Ala Ala Ile Ala Gln Leu Leu Lys Glu His Glu
                275                 280                 285

Gly Glu Tyr Val Arg Leu Ile Gly Val Asp Pro Lys Ala Lys Arg Arg
        290                 295                 300

Val Phe Glu Glu Ile Ile Gln Arg Pro Gly Gln Ala Ala Val Ala Ser
305                 310                 315                 320

Ser Ser Ser Ser Arg Pro Ser Ala Thr Val Asn Ala Ser Pro Val Gly
                325                 330                 335

Ser Leu Asp Ala Ala Val Val Ala Gln Val Arg Gln Leu Leu Gln Gln
                340                 345                 350

Gly Tyr Gln Ile Gly Thr Glu His Ala Asp Ala Arg Arg Tyr Arg Thr
        355                 360                 365

Ser Ser Trp Thr Ser Cys Ala Pro Ile Gln Ser Lys Gln Glu Pro Glu
        370                 375                 380

Val Leu Ala Ala Leu Glu Ala Cys Leu Gln Glu His Ala Gly Glu Tyr
385                 390                 395                 400

Val Arg Leu Ile Gly Ile Asp Gln Lys Gln Lys Arg Arg Val Leu Glu
                405                 410                 415

Gln Ile Ile Gln Arg Pro Gln Gly Pro Val Ala Ile Ala Pro Lys Thr
        420                 425                 430

Pro Thr Pro Val Ala Thr Ser His Ala Ser Val Ser Ser Gly Gly Asn
        435                 440                 445

Asp Thr Leu Leu Ser Ala Asp Leu Val Asn Gln Ile Gln Asp Leu Leu
        450                 455                 460

Arg Gln Gly Cys Gln Val Ile Thr Glu Tyr Ala Asp Gln Arg Arg Phe
465                 470                 475                 480

Arg Thr Ser Ser Trp Gln Ser Gly Ile Lys Ile Thr Ser Ala Gln Gln
                485                 490                 495

Ile Asn Asp Leu Arg Ser Phe Leu Ala Glu His Gln Arg Asp Tyr Ile
                500                 505                 510

Arg Leu Val Gly Val Asn Pro Gln Ala Lys Gln Arg Val Leu Glu Thr
        515                 520                 525

Ile Ile His Arg Pro Asn Gly Lys Ala Ala Ser Asn Gly Asn Ser Thr
        530                 535                 540

Arg Gly Gln Gly Phe Thr Pro Arg Pro Thr Ala Ser Ser Gln Gly Ser
545                 550                 555                 560

Pro Ser Thr His Ser Leu Ser Gln Glu Val Ile Glu Gln Val Arg Gln
                565                 570                 575

Leu Leu Gln Gln Gly Tyr Thr Leu Gly Leu Glu His Val Asp Ala Arg
        580                 585                 590

Arg Tyr Arg Thr Asn Ser Trp Gln Ser Gly Pro Arg Ile Glu Ala Lys
        595                 600                 605

Asn Leu Asn Glu Ala Leu Ala Ala Ile Gln Ala Cys Leu Gln Glu Tyr
        610                 615                 620

Ser Gly Glu Tyr Val Arg Leu Ile Gly Ile Asn Pro Ala Gly Lys Gln
625                 630                 635                 640

Arg Val Ala Glu Ile Leu Leu Gln Gln Ala Ala Lys
                645                 650

<210> SEQ ID NO 9
<211> LENGTH: 418
<212> TYPE: PRT
<213> ORGANISM: Thermosynechococcus elongatus

```
<400> SEQUENCE: 9

Thr His Val Arg Gln Leu Leu Gln Gln Gly Tyr Gln Ile Ser Leu Glu
1               5                   10                  15

Tyr Ala Asp Ala Arg Arg Tyr Arg Thr Ser Ser Trp Gln Ser Gly Pro
            20                  25                  30

Thr Leu Thr Gly Gln Gln Glu Ser Gln Val Met Ala Ala Ile Ala Gln
        35                  40                  45

Leu Leu Lys Glu His Glu Gly Glu Tyr Val Arg Leu Ile Gly Val Asp
    50                  55                  60

Pro Lys Ala Lys Arg Arg Val Phe Glu Glu Ile Ile Gln Arg Pro Gly
65                  70                  75                  80

Gln Ala Ala Val Ala Ser Ser Ser Ser Arg Pro Ser Ala Thr Val
                85                  90                  95

Asn Ala Ser Pro Val Gly Ser Leu Asp Ala Ala Val Ala Gln Val
            100                 105                 110

Arg Gln Leu Leu Gln Gln Gly Tyr Gln Ile Gly Thr Glu His Ala Asp
            115                 120                 125

Ala Arg Arg Tyr Arg Thr Ser Ser Trp Thr Ser Cys Ala Pro Ile Gln
130                 135                 140

Ser Lys Gln Glu Pro Glu Val Leu Ala Ala Leu Glu Ala Cys Leu Gln
145                 150                 155                 160

Glu His Ala Gly Glu Tyr Val Arg Leu Ile Gly Ile Asp Gln Lys Gln
                165                 170                 175

Lys Arg Arg Val Leu Glu Gln Ile Ile Gln Arg Pro Gln Gly Pro Val
            180                 185                 190

Ala Ile Ala Pro Lys Thr Pro Thr Pro Val Ala Thr Ser His Ala Ser
            195                 200                 205

Val Ser Ser Gly Gly Asn Asp Thr Leu Leu Ser Ala Asp Leu Val Asn
    210                 215                 220

Gln Ile Gln Asp Leu Leu Arg Gln Gly Cys Gln Val Ile Thr Glu Tyr
225                 230                 235                 240

Ala Asp Gln Arg Arg Phe Arg Thr Ser Ser Trp Gln Ser Gly Ile Lys
                245                 250                 255

Ile Thr Ser Ala Gln Gln Ile Asn Asp Leu Arg Ser Phe Leu Ala Glu
            260                 265                 270

His Gln Arg Asp Tyr Ile Arg Leu Val Gly Val Asn Pro Gln Ala Lys
            275                 280                 285

Gln Arg Val Leu Glu Thr Ile Ile His Arg Pro Asn Gly Lys Ala Ala
    290                 295                 300

Ser Asn Gly Asn Ser Thr Arg Gly Gln Gly Phe Thr Pro Arg Pro Thr
305                 310                 315                 320

Ala Ser Ser Gln Gly Ser Pro Ser Thr His Ser Leu Ser Gln Glu Val
                325                 330                 335

Ile Glu Gln Val Arg Gln Leu Leu Gln Gln Gly Tyr Thr Leu Gly Leu
            340                 345                 350

Glu His Val Asp Ala Arg Arg Tyr Arg Thr Asn Ser Trp Gln Ser Gly
            355                 360                 365

Pro Arg Ile Glu Ala Lys Asn Leu Asn Glu Ala Leu Ala Ala Ile Gln
    370                 375                 380

Ala Cys Leu Gln Glu Tyr Ser Gly Glu Tyr Val Arg Leu Ile Gly Ile
385                 390                 395                 400
```

Asn Pro Ala Gly Lys Gln Arg Val Ala Glu Ile Leu Leu Gln Gln Ala
            405                 410                 415

Ala Lys

<210> SEQ ID NO 10
<211> LENGTH: 552
<212> TYPE: PRT
<213> ORGANISM: Trichormus azollae

<400> SEQUENCE: 10

Met Val Val Arg Ser Thr Ala Ala Pro Pro Thr Pro Trp Ser Arg Ser
1               5                   10                  15

Leu Ala Glu Pro Asp Ile His Gln Thr Ala Phe Val His Ser Ser Cys
            20                  25                  30

Asn Leu Ile Gly Asp Val His Leu Gly Gln Asn Val Ile Ile Ala Pro
        35                  40                  45

Gly Thr Ser Ile Arg Ala Asp Glu Gly Thr Pro Phe Phe Ile Gly Glu
    50                  55                  60

Asn Thr Asn Ile Gln Asp Gly Val Val Ile His Gly Leu Glu Gln Gly
65                  70                  75                  80

Arg Val Ile Gly Asp Asp Gly Lys Asn Tyr Ser Val Trp Val Gly Lys
                85                  90                  95

Asp Ala Ser Ile Thr His Met Ala Leu Ile His Gly Pro Ala Tyr Val
            100                 105                 110

Gly Glu Ser Cys Phe Ile Gly Phe Arg Ser Thr Val Phe Asn Ala Arg
        115                 120                 125

Val Gly Ala Gly Cys Ile Val Met Met His Ala Leu Ile Gln Asp Val
    130                 135                 140

Glu Ile Pro Pro Gly Lys Tyr Val Ala Ser Gly Ser Ile Ile Thr Met
145                 150                 155                 160

Gln Gln Gln Ala Asp Arg Leu Pro Asp Val Gln Ala Gln Asp Gln Gln
                165                 170                 175

Phe Ala His His Val Val Gly Ile Asn Gln Ala Leu Arg Ala Gly Tyr
            180                 185                 190

Arg Cys Val Glu Asp Ile Lys Cys Ile Ala Pro Ile Arg Asp Glu Leu
        195                 200                 205

Asn Leu Ser Gly Asp Arg Ser Tyr Thr Ser Ile Ile Val Asp Glu Leu
    210                 215                 220

Glu Arg Ser Ser Glu Val Ala Ser Lys Leu Gly Ala Glu Ile Val Asp
225                 230                 235                 240

Gln Val Arg Tyr Leu Leu Asn Gln Gly Tyr Lys Ile Gly Thr Glu His
                245                 250                 255

Val Asp Gln Arg Arg Phe Arg Thr Gly Ser Trp Gln Ser Cys Gln Pro
            260                 265                 270

Ile Glu Thr Arg Ser Leu Gly Glu Ala Ile Thr Ala Leu Glu Ser Cys
        275                 280                 285

Leu Ile Asp His Ser Gly Glu Tyr Val Arg Leu Phe Gly Ile Asp Asn
    290                 295                 300

Gly Arg Lys Arg Val Leu Glu Thr Ile Ile Gln Arg Pro Asp Gly Val
305                 310                 315                 320

Val Ala Thr Ser Thr Ser Ser Phe Lys Thr Pro Ala Ala Ser Tyr Ser
                325                 330                 335

Ser Tyr Asn Gly Asn Gly Asn Ser Asn Gly Ala Val Ala Ser Gly Ser
            340                 345                 350

```
Leu Ser Ala Glu Thr Val Asn Gln Ile Arg Gln Leu Leu Ala Asn Gly
            355                 360                 365

Tyr Lys Ile Gly Thr Glu His Val Asp Gln Arg Phe Arg Thr Gly
    370                 375                 380

Ser Trp Gln Ser Cys Asn Pro Ile Glu Ala Thr Ser Ala Asn Asp Val
385                 390                 395                 400

Val Ala Ala Leu Glu Glu Cys Met Thr Ser His Gln Gly Glu Tyr Val
                405                 410                 415

Arg Leu Ile Gly Ile Asp Ser Lys Ala Lys Arg Val Leu Glu Ala
            420                 425                 430

Ile Ile Gln Arg Pro Asn Gly Gln Val Val Ser Ser Gly Ser Ala Lys
            435                 440                 445

Thr Ser Gly Thr Leu Tyr Ser Gly Ala Thr Ala Ser Ala Thr Ala Thr
            450                 455                 460

Ser Thr Arg Leu Ser Thr Glu Val Val Asp Gln Leu Lys Gln Leu Leu
465                 470                 475                 480

Thr Gly Gly Phe Lys Ile Ser Val Glu His Val Asp Gln Arg Arg Phe
                485                 490                 495

Arg Thr Gly Ser Trp Val Ser Cys Gly Gln Ile Gln Ala Thr Ser Glu
            500                 505                 510

Arg Asp Val Leu Ala Ala Leu Glu Ala Val Ile Ser Glu Tyr Ala Gly
            515                 520                 525

Glu Tyr Val Arg Leu Ile Gly Ile Asp Pro Val Ala Lys Arg Arg Val
            530                 535                 540

Leu Glu Ala Ile Ile Gln Arg Pro
545                 550

<210> SEQ ID NO 11
<211> LENGTH: 323
<212> TYPE: PRT
<213> ORGANISM: Trichormus azollae

<400> SEQUENCE: 11

Val Ala Ser Lys Leu Gly Ala Glu Ile Val Asp Gln Val Arg Tyr Leu
1               5                   10                  15

Leu Asn Gln Gly Tyr Lys Ile Gly Thr Glu His Val Asp Gln Arg Arg
            20                  25                  30

Phe Arg Thr Gly Ser Trp Gln Ser Cys Gln Pro Ile Glu Thr Arg Ser
        35                  40                  45

Leu Gly Glu Ala Ile Thr Ala Leu Glu Ser Cys Leu Ile Asp His Ser
    50                  55                  60

Gly Glu Tyr Val Arg Leu Phe Gly Ile Asp Asn Gly Arg Lys Arg Val
65                  70                  75                  80

Leu Glu Thr Ile Ile Gln Arg Pro Asp Gly Val Val Ala Thr Ser Thr
                85                  90                  95

Ser Ser Phe Lys Thr Pro Ala Ala Ser Tyr Ser Ser Tyr Asn Gly Asn
            100                 105                 110

Gly Asn Ser Asn Gly Ala Val Ala Ser Gly Ser Leu Ser Ala Glu Thr
        115                 120                 125

Val Asn Gln Ile Arg Gln Leu Leu Ala Asn Gly Tyr Lys Ile Gly Thr
    130                 135                 140

Glu His Val Asp Gln Arg Arg Phe Arg Thr Gly Ser Trp Gln Ser Cys
145                 150                 155                 160
```

Asn Pro Ile Glu Ala Thr Ser Ala Asn Asp Val Val Ala Ala Leu Glu
            165                 170                 175

Glu Cys Met Thr Ser His Gln Gly Glu Tyr Val Arg Leu Ile Gly Ile
        180                 185                 190

Asp Ser Lys Ala Lys Arg Arg Val Leu Glu Ala Ile Ile Gln Arg Pro
            195                 200                 205

Asn Gly Gln Val Val Ser Ser Gly Ser Ala Lys Thr Ser Gly Thr Leu
        210                 215                 220

Tyr Ser Gly Ala Thr Ala Ser Ala Thr Ala Thr Ser Thr Arg Leu Ser
225                 230                 235                 240

Thr Glu Val Val Asp Gln Leu Lys Gln Leu Leu Thr Gly Gly Phe Lys
                245                 250                 255

Ile Ser Val Glu His Val Asp Gln Arg Arg Phe Arg Thr Gly Ser Trp
            260                 265                 270

Val Ser Cys Gly Gln Ile Gln Ala Thr Ser Glu Arg Asp Val Leu Ala
        275                 280                 285

Ala Leu Glu Ala Val Ile Ser Gly Tyr Ala Gly Glu Tyr Val Arg Leu
    290                 295                 300

Ile Gly Ile Asp Pro Val Ala Lys Arg Arg Val Leu Glu Ala Ile Ile
305                 310                 315                 320

Gln Arg Pro

<210> SEQ ID NO 12
<211> LENGTH: 161
<212> TYPE: PRT
<213> ORGANISM: Synechococcus elongatus

<400> SEQUENCE: 12

Met His Leu Pro Pro Leu Glu Pro Pro Ile Ser Asp Arg Tyr Phe Ala
1               5                   10                  15

Ser Gly Glu Val Thr Ile Ala Ala Asp Val Val Ile Ala Pro Gly Val
            20                  25                  30

Leu Leu Ile Ala Glu Ala Asp Ser Arg Ile Glu Ile Ala Ser Gly Val
        35                  40                  45

Cys Ile Gly Leu Gly Ser Val Ile His Ala Arg Gly Gly Ala Ile Ile
    50                  55                  60

Ile Gln Ala Gly Ala Leu Leu Ala Ala Gly Val Leu Ile Val Gly Gln
65                  70                  75                  80

Ser Ile Val Gly Arg Gln Ala Cys Leu Gly Ala Ser Thr Thr Leu Val
                85                  90                  95

Asn Thr Ser Ile Glu Ala Gly Gly Val Thr Ala Pro Gly Ser Leu Leu
            100                 105                 110

Ser Ala Glu Thr Pro Pro Thr Thr Ala Thr Val Ser Ser Ser Glu Pro
        115                 120                 125

Ala Gly Arg Ser Pro Gln Ser Ser Ala Ile Ala His Pro Thr Lys Val
    130                 135                 140

Tyr Gly Lys Glu Gln Phe Leu Arg Met Arg Gln Ser Met Phe Pro Asp
145                 150                 155                 160

Arg

<210> SEQ ID NO 13
<211> LENGTH: 18
<212> TYPE: PRT
<213> ORGANISM: Synechococcus elongatus

```
<400> SEQUENCE: 13

Val Tyr Gly Lys Glu Gln Phe Leu Arg Met Arg Gln Ser Met Phe Pro
1               5                   10                  15

Asp Arg

<210> SEQ ID NO 14
<211> LENGTH: 17
<212> TYPE: PRT
<213> ORGANISM: Prochlorothrix hollandica

<400> SEQUENCE: 14

Val Tyr Gly Arg Asp Tyr Phe Leu Gln Met Arg Phe Ser Leu Phe Pro
1               5                   10                  15

Asp

<210> SEQ ID NO 15
<211> LENGTH: 44
<212> TYPE: PRT
<213> ORGANISM: Halothece sp. PCC 7418

<400> SEQUENCE: 15

Ile Tyr Gly Gln Thr His Ile Glu Arg Leu Met Val Thr Leu Phe Pro
1               5                   10                  15

His Lys Glu Lys Phe Lys Lys Lys Thr Asn Asp Trp Phe Leu Val Leu
            20                  25                  30

Gly Ser Leu Leu Phe Asp Asp Phe Pro Asn Asn Glu
        35                  40

<210> SEQ ID NO 16
<211> LENGTH: 18
<212> TYPE: PRT
<213> ORGANISM: Moorea producens

<400> SEQUENCE: 16

Glu Gln Phe Phe Arg Arg Met Arg Gln Ser Leu Asn Arg Ala Phe Ser
1               5                   10                  15

Glu Arg

<210> SEQ ID NO 17
<211> LENGTH: 272
<212> TYPE: PRT
<213> ORGANISM: Synechococcus elongatus

<400> SEQUENCE: 17

Met Arg Lys Leu Ile Glu Gly Leu Arg His Phe Arg Thr Ser Tyr Tyr
1               5                   10                  15

Pro Ser His Arg Asp Leu Phe Glu Gln Phe Ala Lys Gly Gln His Pro
            20                  25                  30

Arg Val Leu Phe Ile Thr Cys Ser Asp Ser Arg Ile Asp Pro Asn Leu
        35                  40                  45

Ile Thr Gln Ser Gly Met Gly Glu Leu Phe Val Ile Arg Asn Ala Gly
    50                  55                  60

Asn Leu Ile Pro Pro Phe Gly Ala Ala Asn Gly Gly Glu Gly Ala Ser
65                  70                  75                  80

Ile Glu Tyr Ala Ile Ala Ala Leu Asn Ile Glu His Val Val Val Cys
                85                  90                  95

Gly His Ser His Cys Gly Ala Met Lys Gly Leu Leu Lys Leu Asn Gln
            100                 105                 110
```

Leu Gln Glu Asp Met Pro Leu Val Tyr Asp Trp Leu Gln His Ala Gln
            115                 120                 125

Ala Thr Arg Arg Leu Val Leu Asp Asn Tyr Ser Gly Tyr Glu Thr Asp
        130                 135                 140

Asp Leu Val Glu Ile Leu Val Ala Glu Asn Val Leu Thr Gln Ile Glu
145                 150                 155                 160

Asn Leu Lys Thr Tyr Pro Ile Val Arg Ser Arg Leu Phe Gln Gly Lys
                165                 170                 175

Leu Gln Ile Phe Gly Trp Ile Tyr Glu Val Glu Ser Gly Glu Val Leu
            180                 185                 190

Gln Ile Ser Arg Thr Ser Ser Asp Asp Thr Gly Ile Asp Glu Cys Pro
        195                 200                 205

Val Arg Leu Pro Gly Ser Gln Glu Lys Ala Ile Leu Gly Arg Cys Val
    210                 215                 220

Val Pro Leu Thr Glu Glu Val Ala Val Ala Pro Glu Pro Glu Pro
225                 230                 235                 240

Val Ile Ala Ala Val Ala Ala Pro Pro Ala Asn Tyr Ser Ser Arg Gly
                245                 250                 255

Trp Leu Ala Pro Glu Gln Gln Gln Arg Ile Tyr Arg Gly Asn Ala Ser
            260                 265                 270

<210> SEQ ID NO 18
<211> LENGTH: 272
<212> TYPE: PRT
<213> ORGANISM: Synechococcus elongatus

<400> SEQUENCE: 18

Met Arg Lys Leu Ile Glu Gly Leu Arg His Phe Arg Thr Ser Tyr Tyr
1               5                   10                  15

Pro Ser His Arg Asp Leu Phe Glu Gln Phe Ala Lys Gly Gln His Pro
            20                  25                  30

Arg Val Leu Phe Ile Thr Cys Ser Asp Ser Arg Ile Asp Pro Asn Leu
        35                  40                  45

Ile Thr Gln Ser Gly Met Gly Glu Leu Phe Val Ile Arg Asn Ala Gly
    50                  55                  60

Asn Leu Ile Pro Pro Phe Gly Ala Ala Asn Gly Gly Glu Gly Ala Ser
65                  70                  75                  80

Ile Glu Tyr Ala Ile Ala Ala Leu Asn Ile Glu His Val Val Val Cys
                85                  90                  95

Gly His Ser His Cys Gly Ala Met Lys Gly Leu Leu Lys Leu Asn Gln
            100                 105                 110

Leu Gln Glu Asp Met Pro Leu Val Tyr Asp Trp Leu Gln His Ala Gln
            115                 120                 125

Ala Thr Arg Arg Leu Val Leu Asp Asn Tyr Ser Gly Tyr Glu Thr Asp
        130                 135                 140

Asp Leu Val Glu Phe Leu Val Ala Glu Asn Val Leu Thr Gln Ile Glu
145                 150                 155                 160

Asn Leu Lys Thr Tyr Pro Ile Val Arg Ser Arg Leu Phe Gln Gly Lys
                165                 170                 175

Leu Gln Ile Phe Gly Trp Ile Tyr Glu Val Glu Ser Gly Glu Val Leu
            180                 185                 190

Gln Ile Ser Arg Thr Ser Ser Asp Asp Thr Gly Ile Asp Glu Cys Pro
        195                 200                 205

Val Arg Leu Pro Gly Ser Gln Glu Lys Ala Ile Leu Gly Arg Cys Val
    210                 215                 220

```
Val Pro Leu Thr Glu Glu Val Ala Val Ala Pro Glu Pro Glu Pro
225                 230                 235                 240

Val Ile Ala Ala Val Ala Ala Pro Pro Ala Asn Tyr Ser Ser Arg Gly
            245                 250                 255

Trp Leu Ala Pro Glu Gln Gln Gln Arg Ile Tyr Arg Gly Asn Ala Ser
                260                 265                 270

<210> SEQ ID NO 19
<211> LENGTH: 279
<212> TYPE: PRT
<213> ORGANISM: Geminocystis herdmanii

<400> SEQUENCE: 19

Met Lys Lys Ile Ile Glu Gly Leu His Arg Phe Gln Ala Gly Tyr Phe
1               5                   10                  15

Glu Ser His Arg Asp Leu Phe Glu Gln Leu Ser His Gly Gln His Pro
            20                  25                  30

Arg Ile Leu Phe Ile Thr Cys Ser Asp Ser Arg Ile Asp Pro Asn Leu
        35                  40                  45

Ile Thr Gln Ala Asn Val Gly Glu Leu Phe Val Ile Arg Asn Ala Gly
50                  55                  60

Asn Ile Ile Pro Pro Phe Gly Ala Thr Asn Gly Gly Glu Gly Ala Ser
65                  70                  75                  80

Ile Glu Tyr Ala Ile Thr Ala Leu Asp Ile Gln Val Ile Val Cys
                85                  90                  95

Gly His Ser His Cys Gly Ala Met Lys Gly Leu Leu Lys Met Ser Lys
            100                 105                 110

Leu Ala Asp Lys Met Pro Leu Val Tyr Glu Trp Leu Lys Gln Ala Glu
        115                 120                 125

Ala Thr Arg Arg Leu Ile Ile Asp Asn Tyr Ser His Leu Glu Gly Glu
    130                 135                 140

Glu Leu Leu Gln Ile Thr Val Ala Glu Asn Val Leu Thr Gln Leu Glu
145                 150                 155                 160

Asn Leu Asn Thr Tyr Pro Ile Val Arg Ser Arg Leu His Gln Gly Arg
                165                 170                 175

Leu Ser Leu His Gly Trp Ile Tyr Gly Ile Glu Thr Gly Glu Val Leu
            180                 185                 190

Thr Tyr Asp Pro Lys Val His Asp Phe Val Asn Leu Glu Ser Arg Thr
        195                 200                 205

Asp Asn Ser Glu Tyr Ile Tyr Asn Leu His Pro Ser Cys Ser Val Ala
    210                 215                 220

Lys Ser Met Phe Tyr Gly Ile Pro Asp Glu Asn Asp Lys Val Gln
225                 230                 235                 240

Pro Ser Glu Pro Ile Pro Gln Thr Ile Asn Pro Asn Leu Pro Arg Ser
                245                 250                 255

Arg Ser Gly Ala Ala Arg Ser Asn Arg Leu Ser Pro Glu Gln Glu Gln
            260                 265                 270

Arg Ile Tyr Arg Gly Ser Thr
        275

<210> SEQ ID NO 20
<211> LENGTH: 275
<212> TYPE: PRT
<213> ORGANISM: Aliterella atlantica
```

```
<400> SEQUENCE: 20

Met Arg Lys Leu Ile Lys Gly Leu Arg Ala Phe Lys Asp Asn Tyr Tyr
1               5                   10                  15

Ser Asn His Leu Glu Leu Phe Glu Lys Leu Thr His Ala Gln Lys Pro
            20                  25                  30

Arg Val Leu Phe Ile Thr Cys Ser Asp Ser Arg Ile Asp Pro Asn Leu
        35                  40                  45

Ile Thr Gln Ala Ala Val Gly Glu Leu Phe Val Ile Arg Asn Ala Gly
50                  55                  60

Asn Ile Ile Pro Pro Phe Gly Ala Thr Asn Gly Glu Gly Ala Thr
65                  70                  75                  80

Val Glu Tyr Ala Val His Ala Leu Gly Ile Glu Gln Ile Val Val Cys
            85                  90                  95

Gly His Ser His Cys Gly Ala Met Lys Gly Leu Leu Lys Leu Asn Lys
            100                 105                 110

Leu Gln Gln Asp Met Pro Leu Val Tyr Asn Trp Leu Gln Tyr Ala Glu
        115                 120                 125

Ser Thr Arg Arg Leu Val Gln Glu Asn Tyr Asn Ser Tyr Ser Glu Glu
130                 135                 140

Glu Leu Val Glu Ile Ala Val Ala Glu Asn Val Leu Thr Gln Ile Glu
145                 150                 155                 160

Asn Leu Lys Thr Tyr Pro Val Val Arg Ser Lys Leu Tyr Gln Gly Lys
            165                 170                 175

Leu Gln Ile Tyr Ala Trp Ile Tyr His Leu Glu Thr Gly Glu Val Leu
        180                 185                 190

Ala Tyr Asp Pro Gln Ser His Ala Tyr Val Ala Pro Gln Ser Gln Leu
    195                 200                 205

Met Asn Gly Asp Thr Thr Glu Ser Ile Glu Thr Arg Ile Ala Asn Thr
210                 215                 220

Ser Ala Pro Ile Val Ala Cys Glu Phe Pro Ser Arg His Lys Gln Arg
225                 230                 235                 240

Gln Val Ala His Asn Thr Ala Asn Asn Asp Gly Asp Thr Leu Pro Asp
            245                 250                 255

Met Trp Leu Ser Pro Gln Gln Ala Glu Arg Ile Tyr Arg Gly Ser Asn
        260                 265                 270

Gly Asn Arg
        275

<210> SEQ ID NO 21
<211> LENGTH: 279
<212> TYPE: PRT
<213> ORGANISM: Leptolyngbya boryana

<400> SEQUENCE: 21

Met Lys Lys Leu Ile Gln Gly His Gln Gln Phe Trp Glu Ser Tyr Val
1               5                   10                  15

Pro Ser His Leu Asp Gln Leu Glu Glu Leu Ser His Gly Gln Lys Pro
            20                  25                  30

Arg Val Leu Phe Ile Thr Cys Ser Asp Ser Arg Ile Asp Pro Asn Leu
        35                  40                  45

Ile Thr Gln Ala Gly Ile Gly Glu Leu Phe Val Ile Arg Asn Ala Gly
50                  55                  60

Asn Ile Ile Pro Pro Phe Gly Ala Ala Asn Gly Gly Glu Gly Ala Ala
65                  70                  75                  80
```

-continued

Val Glu Tyr Ala Ile Ala Ala Leu Asp Ile Gln Gln Ile Ile Val Cys
            85                  90                  95

Gly His Ser His Cys Gly Ala Met Lys Gly Leu Leu Lys Leu Asn Lys
                100                 105                 110

Leu Gln Glu Asp Met Pro Leu Val Tyr Asp Trp Leu Lys His Ala Glu
            115                 120                 125

Ala Thr Arg Arg Leu Val Lys Glu Asn Tyr Ser Gln Tyr Ser Gly Glu
        130                 135                 140

Glu Leu Leu Glu Ile Thr Ile Ala Glu Asn Val Leu Thr Gln Ile Glu
145                 150                 155                 160

Asn Leu Lys Thr Tyr Pro Val Val His Ser Arg Leu Tyr Gln Gly Lys
                165                 170                 175

Leu Glu Ile Tyr Gly Trp Val Tyr His Ile Glu Thr Gly Glu Leu Leu
            180                 185                 190

Ala Phe Asp Pro Glu Thr His Ala Tyr Val Pro Pro Gln Ser Gln Leu
        195                 200                 205

Ser Pro Arg Glu Leu Gly Ala Phe Tyr Glu Lys Thr Ser Ala Pro Pro
    210                 215                 220

Val Ala Cys Asn Leu Pro His Lys Glu Asp Asn Gly Asn Gly Gln Leu
225                 230                 235                 240

Arg Gln Pro Val Thr Ile Arg Ser Gln Val Lys Ser Ala Glu Pro Val
                245                 250                 255

Pro Gln Thr Glu Val Met Pro Trp Leu Thr Ala Glu Gln Ala Gln Arg
            260                 265                 270

Ile Tyr Gln Gly Ser Lys Arg
        275

<210> SEQ ID NO 22
<211> LENGTH: 608
<212> TYPE: PRT
<213> ORGANISM: Artificial Sequence
<220> FEATURE:
<223> OTHER INFORMATION: A synthetic protein

<400> SEQUENCE: 22

Met Thr Val Ser Ala Tyr Asn Gly Gln Gly Arg Leu Ser Ser Glu Val
1               5                   10                  15

Ile Thr Gln Val Arg Ser Leu Leu Asn Gln Gly Tyr Arg Ile Gly Thr
            20                  25                  30

Glu His Ala Asp Lys Arg Arg Phe Arg Thr Ser Ser Trp Gln Pro Cys
        35                  40                  45

Ala Pro Ile Gln Ser Thr Asn Glu Arg Gln Val Leu Ser Glu Leu Glu
    50                  55                  60

Asn Cys Leu Ser Glu His Glu Gly Glu Tyr Val Arg Leu Leu Gly Ile
65                  70                  75                  80

Asp Thr Asn Thr Arg Ser Arg Val Phe Glu Ala Leu Ile Gln Arg Pro
                85                  90                  95

Asp Gly Ser Val Pro Glu Ser Leu Gly Ser Gln Pro Val Ala Val Ala
            100                 105                 110

Ser Gly Gly Gly Arg Gln Ser Ser Tyr Ala Ser Val Ser Gly Asn Leu
        115                 120                 125

Ser Ala Glu Val Val Asn Lys Val Arg Asn Leu Leu Ala Gln Gly Tyr
    130                 135                 140

Arg Ile Gly Thr Glu His Ala Asp Lys Arg Arg Phe Arg Thr Ser Ser
145                 150                 155                 160

-continued

Trp Gln Ser Cys Ala Pro Ile Gln Ser Ser Asn Glu Arg Gln Val Leu
                165                 170                 175
Ala Glu Leu Glu Asn Cys Leu Ser Glu His Glu Gly Glu Tyr Val Arg
            180                 185                 190
Leu Leu Gly Ile Asp Thr Ala Ser Arg Ser Arg Val Phe Glu Ala Leu
        195                 200                 205
Ile Gln Asp Pro Gln Gly Pro Val Gly Ser Ala Lys Ala Ala Ala Ala
    210                 215                 220
Pro Val Ser Ser Ala Thr Pro Ser Ser His Ser Tyr Thr Ser Asn Gly
225                 230                 235                 240
Ser Ser Ser Ser Asp Val Ala Gly Gln Val Arg Gly Leu Leu Ala Gln
                245                 250                 255
Gly Tyr Arg Ile Ser Ala Glu Val Ala Asp Lys Arg Arg Phe Gln Thr
                260                 265                 270
Ser Ser Trp Gln Ser Leu Pro Ala Leu Ser Gly Gln Ser Glu Ala Thr
            275                 280                 285
Val Leu Pro Ala Leu Glu Ser Ile Leu Gln Glu His Lys Gly Lys Tyr
        290                 295                 300
Val Arg Leu Ile Gly Ile Asp Pro Ala Ala Arg Arg Arg Val Ala Glu
305                 310                 315                 320
Leu Leu Ile Gln Lys Pro Gly Ser Arg Lys Leu Ile Glu Gly Leu Arg
                325                 330                 335
His Phe Arg Thr Ser Tyr Tyr Pro Ser His Arg Asp Leu Phe Glu Gln
                340                 345                 350
Phe Ala Lys Gly Gln His Pro Arg Val Leu Phe Ile Thr Cys Ser Asp
            355                 360                 365
Ser Arg Ile Asp Pro Asn Leu Ile Thr Gln Ser Gly Met Gly Glu Leu
        370                 375                 380
Phe Val Ile Arg Asn Ala Gly Asn Leu Ile Pro Pro Phe Gly Ala Ala
385                 390                 395                 400
Asn Gly Gly Glu Gly Ala Ser Ile Glu Tyr Ala Ile Ala Ala Leu Asn
                405                 410                 415
Ile Glu His Val Val Cys Gly His Ser His Cys Gly Ala Met Lys
                420                 425                 430
Gly Leu Leu Lys Leu Asn Gln Leu Gln Glu Asp Met Pro Leu Val Tyr
            435                 440                 445
Asp Trp Leu Gln His Ala Gln Ala Thr Arg Arg Leu Val Leu Asp Asn
        450                 455                 460
Tyr Ser Gly Tyr Glu Thr Asp Asp Leu Val Glu Ile Leu Val Ala Glu
465                 470                 475                 480
Asn Val Leu Thr Gln Ile Glu Asn Leu Lys Thr Tyr Pro Ile Val Arg
                485                 490                 495
Ser Arg Leu Phe Gln Gly Lys Leu Gln Ile Phe Gly Trp Ile Tyr Glu
            500                 505                 510
Val Glu Ser Gly Glu Val Leu Gln Ile Ser Arg Thr Ser Ser Asp Asp
        515                 520                 525
Thr Gly Ile Asp Glu Cys Pro Val Arg Leu Pro Gly Ser Gln Glu Lys
    530                 535                 540
Ala Ile Leu Gly Arg Cys Val Val Pro Leu Thr Glu Glu Val Ala Val
545                 550                 555                 560
Ala Pro Pro Glu Pro Glu Pro Val Ile Ala Ala Val Ala Ala Pro Pro
                565                 570                 575

```
Ala Asn Tyr Ser Ser Arg Gly Trp Leu Gly Ser Gly Gly Ser Val Tyr
            580                 585                 590

Gly Lys Glu Gln Phe Leu Arg Met Arg Gln Ser Met Phe Pro Asp Arg
        595                 600                 605

<210> SEQ ID NO 23
<211> LENGTH: 113
<212> TYPE: PRT
<213> ORGANISM: Synechococcus elongatus

<400> SEQUENCE: 23

Met Ser Gln Gln Ala Ile Gly Ser Leu Glu Thr Lys Gly Phe Pro Pro
1               5                   10                  15

Ile Leu Ala Ala Ala Asp Ala Met Val Lys Ala Gly Arg Ile Thr Ile
            20                  25                  30

Val Ser Tyr Met Arg Ala Gly Ser Ala Arg Phe Ala Val Asn Ile Arg
        35                  40                  45

Gly Asp Val Ser Glu Val Lys Thr Ala Met Asp Ala Gly Ile Glu Ala
    50                  55                  60

Ala Lys Asn Thr Pro Gly Gly Thr Leu Glu Thr Trp Val Ile Ile Pro
65                  70                  75                  80

Arg Pro His Glu Asn Val Glu Ala Val Phe Pro Ile Gly Phe Gly Pro
                85                  90                  95

Glu Val Glu Gln Tyr Arg Leu Ser Ala Glu Gly Thr Gly Ser Gly Arg
            100                 105                 110

Arg

<210> SEQ ID NO 24
<211> LENGTH: 99
<212> TYPE: PRT
<213> ORGANISM: Synechococcus elongatus

<400> SEQUENCE: 24

Met Arg Ile Ala Lys Val Arg Gly Thr Val Val Ser Thr Tyr Lys Glu
1               5                   10                  15

Pro Ser Leu Gln Gly Val Lys Phe Leu Val Val Gln Phe Leu Asp Glu
            20                  25                  30

Ala Gly Gln Ala Leu Gln Glu Tyr Glu Val Ala Ala Asp Met Val Gly
        35                  40                  45

Ala Gly Val Asp Glu Trp Val Leu Ile Ser Arg Gly Ser Gln Ala Arg
    50                  55                  60

His Val Arg Asp Cys Gln Glu Arg Pro Val Ala Ala Val Ile Ala
65                  70                  75                  80

Ile Ile Asp Thr Val Asn Val Glu Asn Arg Ser Val Tyr Asp Lys Arg
                85                  90                  95

Glu His Ser

<210> SEQ ID NO 25
<211> LENGTH: 472
<212> TYPE: PRT
<213> ORGANISM: Synechococcus elongatus

<400> SEQUENCE: 25

Met Pro Lys Thr Gln Ser Ala Ala Gly Tyr Lys Ala Gly Val Lys Asp
1               5                   10                  15

Tyr Lys Leu Thr Tyr Tyr Thr Pro Asp Tyr Thr Pro Lys Asp Thr Asp
            20                  25                  30
```

```
Leu Leu Ala Ala Phe Arg Phe Ser Pro Gln Pro Gly Val Pro Ala Asp
         35                  40                  45
Glu Ala Gly Ala Ala Ile Ala Ala Glu Ser Ser Thr Gly Thr Trp Thr
 50                  55                  60
Thr Val Trp Thr Asp Leu Leu Thr Asp Met Asp Arg Tyr Lys Gly Lys
 65                  70                  75                  80
Cys Tyr His Ile Glu Pro Val Gln Gly Glu Glu Asn Ser Tyr Phe Ala
                 85                  90                  95
Phe Ile Ala Tyr Pro Leu Asp Leu Phe Glu Glu Gly Ser Val Thr Asn
            100                 105                 110
Ile Leu Thr Ser Ile Val Gly Asn Val Phe Gly Phe Lys Ala Ile Arg
        115                 120                 125
Ser Leu Arg Leu Glu Asp Ile Arg Phe Pro Val Ala Leu Val Lys Thr
    130                 135                 140
Phe Gln Gly Pro Pro His Gly Ile Gln Val Glu Arg Asp Leu Leu Asn
145                 150                 155                 160
Lys Tyr Gly Arg Pro Met Leu Gly Cys Thr Ile Lys Pro Lys Leu Gly
                165                 170                 175
Leu Ser Ala Lys Asn Tyr Gly Arg Ala Val Tyr Glu Cys Leu Arg Gly
            180                 185                 190
Gly Leu Asp Phe Thr Lys Asp Asp Glu Asn Ile Asn Ser Gln Pro Phe
        195                 200                 205
Gln Arg Trp Arg Asp Arg Phe Leu Phe Val Ala Asp Ala Ile His Lys
    210                 215                 220
Ser Gln Ala Glu Thr Gly Glu Ile Lys Gly His Tyr Leu Asn Val Thr
225                 230                 235                 240
Ala Pro Thr Cys Glu Glu Met Met Lys Arg Ala Glu Phe Ala Lys Glu
                245                 250                 255
Leu Gly Met Pro Ile Ile Met His Asp Phe Leu Thr Ala Gly Phe Thr
            260                 265                 270
Ala Asn Thr Thr Leu Ala Lys Trp Cys Arg Asp Asn Gly Val Leu Leu
        275                 280                 285
His Ile His Arg Ala Met His Ala Val Ile Asp Arg Gln Arg Asn His
    290                 295                 300
Gly Ile His Phe Arg Val Leu Ala Lys Cys Leu Arg Leu Ser Gly Gly
305                 310                 315                 320
Asp His Leu His Ser Gly Thr Val Val Gly Lys Leu Glu Gly Asp Lys
                325                 330                 335
Ala Ser Thr Leu Gly Phe Val Asp Leu Met Arg Glu Asp His Ile Glu
            340                 345                 350
Ala Asp Arg Ser Arg Gly Val Phe Phe Thr Gln Asp Trp Ala Ser Met
        355                 360                 365
Pro Gly Val Leu Pro Val Ala Ser Gly Gly Ile His Val Trp His Met
    370                 375                 380
Pro Ala Leu Val Glu Ile Phe Gly Asp Asp Ser Val Leu Gln Phe Gly
385                 390                 395                 400
Gly Gly Thr Leu Gly His Pro Trp Gly Asn Ala Pro Gly Ala Thr Ala
                405                 410                 415
Asn Arg Val Ala Leu Glu Ala Cys Val Gln Ala Arg Asn Glu Gly Arg
            420                 425                 430
Asp Leu Tyr Arg Glu Gly Gly Asp Ile Leu Arg Glu Ala Gly Lys Trp
        435                 440                 445
```

Ser Pro Glu Leu Ala Ala Ala Leu Asp Leu Trp Lys Glu Ile Lys Phe
    450                 455                 460

Glu Phe Glu Thr Met Asp Lys Leu
465                 470

<210> SEQ ID NO 26
<211> LENGTH: 1827
<212> TYPE: DNA
<213> ORGANISM: Synechococcus elongatus

<400> SEQUENCE: 26

| | |
|---|---|
| atgaccgtga gcgcttataa cggccaaggc cgactcagtt ccgaagtcat cacccaagtc | 60 |
| cggagtttgc tgaaccaggg ctatcggatt gggacggaac atgcggacaa gcgccgcttc | 120 |
| cggactagct cttggcagcc ctgcgcgccg attcaaagca cgaacgagcg ccaggtcttg | 180 |
| agcgaactgg aaaattgtct gagcgaacac gaaggtgaat acgttcgctt gctcggcatc | 240 |
| gataccaata ctcgcagccg tgtttttgaa gccctgattc aacggcccga tggttcggtt | 300 |
| cctgaatcgc tggggagcca accggtggca gtcgcttccg gtggtggccg tcagagcagc | 360 |
| tatgccagcg tcagcggcaa cctctcagca gaagtggtca ataaagtccg caacctctta | 420 |
| gcccaaggct atcggattgg gacggaacat gcagacaagc gccgcttccg gactagctct | 480 |
| tggcagtcct gcgcaccgat tcaaagttcg aatgagcgcc aggttctggc tgaactggaa | 540 |
| aactgtctga gcgagcacga aggtgagtac gttcgcctgc tgggcatcga cactgctagc | 600 |
| cgcagtcgtg tttttgaagc cctgatccaa gatcccaag accgtgtggg ttccgccaaa | 660 |
| gcggccgccg cacctgtgag ttcggcaacg cccagcagcc acagctacac ctcaaatgga | 720 |
| tcgagttcga gcgatgtcgc tggacaggtt cggggtctgc tagcccaagg ctaccggatc | 780 |
| agtgcggaag tcgccgataa gcgtcgcttc caaaccagct cttggcagag tttgccggct | 840 |
| ctgagtggcc agagcgaagc aactgtcttg cctgctttgg agtcaattct gcaagagcac | 900 |
| aagggtaagt atgtgcgcct gattgggatt gaccctgcgg ctcgtcgtcg cgtggctgaa | 960 |
| ctgttgattc aaaagccggg atctcgcaag ctcatcgagg ggttacggca tttccgtacg | 1020 |
| tcctactacc cgtctcatcg ggacctgttc gagcagtttg ccaaaggtca gcaccctcga | 1080 |
| gtcctgttca ttacctgctc agactcgcgc attgaccta acctcattac ccagtcgggc | 1140 |
| atgggtgagc tgttcgtcat cgcaacgct ggcaatctga tcccgcccct cggtgccgcc | 1200 |
| aacggtggtg aagggcatc gatcgaatac gcgatcgcag cttttgaacat tgagcatgtt | 1260 |
| gtggtctgcg gtcactcgca ctgcggtgcg atgaaagggc tgctcaagct caatcagctg | 1320 |
| caagaggaca tgccgctggt ctatgactgg ctgcagcatg cccaagccac ccgccgccta | 1380 |
| gtcttggata actacagcgg ttatgagact gacgacttgg tagagattct ggtcgccgag | 1440 |
| aatgtgctga cgcagatcga gaaccttaag acctacccga tcgtgcgatc gcgccttttc | 1500 |
| caaggcaagc tgcagatttt tggctggatt tatgaagttg aaagcggcga ggtcttgcag | 1560 |
| attagccgta ccagcagtga tgacacaggc attgatgaat gtccagtgcg tttgcccggc | 1620 |
| agccaggaga aagccattct cggtcgttgt gtcgtccccc tgaccgaaga gtggccgtt | 1680 |
| gctccaccag agcggagcc tgtgatcgcg gctgtggcgg ctccaccgc caactactcc | 1740 |
| agtcgcggtt ggttgggatc tggaggcagt gtctacggca aggaacagtt tttgcggatg | 1800 |
| cgccagagca tgttccccga tcgctaa | 1827 |

<210> SEQ ID NO 27
<211> LENGTH: 1827
<212> TYPE: DNA
<213> ORGANISM: Escherichia coli

<400> SEQUENCE: 27

| | | | | | |
|---|---|---|---|---|---|
| atgaccgttt | ccgcgtacaa | cggacagggc | agactttcga | gtgaagttat | aacccaggtc | 60 |
| cggtctttgt | tgaaccaagg | ctatcgcatc | gggaccgaac | atgccgataa | gcgccgtttc | 120 |
| cggacctcaa | gttggcaacc | gtgcgcgccc | atccagtcaa | ccaatgaacg | ccaggtattg | 180 |
| tctgaattag | agaattgctt | atcggaacac | gaaggagaat | acgttcgctt | gttaggaatt | 240 |
| gacactaaca | caagaagtcg | ggttttcgaa | gcactgatcc | agcgcccgga | cgggtctgtt | 300 |
| cctgaatctt | tgggcagcca | gccagtagca | gtggcttccg | gaggcggaag | acaatcgtcc | 360 |
| tatgcatctg | tttccggcaa | cttgtctgct | gaggttgtta | taaggtgcg | caacctgctt | 420 |
| gcccagggtt | acagaattgg | cacggagcac | gccgataagc | gccgttttag | aaccagctcg | 480 |
| tggcagtctt | gtgcgccgat | acagtcctcg | aatgaacggc | aggtgctggc | agagttagag | 540 |
| aattgcctga | gtgagcatga | aggagaatac | gtccgccttc | tgggcattga | caccgcttcc | 600 |
| cgttcgcgtg | ttttcgaagc | ccttattcag | gatccgcaag | ccccgtggg | ttccgccaaa | 660 |
| gctgccgcag | cacctgtatc | aagtgctacc | ccttcgtccc | acagttatac | gtcgaacggc | 720 |
| agctcatcat | ctgacgtggc | gggccaggtt | cgtgggttgt | tggctcaagg | gtatcggata | 780 |
| tcggctgagg | ttgcggataa | acgtcggttc | caaacatcgt | cgtggcagtc | cttgcctgca | 840 |
| ttatcgggtc | aatcggaagc | aacggtcctt | cctgcgctgg | agagtatcct | tcaggagcac | 900 |
| aagggcaagt | acgtcagatt | gatagggatc | gatccggcgg | cgcggagacg | ggtggcagaa | 960 |
| ttgcttatcc | aaaaacccgg | ttcgcgcaag | ttgatcgaag | gattaagaca | ttttagaacc | 1020 |
| tcatattacc | cgagtcatag | agatttattc | gagcagtttg | caaagggtca | acaccctaga | 1080 |
| gtcctgttca | tcacttgctc | ggattcacgg | atcgatccta | atttgatcac | gcagtctggt | 1140 |
| atgggagagc | ttttcgtcat | ccgtaacgca | ggtaacctga | ttccacctt | cggcgcggca | 1200 |
| aatgggggtg | agggtgcgtc | cattgaatat | gccatcgccg | cattgaatat | cgaacacgta | 1260 |
| gttgtatgtg | gccactcgca | ctgtggagcg | atgaaagggc | tgctgaagct | taaccagctg | 1320 |
| caagaagaca | tgccccttgt | ttacgattgg | ttgcaacacg | cgcaggccac | gagacgtctg | 1380 |
| gtccttgaca | actacagcgg | atatgaaacg | gacgaccttg | tcgagatcct | ggtcgccgag | 1440 |
| aacgtattga | cccaaataga | gaatctgaag | acctacccaa | ttgtgcgctc | gcgcttgttc | 1500 |
| cagggtaagt | tacaaatttt | cggttggatc | tatgaagtga | aaagtggaga | ggtcttgcaa | 1560 |
| atctcacgta | catcctcgga | cgacacagga | atagacgagt | gccccgtccg | tttaccggga | 1620 |
| tcgcaagaga | aggccatttt | aggacggtgc | gtcgtgccac | tgacagagga | agtggctgtt | 1680 |
| gccctccag | aaccagagcc | tgtcattgct | gcggtggccg | caccacccgc | gaattactcc | 1740 |
| agtcgcggtt | ggctgggctc | tggaggctct | gtctacggaa | aggaacaatt | ccttcgtatg | 1800 |
| cggcaatcaa | tgttcccgga | ccgctaa | | | | 1827 |

<210> SEQ ID NO 28
<211> LENGTH: 1827
<212> TYPE: DNA
<213> ORGANISM: Nicotiana tabacum

<400> SEQUENCE: 28

```
atgactgtga gtgcatataa tggacaaggt agattgagtt ctgaagtgat aactcaagtg    60
cgtagccttt tgaatcaagg atacagaatt gggaccgaac acgcagataa agaaggttt    120
agaaccagtt catggcagcc atgcgccccc atccagtcta ctaatgaaag acaagtgctt   180
tctgagctgg aaaactgtct tagtgaacat gaaggcgagt atgtgcgatt gctgggtatc   240
gatactaaca ctcgtagccg tgtttttgaa gctctgatac aacgacctga cggtagtgtc   300
cccgaatcac tgggtagcca gcccgtagca gtagctagcg ggggcgggcg acagtcctcc   360
tacgcctctg ttagcggcaa cctctcagcc gaagtagtga acaaagtaag aaacctcctc   420
gcccagggtt accgtatagg aaccgagcac gcagacaaac gaagattcag gactagcagc   480
tggcaatcct gcgcacccat acaatcttcc aacgaaagac aggtactggc agaattggaa   540
aactgtcttt cagaacatga aggcgagtac gtccgtctgc tggggatcga cacagcaagc   600
agaagccgag tatttgaagc cctcattcaa gatccacagg gccagtagg tagtgcaaag    660
gcagctgcag ctcccgtttc atctgctact cccagcagtc acagctacac ttctaatggg   720
tcttccagta gtgacgtcgc cggacaggta agaggcctgt tggcacaggg ttaccgaata   780
tctgccgaag tagctgataa aaggcgattc cagacttcat cctggcagtc ccttcctgca   840
ttgtctggcc aatctgaagc cactgttctt cctgcacttg aatccatttt gcaggaacat   900
aaaggtaagt atgttcgatt gatcggtatc gatccagctg cacgtagaag ggttgcagag   960
ttattgattc agaagccagg atctcgaaaa ttaatagagg gtttacgaca tttcagaact  1020
tcttactacc cttcccatcg tgacttattc gagcaatttg caaaaggcca acatcccaga  1080
gtcttgttta tcacttgttc agactctcga atagacccca atctcataac acagtctgga  1140
atgggcgagc ttttcgtgat acgtaacgcc ggcaacctca ttcctccctt tggtgcagct  1200
aacgggggcg aggggcttc aatagagtac gctatcgctg ccctcaatat cgaacacgtc   1260
gtagtatgcg gacattcaca ttgcggggcc atgaagggac tgttgaagct gaatcaactc  1320
caagaggaca tgccctggt ctatgattgg ttgcagcacg cccaagctac taggagatta   1380
gttttagaca actactctgg ctatgaaact gatgacctgg tagaaatact ggtcgcagaa  1440
acgtattaa ctcagataga aaatttaaag acttatccca tagtccgtag ccgattgttc    1500
caaggaaaat tgcaaatatt cgggtggatc tatgaggttg agtccggaga ggtcttgcag  1560
ataagtcgaa ctagctccga cgacacaggg atagacgaat gcccagtcag gttgcccggg  1620
tctcaagaga aagctatctt ggggaggtgt gtcgttcctt taaccgagga agttgctgtc   1680
gccccccctg agcctgaacc tgtgatagct gccgtagccg caccccctgc caactattca   1740
tcacgaggct ggcttggctc aggggctca gtttatggga aggaacaatt cctgaggatg    1800
agacagtcaa tgttccccga tagataa                                       1827
```

<210> SEQ ID NO 29
<211> LENGTH: 1827
<212> TYPE: DNA
<213> ORGANISM: Chlamydomonas reinhardtii

<400> SEQUENCE: 29

```
atgacggtgt cggcttacaa cggccagggc cgcctctcgt ccgaggtcat tacgcaggtc    60
cggagcctcc tgaaccaggg gtaccggatt ggtaccgagc atgccgacaa gcggcgcttt   120
cggacgtcgt cctggcagcc ctgcgcgccc attcagagca ccaacgagcg gcaggtcctc   180
tccgagctgg agaactgcct cagcgagcat gaggggagt acgtccgcct gctggggatc    240
```

```
gatacgaaca cgcgctcccg ggtcttcgag gctctcatcc agcgccctga cggctcggtg      300
cctgagagcc tcggctcgca gcctgtggcc gtggcgagcg gcggtgggcg gcagtccagc      360
tacgccagcg tgtcgggtaa cctctccgcc gaggtcgtca caaggtgcg gaacctcctg       420
gcccagggct accggatcgg taccgagcac gccgacaagc gccgctttcg cacgagctcg      480
tggcagagct gcgcccccat tcagtcgagc aacgagcggc aggtgctcgc tgagctggag      540
aactgcctct ccgagcatga gggcgagtac gtgcggctgc tcgggattga tacgcctcg      600
cggtcgcgcg tgtttgaggc gctgatccag gaccccagg gtcctgtcgg ttcggctaag       660
gctgcggctg cccctgtgtc ctcggccacc cccagctcgc attcgtacac ctcgaacggc      720
tcctcgtcgt ccgatgtggc gggtcaggtg cgcgggctcc tcgctcaggg ctaccgcatc      780
agcgctgagg tcgccgataa gcggcggttt cagacgagct cgtggcagtc cctcccggcg      840
ctctcgggtc agagcgaggc caccgtcctc cctgctctcg agtcgattct ccaggagcat      900
aaggggaagt acgtccggct catcgggatt gacccggctg ctcggcgccg cgtggcggag      960
ctgctgattc agaagcctgg cagccggaag ctcatcgagg ggctccgcca tttccggacg     1020
tcctactacc cctcccaccg cgatctcttc gagcagtttg ccaaggggca gcaccccgcgg    1080
gtcctgttca ttacgtgctc cgatagccgc attgacccga acctcatcac gcagagcggt    1140
atgggtgagc tctttgtgat tcgcaacgct ggtaacctca ttcctcccct tggggcggcg    1200
aacggcggcg agggtgcgtc gattgagtac gctatcgccg ccctcaacat tgagcatgtc    1260
gtggtgtgcg gtcatagcca ttgcggcgcg atgaagggcc tcctcaagct gaaccagctg    1320
caggaggaca tgcctctggt gtacgactgg ctgcagcatg ctcaggctac gcggcgcctc    1380
gtcctggaca actactcggg ctacgagacc gatgacctcg tcgagatcct cgtcgcggag    1440
aacgtgctga cccagattga gaacctcaag acgtaccca tcgtgcgctc gcgcctcttc    1500
cagggcaagc tgcagatctt cggttggatt tacgaggtgg agtcggggga ggtcctgcag    1560
atcagccgga cgagctccga cgacaccggg atcgatgagt gccctgtccg cctgccgggc    1620
tcgcaggaga aggccattct gggtcggtgc gtggtccccc tgacggagga ggtggctgtg    1680
gctcctcccg agcctgagcc cgtcattgcg cggtcgccg ccctccggc taactactcc      1740
agccggggt ggctcggctc cggggggagc gtctacggca aggagcagtt tctgcgcatg     1800
cggcagtcga tgttcccgga tcgctaa                                          1827
```

<210> SEQ ID NO 30
<211> LENGTH: 190
<212> TYPE: PRT
<213> ORGANISM: Vibrio fishcheri

<400> SEQUENCE: 30

```
Met Ile Lys Lys Ser Asp Phe Leu Gly Ile Pro Ser Glu Glu Tyr Arg
1               5                   10                  15

Gly Ile Leu Ser Leu Arg Tyr Gln Val Phe Lys Arg Arg Leu Glu Trp
            20                  25                  30

Asp Leu Val Ser Glu Asp Asn Leu Glu Ser Asp Glu Tyr Asp Asn Ser
        35                  40                  45

Asn Ala Glu Tyr Ile Tyr Ala Cys Asp Asp Ala Glu Glu Val Asn Gly
    50                  55                  60

Cys Trp Arg Leu Leu Pro Thr Thr Gly Asp Tyr Met Leu Lys Thr Val
65                  70                  75                  80

Phe Pro Glu Leu Leu Gly Asp Gln Val Ala Pro Arg Asp Pro Asn Ile
                85                  90                  95
```

Val Glu Leu Ser Arg Phe Ala Val Gly Lys Asn Ser Lys Ile Asn
            100                 105                 110

Asn Ser Ala Ser Glu Ile Thr Met Lys Leu Phe Gln Ala Ile Tyr Lys
            115                 120                 125

His Ala Val Ser Gln Gly Ile Thr Glu Tyr Val Thr Val Thr Ser Ile
        130                 135                 140

Ala Ile Glu Arg Phe Leu Lys Arg Ile Lys Val Pro Cys His Arg Ile
145                 150                 155                 160

Gly Asp Lys Glu Ile His Leu Leu Gly Asn Thr Arg Ser Val Val Leu
                165                 170                 175

Ser Met Pro Ile Asn Asp Gln Phe Arg Lys Ala Val Ser Asn
            180                 185                 190

<210> SEQ ID NO 31
<211> LENGTH: 573
<212> TYPE: DNA
<213> ORGANISM: Vibrio fishcheri

<400> SEQUENCE: 31
atgataaaaa aatcggactt tttgggcatt ccatcagagg agtatagagg tattcttagt      60
cttcgttatc aggtatttaa cgaagactg gagtgggact tggtaagtga ggataatctt     120
gaatcagatg aatatgataa ctcaaatgca gaatatattt atgcttgtga tgatgcggaa    180
gaggtaaatg ctgttggcg tttgttacct acaacgggtg attacatgtt aaaaactgtt    240
tttcctgaat tgctcggaga tcaagtagcc ccaagagatc aaatatagt cgaattaagc     300 cgttttgctg tgggaaaaaa tagctcaaaa ataaataact ctgctagtga ataacaatg     360 aaattgtttc aagctatata taaacacgca gttagtcaag gtattacaga atatgtaaca    420
gtaacatcaa tagcaataga gcgatttctg aaacgtatta agttccttg tcatcgcatt     480 ggtgataagg agattcattt attaggtaat actagatctg ttgtattgtc tatgcctatt    540
aatgatcagt ttagaaaagc tgtatcaaat taa                                 573

<210> SEQ ID NO 32
<211> LENGTH: 269
<212> TYPE: PRT
<213> ORGANISM: Vibrio fishcheri

<400> SEQUENCE: 32

Met Ile Tyr Asn Thr Gln Asn Leu Arg Gln Thr Ile Gly Lys Asp Lys
1                   5                   10                  15

Glu Met Gly Met Lys Asn Ile Asn Ala Asp Asp Thr Tyr Arg Ile Ile
            20                  25                  30

Asn Lys Ile Lys Ala Cys Arg Ser Asn Asn Asp Ile Asn Gln Cys Leu
        35                  40                  45

Ser Asp Met Thr Lys Met Val His Cys Glu Tyr Tyr Leu Leu Ala Ile
    50                  55                  60

Ile Tyr Pro His Ser Met Val Lys Ser Asp Ile Ser Ile Leu Asp Asn
65                  70                  75                  80

Tyr Pro Lys Lys Trp Arg Gln Tyr Tyr Asp Asp Ala Asn Leu Ile Lys
                85                  90                  95

Tyr Asp Pro Ile Val Asp Tyr Ser Asn Ser Asn His Ser Pro Ile Asn
            100                 105                 110

Trp Asn Ile Phe Glu Asn Asn Ala Val Asn Lys Lys Ser Pro Asn Val
        115                 120                 125

```
Ile Lys Glu Ala Lys Thr Ser Gly Leu Ile Thr Gly Phe Ser Phe Pro
        130                 135                 140

Ile His Thr Ala Asn Asn Gly Phe Gly Met Leu Ser Phe Ala His Ser
145                 150                 155                 160

Glu Lys Asp Asn Tyr Ile Asp Ser Leu Phe Leu His Ala Cys Met Asn
                165                 170                 175

Ile Pro Leu Ile Val Pro Ser Leu Val Asp Asn Tyr Arg Lys Ile Asn
            180                 185                 190

Ile Ala Asn Asn Lys Ser Asn Asn Asp Leu Thr Lys Arg Glu Lys Glu
        195                 200                 205

Cys Leu Ala Trp Ala Cys Glu Gly Lys Ser Ser Trp Asp Ile Ser Lys
    210                 215                 220

Ile Leu Gly Cys Ser Glu Arg Thr Val Thr Phe His Leu Thr Asn Ala
225                 230                 235                 240

Gln Met Lys Leu Asn Thr Thr Asn Arg Cys Gln Ser Ile Ser Lys Ala
                245                 250                 255

Ile Leu Thr Gly Ala Ile Asp Cys Pro Tyr Phe Lys Asn
            260                 265
```

```
<210> SEQ ID NO 33
<211> LENGTH: 810
<212> TYPE: DNA
<213> ORGANISM: Vibrio fishcheri

<400> SEQUENCE: 33
atgatatata acacgcaaaa cttgcgacaa acaataggta aggataaaga gatgggtatg      60
aaaaacataa atgccgacga cacatacaga ataattaata aaattaaagc ttgtagaagc     120
aataatgata ttaatcaatg cttatctgat atgactaaaa tggtacattg tgaatattat     180
ttactcgcga tcatttatcc tcattctatg gttaaatctg atatttcaat tctagataat     240
taccctaaaa aatggaggca atattatgat gacgctaatt aataaaaata tgatcctata     300
gtagattatt ctaactccaa tcattcacca attaattgga atatatttga aaacaatgct     360
gtaaataaaa aatctccaaa tgtaattaaa gaagcgaaaa catcaggtct tatcactggg     420
tttagtttcc ctattcatac ggctaacaat ggcttcggaa tgcttagttt tgcacattca     480
gaaaaagaca actatataga tagtttattt ttacatgcgt gtatgaacat accattaatt     540
gttccttctc tagttgataa ttatcgaaaa ataaatatag caataataa atcaaacaac      600
gatttaacca aaagagaaaa agaatgttta gcgtgggcat gcgaaggaaa aagctcttgg     660
gatatttcaa aaatattagg ctgcagtgag cgtactgtca ctttccattt aaccaatgcg     720
caaatgaaac tcaatacaac aaaccgctgc caaagtattt ctaaagcaat tttaacagga     780
gcaattgatt gcccatactt taaaaattaa                                      810

<210> SEQ ID NO 34
<211> LENGTH: 198
<212> TYPE: DNA
<213> ORGANISM: Vibrio fishcheri

<400> SEQUENCE: 34
tgtcgcaagt tttgcgtgtt atatatcatt aaaacggtaa tggattgaca tttgattcta      60
ataaattgga tttttgtcac actattgtat cgctgggaat acaattactt aacataagca     120
cctgtaggat cgtacaggtt tacgcaagaa aatggtttgt tatagtcgaa tgaattcatt     180
aaagaggaga aaggtacc                                                   198
```

-continued

```
<210> SEQ ID NO 35
<211> LENGTH: 39
<212> TYPE: DNA
<213> ORGANISM: Artificial Sequence
<220> FEATURE:
<223> OTHER INFORMATION: A synthetic oligonucleotide

<400> SEQUENCE: 35
tctagaaata attttgttta actttaagaa ggagatata                              39

<210> SEQ ID NO 36
<211> LENGTH: 598
<212> TYPE: PRT
<213> ORGANISM: Artificial Sequence
<220> FEATURE:
<223> OTHER INFORMATION: A synthetic protein

<400> SEQUENCE: 36

Met Arg Lys Leu Ile Glu Gly Leu Arg His Phe Arg Thr Ser Tyr Tyr
1               5                   10                  15

Pro Ser His Arg Asp Leu Phe Glu Gln Phe Ala Lys Gly Gln His Pro
            20                  25                  30

Arg Val Leu Phe Ile Thr Cys Ser Asp Ser Arg Ile Asp Pro Asn Leu
        35                  40                  45

Ile Thr Gln Ser Gly Met Gly Glu Leu Phe Val Ile Arg Asn Ala Gly
50                  55                  60

Asn Leu Ile Pro Pro Phe Gly Ala Ala Asn Gly Gly Glu Gly Ala Ser
65                  70                  75                  80

Ile Glu Tyr Ala Ile Ala Ala Leu Asn Ile Glu His Val Val Cys
                85                  90                  95

Gly His Ser His Cys Gly Ala Met Lys Gly Leu Leu Lys Leu Asn Gln
                100                 105                 110

Leu Gln Glu Asp Met Pro Leu Val Tyr Asp Trp Leu Gln His Ala Gln
            115                 120                 125

Ala Thr Arg Arg Leu Val Leu Asp Asn Tyr Ser Gly Tyr Glu Thr Asp
        130                 135                 140

Asp Leu Val Glu Ile Leu Val Ala Glu Asn Val Leu Thr Gln Ile Glu
145                 150                 155                 160

Asn Leu Lys Thr Tyr Pro Ile Val Arg Ser Arg Leu Phe Gln Gly Lys
                165                 170                 175

Leu Gln Ile Phe Gly Trp Ile Tyr Glu Val Glu Ser Gly Glu Val Leu
            180                 185                 190

Gln Ile Ser Arg Thr Ser Ser Asp Asp Thr Gly Ile Asp Glu Cys Pro
        195                 200                 205

Val Arg Leu Pro Gly Ser Gln Glu Lys Ala Ile Leu Gly Arg Cys Val
    210                 215                 220

Val Pro Leu Thr Glu Glu Val Ala Val Ala Pro Pro Glu Pro Glu Pro
225                 230                 235                 240

Val Ile Ala Ala Val Ala Ala Pro Ala Asn Tyr Ser Ser Arg Gly
                245                 250                 255

Trp Leu Ala Pro Glu Gln Gln Gln Arg Ile Tyr Arg Gly Asn Ala Ser
            260                 265                 270

Gly Ser Val Ser Ala Tyr Asn Gly Gln Gly Arg Leu Ser Ser Glu Val
        275                 280                 285

Ile Thr Gln Val Arg Ser Leu Leu Asn Gln Gly Tyr Arg Ile Gly Thr
    290                 295                 300
```

-continued

```
Glu His Ala Asp Lys Arg Arg Phe Arg Thr Ser Ser Trp Gln Pro Cys
305                 310                 315                 320

Ala Pro Ile Gln Ser Thr Asn Glu Arg Gln Val Leu Ser Glu Leu Glu
            325                 330                 335

Asn Cys Leu Ser Glu His Glu Gly Glu Tyr Val Arg Leu Leu Gly Ile
                340                 345                 350

Asp Thr Asn Thr Arg Ser Arg Val Phe Glu Ala Leu Ile Gln Arg Pro
            355                 360                 365

Asp Gly Ser Val Pro Glu Ser Leu Gly Ser Gln Pro Val Ala Val Ala
370                 375                 380

Ser Gly Gly Arg Gln Ser Ser Tyr Ala Ser Val Ser Gly Asn Leu
385                 390                 395                 400

Ser Ala Glu Val Val Asn Lys Val Arg Asn Leu Leu Ala Gln Gly Tyr
                405                 410                 415

Arg Ile Gly Thr Glu His Ala Asp Lys Arg Arg Phe Arg Thr Ser Ser
            420                 425                 430

Trp Gln Ser Cys Ala Pro Ile Gln Ser Ser Asn Glu Arg Gln Val Leu
            435                 440                 445

Ala Glu Leu Glu Asn Cys Leu Ser Glu His Glu Gly Glu Tyr Val Arg
450                 455                 460

Leu Leu Gly Ile Asp Thr Ala Ser Arg Ser Arg Val Phe Glu Ala Leu
465                 470                 475                 480

Ile Gln Asp Pro Gln Gly Pro Val Gly Ser Ala Lys Ala Ala Ala
                485                 490                 495

Pro Val Ser Ser Ala Thr Pro Ser Ser His Ser Tyr Thr Ser Asn Gly
                500                 505                 510

Ser Ser Ser Asp Val Ala Gly Gln Val Arg Gly Leu Leu Ala Gln
            515                 520                 525

Gly Tyr Arg Ile Ser Ala Glu Val Ala Asp Lys Arg Phe Gln Thr
            530                 535                 540

Ser Ser Trp Gln Ser Leu Pro Ala Leu Ser Gly Gln Ser Glu Ala Thr
545                 550                 555                 560

Val Leu Pro Ala Leu Glu Ser Ile Leu Gln Glu His Lys Gly Lys Tyr
                565                 570                 575

Val Arg Leu Ile Gly Ile Asp Pro Ala Ala Arg Arg Val Ala Glu
            580                 585                 590

Leu Leu Ile Gln Lys Pro
            595
```

<210> SEQ ID NO 37
<211> LENGTH: 349
<212> TYPE: PRT
<213> ORGANISM: Artificial Sequence
<220> FEATURE:
<223> OTHER INFORMATION: A synthetic protein

<400> SEQUENCE: 37

```
Met Thr Val Ser Ala Tyr Asn Gly Gln Gly Arg Leu Ser Ser Glu Val
1               5                   10                  15

Ile Thr Gln Val Arg Ser Leu Leu Asn Gln Gly Tyr Arg Ile Gly Thr
            20                  25                  30

Glu His Ala Asp Lys Arg Arg Phe Arg Thr Ser Ser Trp Gln Pro Cys
            35                  40                  45

Ala Pro Ile Gln Ser Thr Asn Glu Arg Gln Val Leu Ser Glu Leu Glu
50                  55                  60
```

```
Asn Cys Leu Ser Glu His Glu Gly Glu Tyr Val Arg Leu Leu Gly Ile
 65                  70                  75                  80

Asp Thr Asn Thr Arg Ser Arg Val Phe Glu Ala Leu Ile Gln Arg Pro
                 85                  90                  95

Asp Gly Ser Val Pro Glu Ser Leu Gly Ser Gln Pro Val Ala Val Ala
            100                 105                 110

Ser Gly Gly Arg Gln Ser Ser Tyr Ala Ser Val Ser Gly Asn Leu
        115                 120                 125

Ser Ala Glu Val Val Asn Lys Val Arg Asn Leu Leu Ala Gln Gly Tyr
    130                 135                 140

Arg Ile Gly Thr Glu His Ala Asp Lys Arg Phe Arg Thr Ser Ser
145                 150                 155                 160

Trp Gln Ser Cys Ala Pro Ile Gln Ser Ser Asn Glu Arg Gln Val Leu
                165                 170                 175

Ala Glu Leu Glu Asn Cys Leu Ser Glu His Glu Gly Glu Tyr Val Arg
            180                 185                 190

Leu Leu Gly Ile Asp Thr Ala Ser Arg Ser Arg Val Phe Glu Ala Leu
        195                 200                 205

Ile Gln Asp Pro Gln Gly Pro Val Gly Ser Ala Lys Ala Ala Ala
    210                 215                 220

Pro Val Ser Ser Ala Thr Pro Ser Ser His Ser Tyr Thr Ser Asn Gly
225                 230                 235                 240

Ser Ser Ser Ser Asp Val Ala Gly Val Arg Gly Leu Leu Ala Gln
            245                 250                 255

Gly Tyr Arg Ile Ser Ala Glu Val Ala Asp Lys Arg Phe Gln Thr
    260                 265                 270

Ser Ser Trp Gln Ser Leu Pro Ala Leu Ser Gly Gln Ser Glu Ala Thr
        275                 280                 285

Val Leu Pro Ala Leu Glu Ser Ile Leu Gln Glu His Lys Gly Lys Tyr
    290                 295                 300

Val Arg Leu Ile Gly Ile Asp Pro Ala Arg Arg Val Ala Glu
305                 310                 315                 320

Leu Leu Ile Gln Lys Pro Gly Ser Gly Gly Ser Val Tyr Gly Lys Glu
            325                 330                 335

Gln Phe Leu Arg Met Arg Gln Ser Met Phe Pro Asp Arg
        340                 345

<210> SEQ ID NO 38
<211> LENGTH: 608
<212> TYPE: PRT
<213> ORGANISM: Artificial Sequence
<220> FEATURE:
<223> OTHER INFORMATION: A synthetic protein

<400> SEQUENCE: 38

Met Thr Val Ser Ala Tyr Asn Gly Gln Gly Arg Leu Ser Ser Glu Val
  1               5                  10                  15

Ile Thr Gln Val Arg Ser Leu Leu Asn Gln Gly Tyr Arg Ile Gly Thr
                 20                  25                  30

Glu His Ala Asp Lys Arg Arg Phe Arg Thr Ser Ser Trp Gln Pro Cys
             35                  40                  45

Ala Pro Ile Gln Ser Thr Asn Glu Arg Gln Val Leu Ser Glu Leu Glu
        50                  55                  60

Asn Cys Leu Ser Glu His Glu Gly Glu Tyr Val Arg Leu Leu Gly Ile
 65                  70                  75                  80
```

```
Asp Thr Asn Thr Arg Ser Arg Val Phe Glu Ala Leu Ile Gln Arg Pro
                85                  90                  95
Asp Gly Ser Val Pro Glu Ser Leu Gly Ser Gln Pro Val Ala Val Ala
            100                 105                 110
Ser Gly Gly Gly Arg Gln Ser Ser Tyr Ala Ser Val Ser Gly Asn Leu
        115                 120                 125
Ser Ala Glu Val Val Asn Lys Val Arg Asn Leu Leu Ala Gln Gly Tyr
    130                 135                 140
Arg Ile Gly Thr Glu His Ala Asp Lys Arg Arg Phe Arg Thr Ser Ser
145                 150                 155                 160
Trp Gln Ser Cys Ala Pro Ile Gln Ser Ser Asn Glu Arg Gln Val Leu
                165                 170                 175
Ala Glu Leu Glu Asn Cys Leu Ser Glu His Glu Gly Glu Tyr Val Arg
            180                 185                 190
Leu Leu Gly Ile Asp Thr Ala Ser Arg Ser Arg Val Phe Glu Ala Leu
        195                 200                 205
Ile Gln Asp Pro Gln Gly Pro Val Gly Ser Ala Lys Ala Ala Ala Ala
    210                 215                 220
Pro Val Ser Ser Ala Thr Pro Ser Ser His Ser Tyr Thr Ser Asn Gly
225                 230                 235                 240
Ser Ser Ser Ser Asp Val Ala Gly Gln Val Arg Gly Leu Leu Ala Gln
                245                 250                 255
Gly Tyr Arg Ile Ser Ala Glu Val Ala Asp Lys Arg Arg Phe Gln Thr
            260                 265                 270
Ser Ser Trp Gln Ser Leu Pro Ala Leu Ser Gly Gln Ser Glu Ala Thr
        275                 280                 285
Val Leu Pro Ala Leu Glu Ser Ile Leu Gln Glu His Lys Gly Lys Tyr
    290                 295                 300
Val Arg Leu Ile Gly Ile Asp Pro Ala Ala Arg Arg Arg Val Ala Glu
305                 310                 315                 320
Leu Leu Ile Gln Lys Pro Gly Ser Arg Lys Leu Ile Glu Gly Leu Arg
                325                 330                 335
His Phe Arg Thr Ser Tyr Tyr Pro Ser His Arg Asp Leu Phe Glu Gln
            340                 345                 350
Phe Ala Lys Gly Gln His Pro Arg Val Leu Phe Ile Thr Cys Ser Asp
        355                 360                 365
Ser Arg Ile Asp Pro Asn Leu Ile Thr Gln Ser Gly Met Gly Glu Leu
    370                 375                 380
Phe Val Ile Arg Asn Ala Gly Asn Leu Ile Pro Pro Phe Gly Ala Ala
385                 390                 395                 400
Asn Gly Gly Glu Gly Ala Ser Ile Glu Tyr Ala Ile Ala Ala Leu Asn
                405                 410                 415
Ile Glu His Val Val Cys Gly His Ser His Cys Gly Ala Met Lys
            420                 425                 430
Gly Leu Leu Lys Leu Asn Gln Leu Gln Glu Asp Met Pro Leu Val Tyr
        435                 440                 445
Asp Trp Leu Gln His Ala Gln Ala Thr Arg Arg Leu Val Leu Asp Asn
    450                 455                 460
Tyr Ser Gly Tyr Glu Thr Asp Asp Leu Val Glu Ile Leu Val Ala Glu
465                 470                 475                 480
Asn Val Leu Thr Gln Ile Glu Asn Leu Lys Thr Tyr Pro Ile Val Arg
                485                 490                 495
```

-continued

Ser Arg Leu Phe Gln Gly Lys Leu Gln Ile Phe Gly Trp Ile Tyr Glu
            500                 505                 510

Val Glu Ser Gly Glu Val Leu Gln Ile Ser Arg Thr Ser Ser Asp Asp
    515                 520                 525

Thr Gly Ile Asp Glu Cys Pro Val Arg Leu Pro Gly Ser Gln Glu Lys
530                 535                 540

Ala Ile Leu Gly Arg Cys Val Val Pro Leu Thr Glu Glu Val Ala Val
545                 550                 555                 560

Ala Pro Pro Glu Pro Glu Pro Val Ile Ala Ala Val Ala Ala Pro Pro
                565                 570                 575

Ala Asn Tyr Ser Ser Arg Gly Trp Leu Gly Ser Gly Gly Ser Val Tyr
            580                 585                 590

Gly Lys Glu Gln Phe Leu Arg Met Arg Gln Ser Met Phe Pro Asp Arg
        595                 600                 605

<210> SEQ ID NO 39
<211> LENGTH: 23
<212> TYPE: DNA
<213> ORGANISM: Artificial Sequence
<220> FEATURE:
<223> OTHER INFORMATION: A synthetic primer

<400> SEQUENCE: 39
ggtgcactac tagtacaatc tgc                                        23

<210> SEQ ID NO 40
<211> LENGTH: 25
<212> TYPE: DNA
<213> ORGANISM: Artificial Sequence
<220> FEATURE:
<223> OTHER INFORMATION: A synthetic primer

<400> SEQUENCE: 40
gtgaaatacc gcactagtgc gtaag                                      25

<210> SEQ ID NO 41
<211> LENGTH: 28
<212> TYPE: DNA
<213> ORGANISM: Artificial Sequence
<220> FEATURE:
<223> OTHER INFORMATION: A synthetic primer

<400> SEQUENCE: 41
ctttcatctt gaattccgac tctttagg                                   28

<210> SEQ ID NO 42
<211> LENGTH: 20
<212> TYPE: DNA
<213> ORGANISM: Artificial Sequence
<220> FEATURE:
<223> OTHER INFORMATION: A synthetic primer

<400> SEQUENCE: 42
gctcggcata tgctaacctc                                            20

<210> SEQ ID NO 43
<211> LENGTH: 32
<212> TYPE: DNA
<213> ORGANISM: Artificial Sequence
<220> FEATURE:
<223> OTHER INFORMATION: A synthetic primer

<400> SEQUENCE: 43
gggaggttag catatgctct agaagctgca gg					32

<210> SEQ ID NO 44
<211> LENGTH: 23
<212> TYPE: DNA
<213> ORGANISM: Artificial Sequence
<220> FEATURE:
<223> OTHER INFORMATION: A synthetic primer

<400> SEQUENCE: 44
ctactgagtc cgaagctttc agc					23

<210> SEQ ID NO 45
<211> LENGTH: 25
<212> TYPE: DNA
<213> ORGANISM: Artificial Sequence
<220> FEATURE:
<223> OTHER INFORMATION: A synthetic primer

<400> SEQUENCE: 45
gaattataac catatgcatc ctagg					25

<210> SEQ ID NO 46
<211> LENGTH: 21
<212> TYPE: DNA
<213> ORGANISM: Artificial Sequence
<220> FEATURE:
<223> OTHER INFORMATION: A synthetic primer

<400> SEQUENCE: 46
tcccgtctag acagcgtaat g					21

<210> SEQ ID NO 47
<211> LENGTH: 23
<212> TYPE: DNA
<213> ORGANISM: Artificial Sequence
<220> FEATURE:
<223> OTHER INFORMATION: A synthetic primer

<400> SEQUENCE: 47
gagtatcact catatgcgca agc					23

<210> SEQ ID NO 48
<211> LENGTH: 21
<212> TYPE: DNA
<213> ORGANISM: Artificial Sequence
<220> FEATURE:
<223> OTHER INFORMATION: A synthetic primer

<400> SEQUENCE: 48
cttcgggatc cgctagcatt g					21

<210> SEQ ID NO 49
<211> LENGTH: 22
<212> TYPE: DNA
<213> ORGANISM: Artificial Sequence
<220> FEATURE:
<223> OTHER INFORMATION: A synthetic primer

<400> SEQUENCE: 49
tagcgaggca agatctgtga gc					22

```
<210> SEQ ID NO 50
<211> LENGTH: 24
<212> TYPE: DNA
<213> ORGANISM: Artificial Sequence
<220> FEATURE:
<223> OTHER INFORMATION: A synthetic primer

<400> SEQUENCE: 50
cctgcagctt ctagagctgc tgtg                                          24

<210> SEQ ID NO 51
<211> LENGTH: 24
<212> TYPE: DNA
<213> ORGANISM: Artificial Sequence
<220> FEATURE:
<223> OTHER INFORMATION: A synthetic primer

<400> SEQUENCE: 51
gttgttgttc ggatcccaac caac                                          24

<210> SEQ ID NO 52
<211> LENGTH: 34
<212> TYPE: DNA
<213> ORGANISM: Artificial Sequence
<220> FEATURE:
<223> OTHER INFORMATION: A synthetic primer

<400> SEQUENCE: 52
cccagatctg gaggcagtgt ctacggcaag gaac                               34

<210> SEQ ID NO 53
<211> LENGTH: 25
<212> TYPE: DNA
<213> ORGANISM: Artificial Sequence
<220> FEATURE:
<223> OTHER INFORMATION: A synthetic primer

<400> SEQUENCE: 53
cgtggccatg gcttcttggg agagc                                         25

<210> SEQ ID NO 54
<211> LENGTH: 28
<212> TYPE: DNA
<213> ORGANISM: Artificial Sequence
<220> FEATURE:
<223> OTHER INFORMATION: A synthetic primer

<400> SEQUENCE: 54
gcccttgtca gatctcgcaa gctcatcg                                      28

<210> SEQ ID NO 55
<211> LENGTH: 25
<212> TYPE: DNA
<213> ORGANISM: Artificial Sequence
<220> FEATURE:
<223> OTHER INFORMATION: A synthetic primer

<400> SEQUENCE: 55
ctagcgagca tatgaccgtg agcgc                                         25

<210> SEQ ID NO 56
<211> LENGTH: 27
<212> TYPE: DNA
<213> ORGANISM: Artificial Sequence
<220> FEATURE:
<223> OTHER INFORMATION: A synthetic primer
```

<400> SEQUENCE: 56
caggatcctc ccggcttttg ttagagc                                27

<210> SEQ ID NO 57
<211> LENGTH: 19
<212> TYPE: DNA
<213> ORGANISM: Artificial Sequence
<220> FEATURE:
<223> OTHER INFORMATION: A synthetic primer

<400> SEQUENCE: 57
cagcggccgc gcctagtgc                                         19

<210> SEQ ID NO 58
<211> LENGTH: 29
<212> TYPE: DNA
<213> ORGANISM: Artificial Sequence
<220> FEATURE:
<223> OTHER INFORMATION: A synthetic primer

<400> SEQUENCE: 58
gcttgcgcat ctcgagtgat actcgggac                              29

<210> SEQ ID NO 59
<211> LENGTH: 29
<212> TYPE: DNA
<213> ORGANISM: Artificial Sequence
<220> FEATURE:
<223> OTHER INFORMATION: A synthetic primer

<400> SEQUENCE: 59
gcggcaattc tagataggat cgaagcatc                              29

<210> SEQ ID NO 60
<211> LENGTH: 29
<212> TYPE: DNA
<213> ORGANISM: Artificial Sequence
<220> FEATURE:
<223> OTHER INFORMATION: A synthetic primer

<400> SEQUENCE: 60
tacccatgga ctcaagcgct cattgccag                              29

<210> SEQ ID NO 61
<211> LENGTH: 26
<212> TYPE: DNA
<213> ORGANISM: Artificial Sequence
<220> FEATURE:
<223> OTHER INFORMATION: A synthetic primer

<400> SEQUENCE: 61
ggtaccgagc tcgagttgac ataagc                                 26

<210> SEQ ID NO 62
<211> LENGTH: 21
<212> TYPE: DNA
<213> ORGANISM: Artificial Sequence
<220> FEATURE:
<223> OTHER INFORMATION: A synthetic primer

<400> SEQUENCE: 62
tccgcggctc tagagccgat c                                      21

```
<210> SEQ ID NO 63
<211> LENGTH: 20
<212> TYPE: DNA
<213> ORGANISM: Artificial Sequence
<220> FEATURE:
<223> OTHER INFORMATION: A synthetic primer

<400> SEQUENCE: 63
tgcctattgc ggttggaatg                                          20

<210> SEQ ID NO 64
<211> LENGTH: 20
<212> TYPE: DNA
<213> ORGANISM: Artificial Sequence
<220> FEATURE:
<223> OTHER INFORMATION: A synthetic primer

<400> SEQUENCE: 64
aatcatgatg cacgcccttg                                          20

<210> SEQ ID NO 65
<211> LENGTH: 20
<212> TYPE: DNA
<213> ORGANISM: Artificial Sequence
<220> FEATURE:
<223> OTHER INFORMATION: A synthetic primer

<400> SEQUENCE: 65
aatcatgatg cacgcccttg                                          20

<210> SEQ ID NO 66
<211> LENGTH: 20
<212> TYPE: DNA
<213> ORGANISM: Artificial Sequence
<220> FEATURE:
<223> OTHER INFORMATION: A synthetic primer

<400> SEQUENCE: 66
ttagccgatt tgagcatggc                                          20

<210> SEQ ID NO 67
<211> LENGTH: 26
<212> TYPE: DNA
<213> ORGANISM: Artificial Sequence
<220> FEATURE:
<223> OTHER INFORMATION: A synthetic primer

<400> SEQUENCE: 67
cagctttgaa cattgagcat gttgtg                                   26

<210> SEQ ID NO 68
<211> LENGTH: 21
<212> TYPE: DNA
<213> ORGANISM: Artificial Sequence
<220> FEATURE:
<223> OTHER INFORMATION: A synthetic primer

<400> SEQUENCE: 68
attgccgcga taaatccgct g                                        21

<210> SEQ ID NO 69
<211> LENGTH: 539
<212> TYPE: PRT
<213> ORGANISM: Synechococcus elongatus
```

<400> SEQUENCE: 69

```
Met Pro Ser Pro Thr Val Pro Val Ala Thr Ala Gly Arg Leu Ala
1               5                   10                  15

Glu Pro Tyr Ile Asp Pro Ala Ala Gln Val His Ala Ile Ala Ser Ile
            20                  25                  30

Ile Gly Asp Val Arg Ile Ala Ala Gly Val Arg Val Ala Ala Gly Val
        35                  40                  45

Ser Ile Arg Ala Asp Glu Gly Ala Pro Phe Gln Val Gly Lys Glu Ser
    50                  55                  60

Ile Leu Gln Glu Gly Ala Val Ile His Gly Leu Glu Tyr Gly Arg Val
65                  70                  75                  80

Leu Gly Asp Asp Gln Ala Asp Tyr Ser Val Trp Ile Gly Gln Arg Val
                85                  90                  95

Ala Ile Thr His Lys Ala Leu Ile His Gly Pro Ala Tyr Leu Gly Asp
            100                 105                 110

Asp Cys Phe Val Gly Phe Arg Ser Thr Val Phe Asn Ala Arg Val Gly
        115                 120                 125

Ala Gly Ser Val Ile Met Met His Ala Leu Val Gln Asp Val Glu Ile
    130                 135                 140

Pro Pro Gly Arg Tyr Val Pro Ser Gly Ala Ile Ile Thr Thr Gln Gln
145                 150                 155                 160

Gln Ala Asp Arg Leu Pro Glu Val Arg Pro Glu Asp Arg Glu Phe Ala
                165                 170                 175

Arg His Ile Ile Gly Ser Pro Val Ile Val Arg Ser Thr Pro Ala
            180                 185                 190

Ala Thr Ala Asp Phe His Ser Thr Pro Thr Pro Ser Pro Leu Arg Pro
    195                 200                 205

Ser Ser Ser Glu Ala Thr Thr Val Ser Ala Tyr Asn Gly Gln Gly Arg
210                 215                 220

Leu Ser Ser Glu Val Ile Thr Gln Val Arg Ser Leu Leu Asn Gln Gly
225                 230                 235                 240

Tyr Arg Ile Gly Thr Glu His Ala Asp Lys Arg Arg Phe Arg Thr Ser
                245                 250                 255

Ser Trp Gln Pro Cys Ala Pro Ile Gln Ser Thr Asn Glu Arg Gln Val
            260                 265                 270

Leu Ser Glu Leu Glu Asn Cys Leu Ser Glu His Glu Gly Glu Tyr Val
        275                 280                 285

Arg Leu Leu Gly Ile Asp Thr Asn Thr Arg Ser Arg Val Phe Glu Ala
    290                 295                 300

Leu Ile Gln Arg Pro Asp Gly Ser Val Pro Glu Ser Leu Gly Ser Gln
305                 310                 315                 320

Pro Val Ala Val Ala Ser Gly Gly Arg Gln Ser Ser Tyr Ala Ser
                325                 330                 335

Val Ser Gly Asn Leu Ser Ala Glu Val Val Asn Lys Val Arg Asn Leu
            340                 345                 350

Leu Ala Gln Gly Tyr Arg Ile Gly Thr Glu His Ala Asp Lys Arg Arg
        355                 360                 365

Phe Arg Thr Ser Ser Trp Gln Ser Cys Ala Pro Ile Gln Ser Ser Asn
    370                 375                 380

Glu Arg Gln Val Leu Ala Glu Leu Glu Asn Cys Leu Ser Glu His Glu
385                 390                 395                 400

Gly Glu Tyr Val Arg Leu Leu Gly Ile Asp Thr Ala Ser Arg Ser Arg
                405                 410                 415
```

```
Val Phe Glu Ala Leu Ile Gln Asp Pro Gln Gly Pro Val Gly Ser Ala
            420                 425                 430

Lys Ala Ala Ala Pro Val Ser Ser Ala Thr Pro Ser Ser His Ser
        435                 440                 445

Tyr Thr Ser Asn Gly Ser Ser Ser Asp Val Ala Gly Gln Val Arg
    450                 455                 460

Gly Leu Leu Ala Gln Gly Tyr Arg Ile Ser Ala Glu Val Ala Asp Lys
465                 470                 475                 480

Arg Arg Phe Gln Thr Ser Ser Trp Gln Ser Leu Pro Ala Leu Ser Gly
                    485                 490                 495

Gln Ser Glu Ala Thr Val Leu Pro Ala Leu Glu Ser Ile Leu Gln Glu
                500                 505                 510

His Lys Gly Lys Tyr Val Arg Leu Ile Gly Ile Asp Pro Ala Ala Arg
            515                 520                 525

Arg Arg Val Ala Glu Leu Leu Ile Gln Lys Pro
        530                 535

<210> SEQ ID NO 70
<211> LENGTH: 161
<212> TYPE: PRT
<213> ORGANISM: Synechococcus elongatus

<400> SEQUENCE: 70

Met His Leu Pro Pro Leu Glu Pro Pro Ile Ser Asp Arg Tyr Phe Ala
1               5                   10                  15

Ser Gly Glu Val Thr Ile Ala Ala Asp Val Val Ile Ala Pro Gly Val
                20                  25                  30

Leu Leu Ile Ala Glu Ala Asp Ser Arg Ile Glu Ile Ala Ser Gly Val
            35                  40                  45

Cys Ile Gly Leu Gly Ser Val Ile His Ala Arg Gly Gly Ala Ile Ile
        50                  55                  60

Ile Gln Ala Gly Ala Leu Leu Ala Ala Gly Val Leu Ile Val Gly Gln
65                  70                  75                  80

Ser Ile Val Gly Arg Gln Ala Cys Leu Gly Ala Ser Thr Thr Leu Val
                85                  90                  95

Asn Thr Ser Ile Glu Ala Gly Val Thr Ala Pro Gly Ser Leu Leu
            100                 105                 110

Ser Ala Glu Thr Pro Pro Thr Thr Ala Thr Val Ser Ser Ser Glu Pro
        115                 120                 125

Ala Gly Arg Ser Pro Gln Ser Ser Ala Ile Ala His Pro Thr Lys Val
130                 135                 140

Tyr Gly Lys Glu Gln Phe Leu Arg Met Arg Gln Ser Met Phe Pro Asp
145                 150                 155                 160

Arg

<210> SEQ ID NO 71
<211> LENGTH: 272
<212> TYPE: PRT
<213> ORGANISM: Synechococcus elongatus

<400> SEQUENCE: 71

Met Arg Lys Leu Ile Glu Gly Leu Arg His Phe Arg Thr Ser Tyr Tyr
1               5                   10                  15

Pro Ser His Arg Asp Leu Phe Glu Gln Phe Ala Lys Gly Gln His Pro
                20                  25                  30
```

```
Arg Val Leu Phe Ile Thr Cys Ser Asp Ser Arg Ile Asp Pro Asn Leu
             35                  40                  45

Ile Thr Gln Ser Gly Met Gly Glu Leu Phe Val Ile Arg Asn Ala Gly
 50                  55                  60

Asn Leu Ile Pro Pro Phe Gly Ala Ala Asn Gly Gly Glu Gly Ala Ser
 65                  70                  75                  80

Ile Glu Tyr Ala Ile Ala Ala Leu Asn Ile Glu His Val Val Cys
             85                  90                  95

Gly His Ser His Cys Gly Ala Met Lys Gly Leu Leu Lys Leu Asn Gln
            100                 105                 110

Leu Gln Glu Asp Met Pro Leu Val Tyr Asp Trp Leu Gln His Ala Gln
            115                 120                 125

Ala Thr Arg Arg Leu Val Leu Asp Asn Tyr Ser Gly Tyr Glu Thr Asp
            130                 135                 140

Asp Leu Val Glu Ile Leu Val Ala Glu Asn Val Leu Thr Gln Ile Glu
145                 150                 155                 160

Asn Leu Lys Thr Tyr Pro Ile Val Arg Ser Arg Leu Phe Gln Gly Lys
                165                 170                 175

Leu Gln Ile Phe Gly Trp Ile Tyr Glu Val Glu Ser Gly Glu Val Leu
            180                 185                 190

Gln Ile Ser Arg Thr Ser Ser Asp Asp Thr Gly Ile Asp Glu Cys Pro
            195                 200                 205

Val Arg Leu Pro Gly Ser Gln Glu Lys Ala Ile Leu Gly Arg Cys Val
            210                 215                 220

Val Pro Leu Thr Glu Glu Val Ala Val Ala Pro Pro Glu Pro Glu Pro
225                 230                 235                 240

Val Ile Ala Ala Val Ala Ala Pro Pro Ala Asn Tyr Ser Ser Arg Gly
                245                 250                 255

Trp Leu Ala Pro Glu Gln Gln Gln Arg Ile Tyr Arg Gly Asn Ala Ser
            260                 265                 270

<210> SEQ ID NO 72
<211> LENGTH: 2056
<212> TYPE: DNA
<213> ORGANISM: Artificial Sequence
<220> FEATURE:
<223> OTHER INFORMATION: A synthetic oligonucleotide

<400> SEQUENCE: 72
agccgcggca gtcaagcgcg ccatgtgcgc gattgtcagg aacgaccggt tgatgcagct      60
gtcattgcca tcatcgatac ggtcaacgtg gaaaaccgct ccgtctacga caaacgcgag     120
cacagctaat gggcagggat tgaatccctg ctggtcattg atctggattg agcccaggct     180
tgggaggtta gcatatgacc gtgagcgctt ataacggcca aggccgactc agttccgaag     240
tcatcaccca gtccggagt ttgctgaacc agggctatcg gattgggacg gaacatgcgg      300
acaagcgccg cttccggact agctcttggc agccctgcgc gccgattcaa agcacgaacg     360
agcgccaggt cttgagcgaa ctggaaaatt gtctgagcga acacgaaggt gaatacgttc     420
gcttgctcgg catcgatacc aatactcgca gccgtgtttt tgaagccctg attaacggc      480 ccgatggttc ggttcctgaa tcgctgggga gccaaccggt ggcagtcgct tccggtggtg     540
gccgtcagag cagctatgcc agcgtcagcg gcaacctctc agcagaagtg gtcaataaag     600
tccgcaacct cttagcccaa ggctatcgga ttgggacgga acatgcagac aagcgccgct     660
ttcggactag ctcttggcag tcctgcgcac cgattcaaag ttcgaatgag cgccaggttc     720
```

```
tggctgaact ggaaaactgt ctgagcgagc acgaaggtga gtacgttcgc ctgctgggca      780
tcgacactgc tagccgcagt cgtgtttttg aagccctgat ccaagatccc caaggaccgg      840
tgggttccgc caaagcggcc gccgcacctg tgagttcggc aacgcccagc agccacagct      900
acacctcaaa tggatcgagt tcgagcgatg tcgctggaca ggttcggggt ctgctagccc      960
aaggctaccg gatcagtgcg gaagtcgccg ataagcgtcg cttccaaacc agctcttggc     1020
agagtttgcc ggctctgagt ggccagagcg aagcaactgt cttgcctgct ttggagtcaa     1080
ttctgcaaga gcacaagggt aagtatgtgc gcctgattgg gattgaccct gcggctcgtc     1140
gtcgcgtggc tgaactgttg attcaaaagc cgggatctcg caagctcatc gagggttac      1200 ggcatttccg tacgtcctac tacccgtctc atcgggacct gttcgagcag tttgccaaag     1260
gtcagcaccc tcgagtcctg ttcattacct gctcagactc gcgcattgac cctaacctca     1320
ttacccagtc gggcatgggt gagctgttcg tcattcgcaa cgctggcaat ctgatcccgc     1380
ccttcggtgc cgccaacggt ggtgaagggg catcgatcga atacgcgatc gcagctttga     1440
acattgagca tgttgtggtc tgcggtcact cgcactgcgg tgcgatgaaa gggctgctca     1500
agctcaatca gctgcaagag gacatgccgc tggtctatga ctggctgcag catgcccaag     1560
ccacccgccg cctagtcttg gataactaca gcggttatga gactgacgac ttggtagaga     1620
ttctggtcgc cgagaatgtg ctgacgcaga tcgagaacct taagacctac ccgatcgtgc     1680
gatcgcgcct ttccaaggc aagctgcaga tttttggctg gatttatgaa gttgaaagcg      1740
gcgaggtctt gcagattagc cgtaccagca gtgatgacac aggcattgat gaatgtccag     1800
tgcgtttgcc cggcagccag gagaaagcca ttctcggtcg ttgtgtcgtc cccctgaccg     1860
aagaagtggc cgttgctcca ccagagccgg agcctgtgat cgcggctgtg gcggctccac     1920
ccgccaacta ctccagtcgc ggttggttgg gatctggagg cagtgtctac ggcaaggaac     1980 agttttgcg gatgcgccag agcatgttcc ccgatcgcta agatgtgcac agcagctcta     2040
ggagctgcag ggtact                                                    2056

<210> SEQ ID NO 73
<211> LENGTH: 129
<212> TYPE: DNA
<213> ORGANISM: Artificial Sequence
<220> FEATURE:
<223> OTHER INFORMATION: A synthetic oligonucleotide

<400> SEQUENCE: 73
agccgcggca gtcaagcgcg ccatgtgcgc gattgtcagg aacgaccggt tgatgcagct       60
gtcattgcca tcatcgatac ggtcaacgtg gaaaaccgct ccgtctacga caaacgcgag      120
cacagctaa                                                              129

<210> SEQ ID NO 74

<400> SEQUENCE: 74

000

<210> SEQ ID NO 75
<211> LENGTH: 95
<212> TYPE: PRT
<213> ORGANISM: Artificial Sequence
<220> FEATURE:
<223> OTHER INFORMATION: A synthetic protein
```

```
<400> SEQUENCE: 75

Thr Val Ser Ala Tyr Asn Gly Gln Gly Arg Leu Ser Glu Val Ile
1               5                   10                  15

Thr Gln Val Arg Ser Leu Leu Asn Gln Gly Tyr Arg Ile Gly Thr Glu
            20                  25                  30

His Ala Asp Lys Arg Arg Phe Arg Thr Ser Ser Trp Gln Pro Cys Ala
        35                  40                  45

Pro Ile Gln Ser Thr Asn Glu Arg Gln Val Leu Ser Glu Leu Glu Asn
    50                  55                  60

Cys Leu Ser Glu His Glu Gly Glu Tyr Val Arg Leu Leu Gly Ile Asp
65                  70                  75                  80

Thr Asn Thr Arg Ser Arg Val Phe Glu Ala Leu Ile Gln Arg Pro
                85                  90                  95

<210> SEQ ID NO 76
<211> LENGTH: 84
<212> TYPE: PRT
<213> ORGANISM: Artificial Sequence
<220> FEATURE:
<223> OTHER INFORMATION: A synthetic protein

<400> SEQUENCE: 76

Ser Ala Glu Val Val Asn Lys Val Arg Asn Leu Leu Ala Gln Gly Tyr
1               5                   10                  15

Arg Ile Gly Thr Glu His Ala Asp Lys Arg Arg Phe Arg Thr Ser Ser
            20                  25                  30

Trp Gln Ser Cys Ala Pro Ile Gln Ser Ser Asn Glu Arg Gln Val Leu
        35                  40                  45

Ala Glu Leu Glu Asn Cys Leu Ser Glu His Gly Glu Tyr Val Arg
    50                  55                  60

Leu Leu Gly Ile Asp Thr Ala Ser Arg Ser Arg Val Phe Glu Ala Leu
65                  70                  75                  80

Ile Gln Asp Pro

<210> SEQ ID NO 77
<211> LENGTH: 85
<212> TYPE: PRT
<213> ORGANISM: Artificial Sequence
<220> FEATURE:
<223> OTHER INFORMATION: A synthetic protein

<400> SEQUENCE: 77

Ser Ser Ser Asp Val Ala Gly Gln Val Arg Gly Leu Leu Ala Gln Gly
1               5                   10                  15

Tyr Arg Ile Ser Ala Glu Val Ala Asp Lys Arg Arg Phe Gln Thr Ser
            20                  25                  30

Ser Trp Gln Ser Leu Pro Ala Leu Ser Gly Gln Ser Glu Ala Thr Val
        35                  40                  45

Leu Pro Ala Leu Glu Ser Ile Leu Gln Glu His Lys Gly Lys Tyr Val
    50                  55                  60

Arg Leu Ile Gly Ile Asp Pro Ala Ala Arg Arg Val Ala Glu Leu
65                  70                  75                  80

Leu Ile Gln Lys Pro
                85
```